US012569556B2

(12) United States Patent
Mannie

(10) Patent No.: US 12,569,556 B2
(45) Date of Patent: Mar. 10, 2026

(54) ALUMINUM BASED ADJUVANTS FOR TOLEROGENIC VACCINATION

(71) Applicant: East Carolina University, Greenville, NC (US)

(72) Inventor: Mark D. Mannie, Greenville, NC (US)

(73) Assignee: East Carolina University, Greenville, NC (US)

( * ) Notice: Subject to any disclaimer, the term of this patent is extended or adjusted under 35 U.S.C. 154(b) by 599 days.

(21) Appl. No.: 17/161,772

(22) Filed: Jan. 29, 2021

(65) Prior Publication Data

US 2021/0252137 A1 Aug. 19, 2021

Related U.S. Application Data

(62) Division of application No. 15/763,739, filed as application No. PCT/US2016/054192 on Sep. 28, 2016, now Pat. No. 10,940,200.

(60) Provisional application No. 62/233,608, filed on Sep. 28, 2015.

(51) Int. Cl.

| *A61K 39/39* | (2006.01) |
|---|---|
| *A61K 9/00* | (2006.01) |
| *A61K 33/06* | (2006.01) |
| *A61K 38/19* | (2006.01) |
| *A61K 38/21* | (2006.01) |
| *A61K 39/00* | (2006.01) |
| *A61K 47/02* | (2006.01) |
| *A61P 37/06* | (2006.01) |

(52) U.S. Cl.
CPC ............ *A61K 39/39* (2013.01); *A61K 9/0019* (2013.01); *A61K 33/06* (2013.01); *A61K 38/19* (2013.01); *A61K 38/215* (2013.01); *A61K 39/0008* (2013.01); *A61K 47/02* (2013.01); *A61P 37/06* (2018.01); *A61K 2039/55505* (2013.01); *A61K 2039/55511* (2013.01); *A61K 2039/55522* (2013.01); *A61K 2039/577* (2013.01); *A61K 2300/00* (2013.01)

(58) Field of Classification Search
None
See application file for complete search history.

(56) References Cited

U.S. PATENT DOCUMENTS

| 4,501,729 | A | | 2/1985 | Boucher et al. | |
|---|---|---|---|---|---|
| 4,701,416 | A | | 10/1987 | Nunberg | |
| 5,151,264 | A | | 9/1992 | Samain et al. | |
| 5,288,931 | A | * | 2/1994 | Chang | C07K 1/1133 |
| | | | | | 530/825 |
| 5,496,924 | A | | 3/1996 | Habermann et al. | |
| 5,521,288 | A | | 5/1996 | Linsley et al. | |
| 5,837,816 | A | | 11/1998 | Ciardelli et al. | |
| 5,981,221 | A | | 11/1999 | Hillman et al. | |

| 5,994,104 | A | | 11/1999 | Anderson et al. | |
|---|---|---|---|---|---|
| 6,109,885 | A | | 8/2000 | Micklisch et al. | |
| 6,211,342 | B1 | | 4/2001 | Hirsch et al. | |
| 6,211,427 | B1 | | 4/2001 | Cottingham et al. | |
| 6,251,396 | B1 | | 6/2001 | Gaur et al. | |
| 6,369,199 | B2 | | 4/2002 | Guegler et al. | |
| 6,482,409 | B1 | | 11/2002 | Lobb et al. | |
| 6,555,342 | B1 | | 4/2003 | Kappes et al. | |
| 6,972,322 | B2 | | 12/2005 | Fleer et al. | |
| 6,987,006 | B2 | | 1/2006 | Fleer et al. | |
| 7,087,411 | B2 | | 8/2006 | Daly et al. | |
| 7,112,659 | B2 | | 9/2006 | Mann et al. | |
| 7,112,660 | B1 | * | 9/2006 | Domingues | A61P 37/08 |
| | | | | | 424/85.2 |
| 9,745,361 | B2 | * | 8/2017 | Mannie | C07K 14/565 |
| 10,273,284 | B2 | * | 4/2019 | Mannie | C07K 14/5428 |
| 2002/0076412 | A1 | * | 6/2002 | Steinman | G01N 33/564 |
| | | | | | 514/17.9 |
| 2003/0045474 | A1 | * | 3/2003 | Sailer | A61K 38/1875 |
| | | | | | 514/8.8 |
| 2008/0193440 | A1 | | 8/2008 | Jensen | |
| 2010/0055070 | A1 | * | 3/2010 | Mannie | A61K 38/2013 |
| | | | | | 435/325 |
| 2012/0082644 | A1 | * | 4/2012 | Mannie | A61K 39/0008 |
| | | | | | 435/69.51 |
| 2014/0154743 | A1 | * | 6/2014 | Levy | C12Y 502/01008 |
| | | | | | 435/69.6 |

FOREIGN PATENT DOCUMENTS

| WO | 9324640 | A2 | 12/1993 |
|---|---|---|---|
| WO | 9427435 | A1 | 12/1994 |
| WO | 2008130382 | A2 | 10/2008 |
| WO | 2010056143 | A1 | 5/2010 |

(Continued)

OTHER PUBLICATIONS

Hogenesch et al, (Frontiers in Immunology, 2013; vol. 3, article 406, pp. 1-13).*
Tokuriki et al., 2009, Curr. Opin. Struc. Biol. 19:596-604.*
Bhattacharya et al. (2017, PLoS One 12(3): e0171355, https://doi.org/10.1371/journal.pone.0171355).*
Alaoui-Ismaili (2009, Cytokine Growth Factor Rev. 20(5-6):501-507).*
Ulloa-Aguirre et al. (2004, Traffic 5:821-837).*
Bernier et al. (2004, Curr. Opin. Pharmacol. 4:528-533).*
Abbio Tec Product Datasheet for MBP [87-99] Peptide (Year: NA).*
Wallberg et al. European Journal of Immunology. 33: 1539-1547; Published: May 9, 2003 (Year: 2003).*
Hogenesch et al., (Frontiers in Immunology, 2013; vol. 3, article 406, pp. 1-13). (Year: 2013).*

(Continued)

*Primary Examiner* — Daniel E Kolker
*Assistant Examiner* — Katherine Ann Holtzman
(74) *Attorney, Agent, or Firm* — Stanek Lemon Crouse & Meeks, PA

(57) ABSTRACT
The present invention provides methods of modulating an immunological disorder or an immune response. The methods include administering to a subject or a cell an effective amount of an autoimmune antigen and an anti-inflammatory cytokine included in an aluminum-based carrier. Compositions including an autoimmune antigen and an anti-inflammatory cytokine included in an aluminum-based carrier are also provided.

14 Claims, 17 Drawing Sheets

Specification includes a Sequence Listing.

(56) References Cited

FOREIGN PATENT DOCUMENTS

WO          2010117848 A1    10/2010
WO          2011014871 A1     2/2011
WO          2012178160 A2    12/2012

OTHER PUBLICATIONS

Abbio Tec Product Datasheet for MBP [87-99] Peptide (Year: NA) (Year: na).*

Krewski et al. Journal of Toxicology and Environmental Health, Part B, Critical Reviews. 10(1): 1-269; Published: Nov. 25, 2009 (Year: 2009).*

Charlton et al. Current Opinion in Immunology. 7: 793-798; Published: Dec. 1995 (Year: 1995).*

Ludvigsson et al. New England Journal of Medicine. 359: 1909-1920: Published: Oct. 8, 2008 (Year: 2008).*

Wherrett et al. Lancet. 378: 319-327; Published: Jun. 27, 2011 (Year: 2011).*

Wållberg et al. European Journal of Immunology. 33: 1539-1547; Published: May 9, 2003 (Year: 2003).*

Fulgenzi et al. BioMed Research International. 2014: 758323; Published: Aug. 27, 2014 (Year: 2014).*

Guimarães et al. Pharmacological Research. 100: 190-209; Published: Aug. 12, 2015 (Year: 2015).*

Bagavant et al. Clinical Experimental Rheumatology. 32(2): 251-255; Published: Apr. 9, 2015 (Year: 2015).*

Ludvigsson et al. New England Journal of Medicine. 366(2): 433-442; Published: Feb. 2, 2012 (Year: 2012).*

Wigren et al. Circulation Research. 104: e62-e70; Published: May 28, 2009 (Year: 2009).*

Piconese et al. Cytokine & growth Factor Reviews. 26: 133-141; Published: Oct. 31, 2014 (Year: 2014).*

"Abreu, S. L. "Suppression of experimental allergic encephalomy-elitis by interferon" Immunological Communications, 11(1):1-7 (1982) (Abstract only)".

"Brewer, J.M. "(How) do aluminium adjuvants work?" Immunology Letters, 102(1):10-15 (2005) (Abstract only)".

"Communication pursuant to Rule 164(1) EPC: partial supplementary European Search Report corresponding to European Patent Application No. 16852494.0 (15 pages) (dated Apr. 18, 2019)".

"Corthay, Alexandre "How do regulatory T cells work?" Scandinavian Journal of Immunology, 70:326-336 (2009)".

"Darlington, Cynthia "MBP-8298, a synthetic peptide analog of myelin basic protein for the treatment of multiple sclerosis" Current Opinion in Molecular Therapeutics, 9(4):398-402 (2007) (Abstract only)".

"Derwenskus, Joy "Current Disease-Modifying Treatment of Multiple Sclerosis" Mount Sinai Journal of Medicine, 78(2):161-175 (2011) (Abstract only)".

"European Patent Office Communication pursuant to Article 94(3) EPC corresponding to European Patent Application No. 16852494.0 (7 pages) (dated Apr. 7, 2020)".

"Extended European Search Report corresponding to European Patent Application No. 16852494.0 (12 pages) (dated Jul. 29, 2019)".

"Freedman, Mark S. "Evidence for the efficacy of interferon beta-1b in delaying the onset of clinically definite multiple sclerosis in individuals with clinically isolated syndrome" Therapeutic Advances in Neurological Disorders, 7(6):279-288 (2014)".

"Garren, H. "A DNA vaccine for multiple sclerosis" Expert Opinion on Biological Therapy, 8(10):1539-1550 (2008) (Abstract only)".

"Garren, Hideki "DNA vaccines for autoimmune diseases" Expert Review of Vaccines, 8(9):1195-1203 (2009) (Abstract only)".

"Ghimire, Tirth Raj "The mechanisms of action of vaccines containing aluminum adjuvants: an in vitro vs in vivo paradigm" SpringerPlus, 4(181):1-18 (2015)".

"Goodin, Douglas S. "The Use of Interferon Beta and Glatiramer Acetate in Multiple Sclerosis" Seminars in Neurology, 33(1):13-25 (2013) (Abstract only)".

"International Preliminary Report on Patentability corresponding to International Patent Application No. PCT/US2016/054192 (7 pages) (mailed Apr. 12, 2018)".

"Kieseier, Bernd C. "The Mechanism of Action of Interferon-beta in Relapsing Multiple Sclerosis" CNS Drugs, 25(6):491-502 (2011) (Abstract only)".

"Plosker, Greg L. "Interferon-beta-1b: a review of its use in multiple sclerosis" CNS Drugs, 25(1):67-88 (2011) (Abstract only)".

"Steinman, Lawrence "The gray aspects of white matter disease in multiple sclerosis" Proceedings of the National Academy of Sciences USA, 106(20):8083-8084 (2009)".

"Swanborg, Robert H. "Antigen-Induced Inhibition of Experimental Allergic Encephalomyelitis: II. Studies in Guinea Pigs with the Small Rat Myelin Basic Protein" The Journal of Immunology, 111(4):1067-1070 (1973)".

"Wan, Yisong Y. "GATA3: A master of many trades in immune regulation" Trends in Immunology, 35(6):233-242 (2014)".

"Wraith, David C. "Therapeutic peptide vaccines for treatment of autoimmune diseases" Immunology Letters, 122(2):134-136 (2009)".

Abbott, et al., "Neuroantigen-specific, tolerogenic vaccines: GM-CSF is a fusion partner that facilitates tolerance rather than immunity to dominant self-epitopes of myelin in murine models of experimental autoimmune encephalomyelitis (EAE)" BMC Immunology, 12(72):1-18, (" 2011).

Aimanianda, et al., ""Novel cellular and molecular mechanisms of induction of immune responses by aluminum adjuvants" Trends in Pharmacological Sciences, 30(6):287-295 (2009) (Abstract only)".

Aristimuno, et al., ""IFNbeta-1a therapy for multiple sclerosis expands regulatory CD8+ T cells and decreases memory CD8+ subset: A longitudinal 1-year study" Clinical Immunology, 134:148-157 (2010)".

Arnold, et al., ""A novel monoclonal antibody against rat LFA-1: blockade of LFA-1 and CD4 augments class II MHC expression on T cells" Hybridoma, 17(4):331-338 (1998) (Abstract only)".

Axtell, et al., ""T helper type 1 and 17 cells Determine Efficacy of interferon-beta in Multiple Sclerosis and Experimental Encephalomyelitis" Nature Medicine, 16(4):406-412 (2010)".

Axtell, et al., ""Type I Interferons: Beneficial in Th1 and Detrimental in Th17 Autoimmunity" Clinical Reviews in Allergy & Immunology, 44(2):114-120 (2013)".

Baine, et al., ""Helios induces epigenetic silencing of Il2 gene expression in regulatory T cells" The Journal of Immunology, 190(3):1008-1016 (2013)".

Bielekova, et al., ""Encephalitogenic potential of the myelin basic protein peptide (amino acids 83-99) in multiple sclerosis: Results of a phase II clinical trial with an altered peptide ligand" Nature Medicine, 6(10):1167-1175 (2000)".

Bin Dhuban, et al., ""Coexpression of TIGIT and FCRL3 identifies Helios+ human memory regulatory T cells" The Journal of Immunology, 194(8):3687-3696 (2015)".

Blanchfield, et al., ""A GMCSF-neuroantigen fusion protein is a potent tolerogen in experimental autoimmune encephalomyelitis (EAE) that is associated with efficient targeting of neuroantigen to APC" Journal of Leukocyte Biology, 87:509-521 (2010)".

Boivin, et al., ""Interferon-beta Suppresses Murine Th1 Cell Function in the Absence of Antigen-Presenting Cells" PLoS One, 10:e0124802 (2015)".

Borden, et al., ""Interferons at age 50: past, current and future impact on biomedicine" Nature Reviews Drug Discovery, 6(12):975-990 (2007) (Abstract only)".

Brod, et al., ""Modification of acute experimental autoimmune encephalomyelitis in the Lewis rat by oral administration of type 1 interferons" Journal of Interferon & Cytokine Research, 15(2):115-122 (1995) (Abstract only)".

Brod, et al., ""Oral administration of human or murine interferon alpha suppresses relapses and modifies adoptive transfer in experimental autoimmune encephalomyelitis" Journal of Neuroimmunology, 58(1):61-69 (1995) (Abstract only)".

Brod, et al., ""Oral administration of IFN-alpha is superior to subcutaneous administration of IFN-alpha in the suppression of chronic relapsing experimental autoimmune encephalomyelitis" Journal of Autoimmunity, 9(1):11-20 (1996) (Abstract only)".

(56) References Cited

OTHER PUBLICATIONS

Brod , et al., ""Suppression of experimental autoimmune encephalomyelitis by oral administration of myelin antigens: IV. Suppression of chronic relapsing disease in the Lewis rat and strain 13 guinea pig" Annals of Neurology, 29(6):615-622 (1991) (Abstract only)".

Campbell , et al., ""Myelin basic protein administration in multiple sclerosis" Archives of Neurology, 29(1):10-15 (1973) (Abstract only)".

Chen , et al., ""IFN-beta induces the proliferation of CD4+CD25+ Foxp3+ regulatory T cells through upregulation of GITRL on dendritic cells in the treatment of multiple sclerosis" Journal of Neuroimmunology, 242(1-2):39-46 (2012) (Abstract only)".

Cheng , et al., ""IFN-beta inhibits T cells accumulation in the central nervous system by reducing the expression and activity of chemokines in experimental autoimmune encephalomyelitis" Molecular Immunology, 64(1):152-162 (2015) (Abstract only)".

Cobbold , et al., ""Infectious tolerance" Current Opinion in Immunology, 10(5):518-524 (1998) (Abstract only)".

Cocco , et al., ""Profile of PEGylated interferon beta in the treatment of relapsing-remitting multiple sclerosis" Therapeutics and Clinical Risk Management, 11:759-766 (2015)".

Comabella, et al., ""Immunopathogenesis of multiple sclerosis" Clinical Immunology, 142(1):2-8 (2012) (Abstract only)".

Dasch , et al., ""Monoclonal antibodies recognizing transforming growth factor-beta. Bioactivity neutralization and transforming growth factor beta 2 affinity purification" The Journal of Immunology, 142:1536-1541 (1989)".

De Andres , et al., ""Interferon beta-1a therapy enhances CD4+ regulatory T-cell function: an ex vivo and in vitro longitudinal study in relapsing-remitting multiple sclerosis" Journal of Neuroimmunology, 182(1-2):204-211 (2007) (Abstract only)".

Dikopoulos , et al., ""Type I IFN Negatively Regulates CD8+ T Cell Responses through IL-10-Producing CD4+ T Regulatory 1 Cells" The Journal of Immunology, 174:99-109 (2005)".

Elliott , et al., ""Treatment of Experimental Encephalomyelitis with a Novel Chimeric Fusion Protein of Myelin Basic Protein and Proteolipid Protein" The Journal of Clinical Investigation, 98(7):1602-1612 (1996)".

Faria , et al., ""Oral tolerance: Therapeutic implications for autoimmune diseases" Clinical & Developmental Immunology, 13(2-4):143-157 (2006)".

Fitzgerald , et al., ""Independent and interdependent immunoregulatory effects of IL-27, IFN-beta, and IL-10 in the suppression of human Th17 cells and murine experimental autoimmune encephalomyelitis" Journal of Immunology, 190(7):3225-3234 (2013)".

Floris , et al., ""Interferon-beta directly influences monocyte infiltration into the central nervous system" Journal of Neuroimmunology, 127(1-2):69-79 (2002) (Abstract only)".

Fontoura , et al., ""Antigen-Specific Therapies in Multiple Sclerosis: Going Beyond Proteins and Peptides" International Reviews of Immunology, 24:415-446 (2005)".

Freedman , et al., ""A phase III study evaluating the efficacy and safety of MBP8298 in secondary progressive MS" Neurology, 77:1551-1560 (2011)".

Galligan , et al., ""Interferon-beta is a key regulator of proinflammatory events in experimental autoimmune encephalomyelitis" Multiple Sclerosis, 16(12):1458-1473 (2010)".

Getts , et al., ""Microparticles bearing encephalitogenic peptides induce T-cell tolerance and ameliorate experimental autoimmune encephalomyelitis" Nature Biotechnology, 30(12):1217-1224 (2012)".

Getts , et al., ""Tolerance induced by apoptotic antigen-coupled leukocytes is induced by PD-L1+ and IL-10-producing splenic macrophages and maintained by T regulatory cells" Journal of Immunology, 187(5):2405-2417 (2011)".

Ghosh , et al., ""Depletion of CD4+ CD25+ regulatory T cells confers susceptibility to experimental autoimmune encephalomyelitis (EAE) in GM-CSF-deficient Csf2-/- mice" Journal of Leukocyte Biology, 100:747-760 (2016)".

Hawiger , et al., ""Immunological Unresponsiveness Characterized by Increased Expression of CD5 on Peripheral T Cells Induced by Dendritic Cells In Vivo" Immunity, 20:695-705 (2004)".

Hertz , et al., ""Effect of rat and beta-human interferons on hyperacute experimental allergic encephalomyelitis in rats" Agents and Actions, 16(5):397-403 (1985)".

Higgins , et al., ""Suppression of experimental autoimmune encephalomyelitis by oral administration of myelin basic protein and its fragments" Journal of Immunology, 140(2):440-445 (1988) (Abstract only)".

Hou , et al., ""Interferon beta-secreting mesenchymal stem cells combined with minocycline attenuate experimental autoimmune encephalomyelitis" Journal of Neuroimmunology, 274(1-2):20-27 (2014) (Abstract only)".

Inoue , et al., ""Interferon-beta therapy against EAE is effective only when development of the disease depends on the NLRP3 inflammasome" Science Signaling, 5(225):ra38 (2012)".

Inoue , et al., ""The role of interferon-beta in the treatment of multiple sclerosis and experimental autoimmune encephalomyelitis—in the perspective of inflammasomes" Immunology, 139:11-18 (2013)".

Islam , et al., ""GM-CSF-neuroantigen fusion proteins reverse experimental autoimmune encephalomyelitis and mediate tolerogenic activity in adjuvant-primed environments: association with inflammation-dependent, inhibitory antigen presentation" The Journal of Immunology, 1", 193(5):2317-2329 (2014).

Javed , et al., ""Exquisite Peptide Specificity of Oral Tolerance in Experimental Autoimmune Encephalomyelitis" The Journal of Immunology, 155: 1599-1605 (1995)".

Jurynczyk , et al., ""Immune regulation of multiple sclerosis by transdermally applied myelin peptides" Annals of Neurology, 68(5):593-601 (2010) (Abstract only)".

Kalinke , et al., ""Endogenous, or therapeutically induced, type I interferon responses differentially modulate Th1/Th17-mediated autoimmunity in the CNS" Immunology and Cell Biology, 90:505-509 (2012)".

Kasper , et al., ""Immunomodulatory activity of interferon-beta" Annals of Clinical and Translational Neurology, 1(8):622-631 (2014)".

Khorooshi , et al., ""Induction of endogenous Type I interferon within the central nervous system plays a protective role in experimental autoimmune encephalomyelitis" Acta Neuropathologica, 130(1):107-118 (2015)".

Killestein , et al., ""Determinants of interferon beta efficacy in patients with multiple sclerosis" Nature Reviews Neurology, 7(4):221-228 (2011) (Abstract only)".

Kool , et al., ""Alum adjuvant: some of the tricks of the oldest adjuvant" Journal of Medical Microbiology, 61:927-934 (2012)".

Korporal , et al., ""Interferon beta-induced restoration of regulatory T-cell function in multiple sclerosis is prompted by an increase in newly generated naive regulatory T cells" Archives of Neurology, 65(11):1434-1439 (2008) (Abstract only)".

Lacal , et al., ""Monoclonal Antibody Y13-259 Recognizes an Epitope of the p21 ras Molecule Not Directly Involved in the GTP-Binding Activity of the Protein" Molecular and Cellular Biology, 6(4):1002-1009 (1986)".

Lee , et al., ""Type I Interferons Maintain Foxp3 Expression and T-Regulatory Cell Functions Under Inflammatory Conditions in Mice" Gastroenterology, 143(1):145-154 (2012)".

Levings , et al., ""IFN-alpha and IL-10 Induce the Differentiation of Human Type 1 T Regulatory Cells" The Journal of Immunology, 166:5530-5539 (2001)".

Limmroth , et al., "The interferon beta therapies for treatment of relapsing-remitting multiple sclerosis: are they equally efficacious? A comparative review of open-label studies evaluating the efficacy, safety, or dosing of different interferon beta formulations alone or, in combination" Therapeutic Advances in Neurological Disorders, 4(5):281-296 (2011).

Liu, et al., ""FoxA1 directs the lineage and immunosuppressive properties of a novel regulatory T cell population in EAE and MS" Nature Medicine, 20:272-282 (2014)".

(56) References Cited

OTHER PUBLICATIONS

Liu , et al., ""Tumor Evasion of the Immune System by Converting CD4+CD25-T Cells into CD4+CD25+ T Regulatory Cells: Role of Tumor-Derived TGF-beta" The Journal of Immunology, 178:2883-2892 (2007)".

Loo , et al., ""High dose antigen treatment with a peptide epitope of myelin basic protein modulates T cells in multiple sclerosis patients" Cellular Immunology, 280(1):10-15 (2012) (Abstract only)".

Lund , et al., ""Coordination of Early Protective Immunity to Viral Infection by Regulatory T Cells" Science, 320(5880):1220-1224 (2008)".

Lutterotti , et al., ""Antigen-Specific Tolerance by Autologous Myelin Peptide-Coupled Cells: A Phase 1 Trial in Multiple Sclerosis" Science Translational Medicine, 5:188ra175 (2013)".

Mannie , et al., ""A Fusion Protein Consisting of IL-16 and the Encephalitogenic Peptide of Myelin Basic Protein Constitutes an Antigen-Specific Tolerogenic Vaccine That Inhibits Experimental Autoimmune Encephalomyelitis" The Journal of Immunology, 179:1458-1465 (2007)".

Mannie , et al., ""Class II MHC/peptide complexes on T cell antigen-presenting cells: agonistic antigen recognition inhibits subsequent antigen presentation" Cellular Immunology, 186(2):111-120 (1998) (Abstract only)".

Mannie , et al., ""Cytokine-neuroantigen fusion proteins as a new class of tolerogenic, therapeutic vaccines for treatment of inflammatory demyelinating disease in rodent models of multiple sclerosis" Frontiers in Immunology, 3(255):1-16 (2012)".

Mannie , et al., ""Cytokine-neuroantigen fusion proteins: new tools for modulation of myelin basic protein (MBP)-specific T cell responses in experimental autoimmune encephalomyelitis" The Journal of Immunological Methods, 319(1-2):118-132 (2007) (Abstract only)".

Mannie , et al., ""Experimental Autoimmune Encephalomyelitis in Lewis rats: IFN-beta Acts As a Tolerogenic Adjuvant for Induction of Neuroantigen-Dependent Tolerance" The Journal of Immunology, 182:5331-5341 (2009)".

Mannie , et al., ""IL-2/Neuroantigen Fusion Proteins as Antigen-Specific Tolerogens in Experimental Autoimmune Encephalomyelitis (EAE): Correlation of T Cell-Mediated Antigen Presentation and Tolerance Induction" The Journal of Immunology, 178:2835-2843 (2007)".

Mannie , et al., ""Parallel costimulatory pathways promote myelin basic protein-stimulated proliferation of encephalitogenic rat T cells" Cellular Immunology, 153(2):312-328 (1994) (Abstract only)".

Mannie , et al., ""Tolerogenic vaccines for Multiple sclerosis" Human Vaccines & Immunotherapeutics, 9(5):1032-1038 (2013)".

Marta , et al., ""Pathogenic myelin oligodendrocyte glycoprotein antibodies recognize glycosylated epitopes and perturb oligodendrocyte physiology" Proceedings of the National Academy of Sciences USA, 102(39):13992-13997 (2005)".

Marziniak , et al., ""Current Perspectives on Interferon Beta-1b for the Treatment of Multiple Sclerosis" Advances in Therapy, 31(9):915-931 (2014)".

Mcfarland , et al., ""Effective Antigen-Specific Immunotherapy in the Marmoset Model of Multiple Sclerosis" The Journal of Immunology, 166:2116-2121 (2001)".

Mcgraw , et al., ""Interferon Beta and Glatiramer Acetate Therapy" Neurotherapeutics, 10:2-18 (2013)".

Metidji , et al., ""IFN-alpha/beta Receptor Signaling Promotes Regulatory T Cell Development and Function Under Stress Conditions" The Journal of Immunology, 194(9):4265-4276 (2015)".

Miller , et al., ""Experimental Autoimmune Encephalomyelitis in the Mouse" Current Protocols in Immunology, 77(1):15.1.1-15.1.18 (2007)".

Mori , et al., ""The vaccine adjuvant alum inhibits IL-12 by promoting PI3 kinase signaling while chitosan does not inhibit IL-12 and enhances Th1 and Th17 responses" European Journal of Immunology, 42:2709-2719 (2012)".

Namdar , et al., ""Effect of IFN-beta therapy on the frequency and function of CD4(+)CD25(+) regulatory T cells and Foxp3 gene expression in relapsing-remitting multiple sclerosis (RRMS): a preliminary study" Journal of Neuroimmunology, 218:120-124 (2010)".

Nikfar , et al., ""A meta-analysis of the efficacy and tolerability of interferon-beta in multiple sclerosis, overall and by drug and disease type" Clinical Therapeutics, 32(11):1871-1888 (2010) (Abstract only)".

Nylander , et al., ""Multiple Sclerosis" The Journal of Clinical Investigation, 122(4):1180-1188 (2012)".

Oleszycka, et al., ""Immunomodulatory properties of the vaccine adjuvant alum" Current Opinion in Immunology, 28:1-5 (2014) (Abstract only)".

Oliveira , et al., ""Adjuvant facilitates tolerance induction to factor VIII in hemophilic mice through a Foxp3-independent mechanism that relies on IL-10" Blood, 121(19):3936-3945 (2013)".

Oliver , et al., ""Interferon therapy in relapsing-remitting multiple sclerosis: a systematic review and meta-analysis of the comparative trials" Journal of the Neurological Sciences, 302(1-2):96-105 (2011) (Abstract only)".

Oliver , et al., ""Rat and Human Myelin Oligodendrocyte Glycoproteins Induce Experimental Autoimmune Encephalomyelitis by Different Mechanisms in C57BL/6 Mice" The Journal of Immunology, 171:462-468 (2003)".

Olson , et al., ""Interleukin 35: a key mediator of suppression and the propagation of infectious tolerance" Frontiers in Immunology, 4(315):1-12 (2013)".

Papadopoulou , et al., ""Evolution of MS lesions to black holes under DNA vaccine treatment" Journal of Neurology, 259:1375-1382 (2012)".

Piconese , et al., ""Divergent effects of type-I interferons on regulatory T cells" Cytokine & Growth Factor Reviews, 26(2):133-141 (2015) (Abstract only)".

Prinz , et al., ""Distinct and Nonredundant In Vivo Functions of IFNAR on Myeloid Cells Limit Autoimmunity in the Central Nervous System" Immunity, 28:675-686 (2008)".

Raffin , et al., ""Human Memory Helios2 FOXP3+ Regulatory T Cells (Tregs) Encompass Induced Tregs That Express Aiolos and Respond to IL-1b by Downregulating Their Suppressor Functions" The Journal of Immunology, 191(9):4619-4627 (2013)".

Rangachari , et al., ""Using EAE to better understand principles of immune function and autoimmune pathology" Journal of Autoimmunity, 45:31-39 (2013)".

Reed, et al., ""New horizons in adjuvants for vaccine development" Trends in Immunology, 30(1):23-32 (2009) (Abstract only)".

Rudick , et al., ""Beta-interferon for multiple sclerosis" Experimental Cell Research, 317(9):1301-1311 (2011) (Abstract only)".

Sabatos-Peyton , et al., ""Antigen-specific immunotherapy of autoimmune and allergic diseases" Current Opinion in Immunology, 22:609-615 (2010)".

Sanford , et al., ""Subcutaneous recombinant interferon-beta-1a (Rebif®): a review of its use in the treatment of relapsing multiple sclerosis" Drugs, 71(14):1865-1891 (2011) (Abstract only)".

Setiady , et al., ""In vivo depletion of CD4+FOXP3+ Treg cells by the PC61 anti-CD25 monoclonal antibody is mediated by Fcgamma-maRIII+ phagocytes" European Journal of Immunology, 40(3):780-786 (2010)".

Shevach , et al., ""tTregs, pTregs, and iTregs: Similarities and Differences" Immunological Reviews, 259(1):88-102 (2014)".

Simmons , et al., ""Modeling the Heterogeneity of Multiple Sclerosis in Animals" Trends in Immunology, 34 (8):410-422 (2013)".

Stassen , et al., ""Human CD(4+)CD(25+) regulatory T cells and infectious tolerance" Transplantation, 77(1):S23-S25 (2004)".

Stern , et al., ""Promoting tolerance to proteolipid protein-induced experimental autoimmune encephalomyelitis through targeting dendritic cells" Proceedings of the National Academy of Sciences USA, 107(40):17280-17285 (2010)".

Stewart , et al., ""Interferon-dependent IL-10 production by Tregs limits tumor Th17 inflammation" The Journal of Clinical Investigation, 123(11):4859-4874 (2013)".

Takatori , et al., ""Helios Enhances Treg Cell Function in Cooperation With FoxP3" Arthritis & Rheumatology, 67(6):1491-1502 (2015)".

Tuohy , et al., ""Modulation of the IL-10/IL-12 cytokine circuit by interferon-beta inhibits the development of epitope spreading and

(56)            References Cited

OTHER PUBLICATIONS disease progression in murine autoimmune encephalomyelitis" Journal of Neuroimmunology, 111(1-2):55-63 (2000) (Abstract only)".
Vandenbark , et al., ""Interferon-beta-1a treatment increases CD56bright natural killer cells and CD4+CD25+ Foxp3 expression in subjects with multiple sclerosis" Journal of Neuroimmunology, 215(1-2):125-128 (2009) (Abstract only)".
Vriesendorp , et al., ""Oral administration of type I interferon modulates the course of experimental allergic neuritis" Autoimmunity, 24(3):157-165 (1996) (Abstract only)".
Walczak , et al., ""Transdermal Application of Myelin Peptides in Multiple Sclerosis Treatment" JAMA Neurology, 70(9):1105-1109 (2013)".
Waldmann , et al., ""Infectious tolerance and the long-term acceptance of transplanted tissue" Immunological Reviews, 212:301-313 (2006) (Abstract only)".
Wang , et al., ""IFN-Beta Facilitates Neuroantigen-Dependent Induction of CD25+ FOXP3+ Regulatory T Cells that Suppress Experimental Autoimmune Encephalomyelitis" The Journal of Immunology, 197:2992-3007 (2016)".
Wang , et al., ""An Essential Role of the Transcription Factor GATA-3 for the Function of Regulatory T Cells" Immunity, 35(3):337-348 (2011)".
Wang , et al., ""An Intrinsic Mechanism Predisposes Foxp3-Expressing Regulatory T Cells to Th2 Conversion In Vivo" The Journal of Immunology, 185(10):5983-5992 (2010)".
Weiner , et al., ""Oral Tolerance" Immunological Reviews, 206:232-259 (2005)".
Wigren , et al., ""Atheroprotective Effects of Alum Are Associated With Capture of Oxidized LDL Antigens and Activation of Regulatory T Cells" Circulation Research, 104(12):e62-70 (2009)".
Yasuda , et al., ""Interferon beta modulates experimental autoimmune encephalomyelitis by altering the pattern of cytokine secretion" Immunological Investigations, 28(2-3):115-126 (1999) (Abstract only)".
Yu, et al., ""Interferon-beta inhibits progression of relapsing-remitting experimental autoimmune encephalomyelitis" Journal of Neuroimmunology, 64(1):91-100 (1996) (Abstract only)".
Zhornitsky , et al., ""Prolactin in combination with interferon-beta reduces disease severity in an animal model of multiple sclerosis" Journal of Neuroinflammation, 12(55):1-7 (2015)".
Ziegler-Heitbrock , et al., ""IFN-alpha Induces the Human IL-10 Gene by Recruiting Both IFN Regulatory Factor 1 and Stat3" The Journal of Immunology, 171:285-290 (2003)".
Zou , et al., ""Overexpression of human transforming growth factor-beta1 using a recombinant CHO cell expression system" Protein Expression and Purification, 37(2):265-272 (2004) (Abstract only)".
Examination Report corresponding to European Application No. 16852494.0 dated Dec. 4, 2023.
Moorman et al., "A GMCSF-Neuroantigen Tolerogenic Vaccine Elicits Systemic Lymphocytosis of CD4+ CD25high FOXP3+ Regulatory T Cells in Myelin-Specific TCR Transgenic Mice Contigent Upon Low-Efficiency T Cell Antigen Receptor Recognition," Frontiers in Immunology, Jan. 2019, vol. 9, Article 3119, 21 pages.
Kenney et al., Protective Immunity Using Recombinant Human IL-12 and Alum as Adjuvants in a Primate Model of Cutaneous Leishmaniasis, J Immunol, 1999, 163(8), pp. 4481-4488.
Faul et al.,. Interereron-β expressed by a rabies virus-based HIV-1 vaccine vector serves as a molecular adjuvant and decreases pathogenicity, Virology, Dec. 20, 2008, 382(2), pp. 226-238.
Casas et al., "Redosing with Intralymphatic GAD-Alum in the Treatment of Type 1 Diabetes: The Diagnode-B Pilot Trial," Int. J. Mol. Sci., 2025, 26, 374, 16 pages.
Bagavant et al. "Alum, an Aluminum Based Adjuvant, Induces Sjogren's Syndrome-like Disorder in Mice," Clin Exp Rheumatol, 2014; 32(2), pp. 251-255.
Wallberg et al., "Vaccination with myelin oligodendrocyte glycoprotein adsorbed to alum effectively protects DBA/1 mice from experimental autoimmune encephalomyelitis," Eur. J. Immunol., 2003, 33, pp. 1539-1547.

* cited by examiner

FIG. 2A
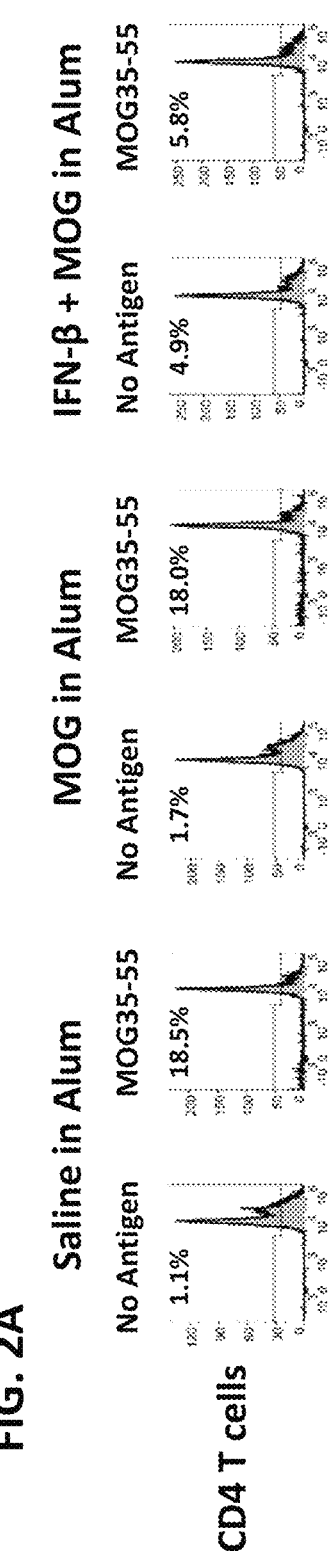
FIG. 2B
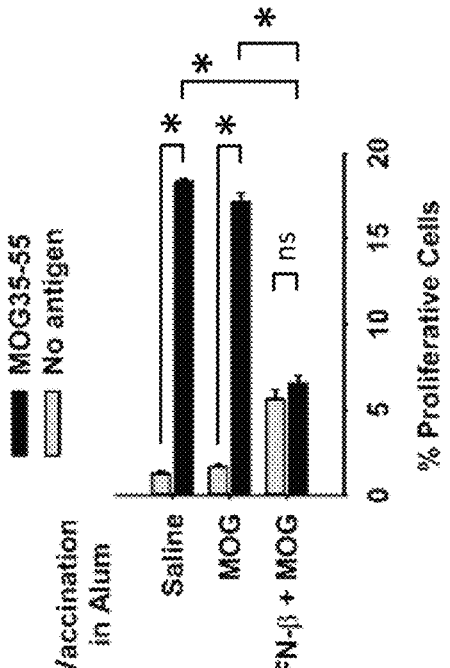
FIGS. 2A-2B

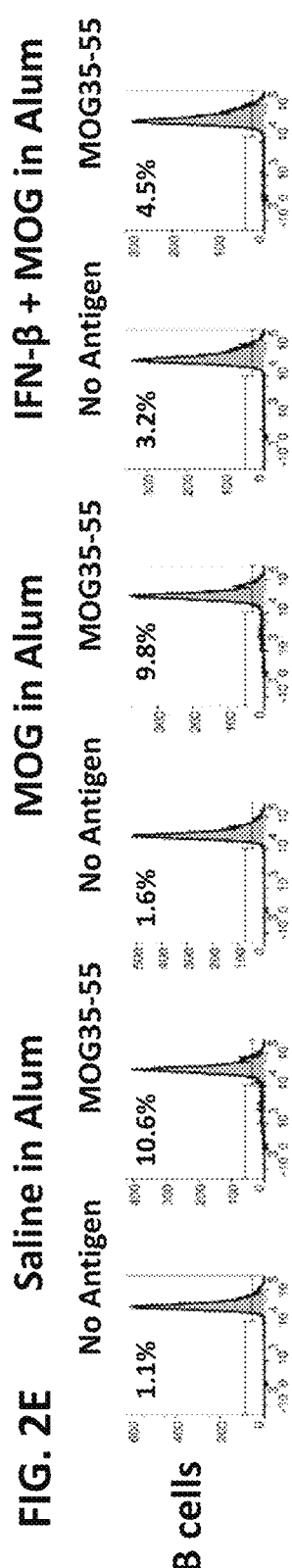
FIG. 2E
B cells
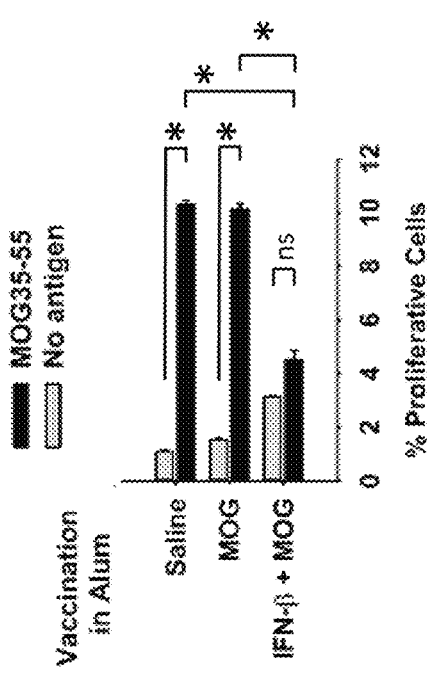
FIG. 2F
FIGS. 2E-2F

Days Since Encephalitogenic Sensitization

FIG. 6A                                   FIG. 6B

FIG. 7D
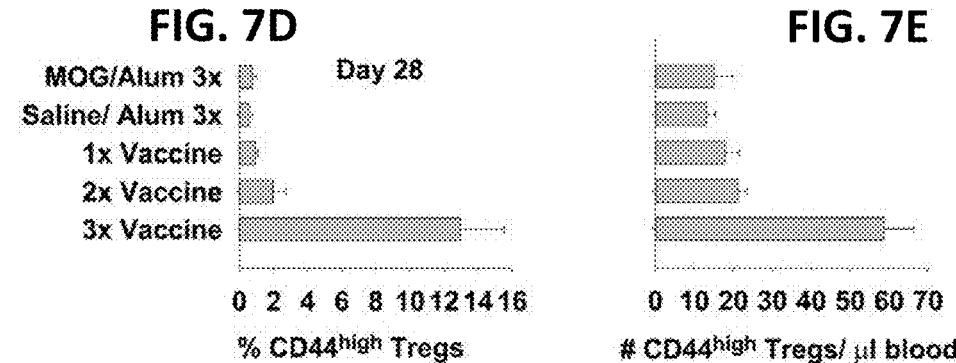
Day 28
MOG/Alum 3x
Saline/ Alum 3x
1x Vaccine
2x Vaccine
3x Vaccine
0 2 4 6 8 10 12 14 16
% CD44^high Tregs
FIG. 7E
CD44^high Tregs/ μl blood
0 10 20 30 40 50 60 70
FIG. 7F
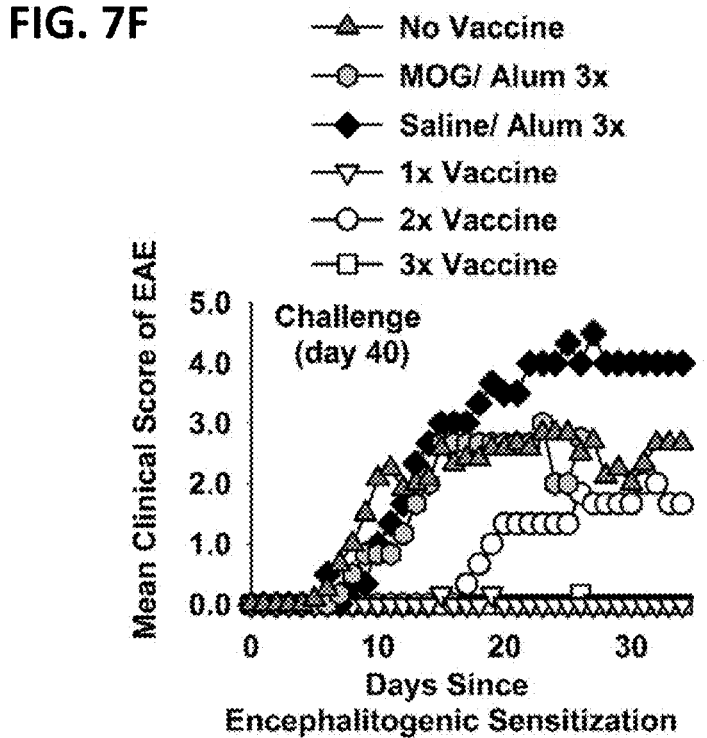
—△— No Vaccine
—◎— MOG/ Alum 3x
—◆— Saline/ Alum 3x
—▽— 1x Vaccine
—○— 2x Vaccine
—□— 3x Vaccine
Challenge (day 40)
Mean Clinical Score of EAE
Days Since Encephalitogenic Sensitization
FIGS. 7D-7F

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
cacctatgcc acccttatcc                                    20

<210> SEQ ID NO 2
<211> LENGTH: 19
```

-continued

```
<212> TYPE: DNA
<213> ORGANISM: Artificial
<220> FEATURE:
<223> OTHER INFORMATION: primer

<400> SEQUENCE: 2
attgtgggtc aaggggaag                                                    19

<210> SEQ ID NO 3
<211> LENGTH: 21
<212> TYPE: PRT
<213> ORGANISM: Artificial
<220> FEATURE:
<223> OTHER INFORMATION: Synthetic MOG35-55

<400> SEQUENCE: 3

Met Glu Val Gly Trp Tyr Arg Ser Pro Phe Ser Arg Val Val His Leu
1               5                   10                  15

Tyr Arg Asn Gly Lys
            20

<210> SEQ ID NO 4
<211> LENGTH: 14
<212> TYPE: PRT
<213> ORGANISM: Artificial
<220> FEATURE:
<223> OTHER INFORMATION: Synthetic PLP178-191

<400> SEQUENCE: 4

Asn Thr Trp Thr Thr Cys Gln Ser Ile Ala Phe Pro Ser Lys
1               5                   10

<210> SEQ ID NO 5
<211> LENGTH: 15
<212> TYPE: DNA
<213> ORGANISM: Artificial
<220> FEATURE:
<223> OTHER INFORMATION: optimal Kozak translation-initiation site

<400> SEQUENCE: 5
gccgccacca tggcc                                                        15
```

ALUMINUM BASED ADJUVANTS FOR TOLEROGENIC VACCINATION

RELATED APPLICATION DATA

This application is a divisional application of U.S. patent application Ser. No. 15/763,739, filed Mar. 27, 2018, now U.S. Pat. No. 10,940,200, issued Mar. 9, 2021, which is a 35 U.S.C. § 371 national phase application of International Application Serial No. PCT/US2016/054192, filed Sep. 28, 2016, which claims the benefit of U.S. Provisional Application Ser. No. 62/233,608, filed Sep. 28, 2015, the disclosure of each of which is incorporated herein by reference in its entirety.

STATEMENT OF GOVERNMENT SUPPORT

This invention was made with government support under RO1-NS072150 and R15-NS075830 awarded by the National Institutes of Health. The government has certain rights in the invention.

RESERVATION OF COPYRIGHT

A portion of the disclosure of this patent document contains material which is subject to copyright protection. The copyright owner, East Carolina University, Greenville, North Carolina, a constituent institution of the University of North Carolina, has no objection to the reproduction by anyone of the patent document or the patent disclosure, as it appears in Patent Office patent files or records, but otherwise reserves all copyright rights whatsoever.

STATEMENT REGARDING ELECTRONIC FILING OF A SEQUENCE LISTING

A Sequence Listing in ASCII text format, submitted under 37 C.F.R. § 1.821, entitled 5218-238DV_ST25.txt, 1,416 bytes in size, generated on Jan. 28, 2021 and filed via EFS-Web, is provided in lieu of a paper copy. This Sequence Listing is incorporated by reference into the specification for its disclosures.

FIELD OF THE INVENTION

The present invention relates to methods and compositions for inducing immunological tolerance and treating immunological disorders such as autoimmune diseases, allergic diseases, and transplant rejection.

BACKGROUND

Multiple sclerosis (MS) is an inflammatory demyelinating disease of the central nervous system (CNS) with a presumed autoimmune etiology (1-3). MS is a leading cause of non-traumatic neurological disability of young adults in the western world, including an estimated 350,000 individuals in the USA. Cell types that infiltrate the CNS in MS include CD4+ T cells which are thought to be the primary instigators of disease together with CD8+ T cells and monocytes/ macrophages. B cells may also mediate important effector functions in MS as reflected by the presence of ectopic intrathecal B cell follicles in the CNS of some MS patients and the presence of oligoclonal immunoglobulin species in the cerebrospinal fluid. First-line therapeutics for MS include the immunomodulatory IFN-β drugs which have been used since 1993 (4-9). Disadvantages of contemporary IFN-β therapy for MS include a requirement for chronic treatment, limited efficacy, and a loss of treatment benefit upon discontinuation of therapy. IFN-β efficacy is marked by substantial inter-patient variability with the implication that IFN-β therapy is optimal when MS pathogenesis is mediated by a spectrum of Th1-like effector cells (10, 11). The underlying mechanisms of IFN-β therapy are unresolved and are thought to involve rebalancing of pro-inflammatory versus anti-inflammatory cytokines such as IL-12 and IL-10 and a reset of effector and regulatory CD4+ T cell subsets. New insight into the underlying mechanisms of IFN-β action in T cell regulation and autoimmune disease may reveal new approaches to exploit the beneficial actions of IFN-β in MS.

EAE is widely used as an animal model of MS in part due to commonalities in T cell regulatory strategies (12, 13). In rodent models of EAE, CD4+ T-helper cells are the primary instigators of disease, particularly T cells of the Th1 IFN-γ producing subset and the Th17 IL-17 producing subset. In select models of EAE, B cells and antibody mediate important pathogenic roles in CNS inflammation (14, 15). EAE has been successfully controlled by different strategies of tolerogenic vaccination (16-19), and several of these tolerogenic vaccine strategies have been advanced in MS as a means to specifically target pathogenic myelin-specific T cells. Tolerogenic vaccine approaches that emerged from studies of EAE into clinical testing in MS have been based on subcutaneous injection (20) or oral delivery (21) of various myelin basic protein preparations, direct administration of myelin basic protein peptide (MBP8298, Dirucotide) (22-24), or administration of a fusion protein comprised of myelin basic protein and proteolipid protein (PLP) epitopes (MP4) (25, 26). Although these approaches had success in EAE, attempts to translate these myelin-specific vaccine strategies in MS did not show robust clinical efficacy. Indeed, use of altered peptide variants of the myelin basic protein (MBP) 83-99 peptide resulted in treatment-induced exacerbations of MS (27). Additional tolerogenic vaccine strategies that have been advanced from EAE to MS include the use of a pooled set of naked myelin peptide antigens (28), DNA vaccines that encode myelin basic protein (29), transdermal application of myelin peptides (30, 31), leukocyte-coupled peptides (32-34), and fusion proteins incorporating myelin peptides linked to a dendritic cell targeting domain (35, 36).

A novel tolerogenic vaccine strategy designed to improve therapeutic efficacy is based on the use cytokine-antigen fusion proteins that incorporate a regulatory cytokine such as IFN-β, GM-CSF, IL-2, or IL-16 with a dominant encephalitogenic epitope of a myelin autoantigen within a single-chain recombinant protein (37-44). Two previous studies (38, 41) provided evidence that IFN-could be repurposed from an inhibitory cytokine to a tolerogenic vaccine as a single-chain IFNβ-NAg fusion protein and thereby used to enable immunological tolerance to a myelin NAg. The IFNβ-NAg vaccine immunotherapy has particular promise due to widespread use of IFN-β as a well-tolerated and effective cytokine in MS. An enduring tolerogenic vaccine-induced memory would decrease the clinical need for high-frequency, high-dose administration of IFN-β and would thereby mitigate the antigenic stimulus responsible for generation of neutralizing anti-IFN-β Ab. Overall, an IFN-β-based tolerogenic vaccine may have qualitative advantages compared to IFN-β monotherapy or tolerogenic vaccination with naked myelin peptides.

Tolerogenic vaccination with cytokine-NAg fusion proteins generally required physical linkage of cytokine and NAg for optimal tolerance induction (37-50, 43, 44). This study is based on the concept that physical linkage of IFN-β and NAg could also be achieved in a substantially more flexible format by use of an intermediate that facilitated indirect, noncovalent bonds between IFN-β and NAg. The solution was provided by the Alum adjuvant which can bind and immobilize proteins onto a common matrix. IFN-β and NAg peptides mixed in the Alum adjuvant were predicted to have the required physical linkage in that both IFN-β and NAg would noncovalently bind a common substrate. This study provides evidence that IFN-β and NAg, when mixed and administered in the Alum adjuvant, elicited active tolerogenic responses that inhibited EAE in B6 mice by a mechanism dependent upon IFN-β, NAg, and Alum. The tolerogenic mechanisms reflected induction of a major FOXP3$^+$ regulatory T cell (Treg) population because culture with IFN-β and MOG35-55 induced MOG-specific FOXP3$^+$ T cells in vitro and vaccination of mice with the "IFN-β/MOG35-55/Alum" vaccine directly elicited FOXP3$^+$ Tregs in vivo. Adoptive transfer of IFN-β-induced Tregs blocked EAE, and antibody-mediated depletion of CD25$^+$ Tregs in vivo blocked tolerogenic vaccination. These data reveal IFN-β as a key cytokine controlling specification of a FOXP3$^+$ Treg lineage in vitro and in vivo. IFN-β-based tolerogenic vaccines represent a new class of highly effective tolerogenic vaccines that could be exploited as a therapy for MS.

SUMMARY

Embodiments of the present invention provide vaccination and treatment modalities for immunological disorders.

In particular, embodiments of the present invention provide methods of regulating an immunological disorder or immune response including administering to a subject or a cell an effective amount of an autoimmune antigen and an anti-inflammatory cytokine in an aluminum-based carrier.

Embodiments of the present invention also provide compositions including an autoimmune antigen, an anti-inflammatory cytokine, and an aluminum-based carrier.

Embodiments of the present invention further include methods of modulating antigen-presenting cell function including exposing an antigen-presenting cell to a combination including an autoimmune antigen and an anti-inflammatory cytokine in an aluminum-based carrier.

Embodiments of the present invention provide the use of a composition including an autoimmune antigen, an anti-inflammatory cytokine, and an aluminum-based carrier for preparation of a medicament for the prevention and/or treatment of an immunological disorder.

Embodiments of the present invention also provide kits including one or more containers having pharmaceutical dosage units including an effective amount of the components and/or compositions described herein, wherein the container is packaged with optional instructions for the use thereof.

The foregoing and other objects and aspects of the present invention are explained in greater detail in reference to the drawings and description set forth herein.

BRIEF DESCRIPTION OF THE DRAWINGS

(FIGS. 1A-1B) On day 13, groups were matched for severity of EAE (mean maximal scores of 3.1-3.3, mean cumulative scores of 25.0-26.5). MOG/CFA immunized mice were treated (2 nmoles each) with IFNβ-MOG, a combination of IFN-β and MOG35-55, MOG35-55, or saline by subcutaneous injections in saline on days 13, 15, 17, and 19. (B) Shown are maximal scores of EAE during days 20-62. (FIGS. 1C-1D) MOG/CFA immunized mice were matched for severity of EAE on day 14 (mean maximal scores of 3.2-3.4, mean cumulative scores of 16.5-17.0). Matched groups were given one subcutaneous injection (5 nmoles) of "Saline in Alum", "MOG35-55 in Alum", or "IFN-β+MOG in Alum" on day 15. (FIG. 1D) Shown are maximal scores of EAE during days 18-36. (FIGS. 1E-1F) Designated vaccines were given at a dose of 2 nmoles on days −21, −14, and −7. The EAE timecourse is shown through day 20 and the mean maximal scores are shown based on data collected through day 32. Error bars represent standard error of the mean (FIG. 1A, FIG. 1C, FIG. 1E). Bars represent the average of the values in each group (FIG. 1B, FIG. 1D, FIG. 1F). Tabular data and statistical analysis for these experiments are shown in Table 1.

FIGS. 2A-2F. Depletion of CD25$^+$ Tregs reversed the suppressive action of tolerogenic vaccination. B6 mice were vaccinated with "IFN-β+MOG35-55 in Alum" or "IFN-β+PLP178-191 in Alum" on days −21, −14, and −7 (2 nmoles in A-B & 5 nmoles in FIGS. 2C-2D). Mice were treated with the anti-CD25 PC61 mAb or the Y13 rat IgG1 isotype control (250 ug i.p.) on days −4 and −2 and were challenged with 200 ug MOG35-55 in CFA (FIGS. 2A-2B) or 200 ug PLP178-191 in CFA (FIGS. 2C-2D) on day 0 (Pertussis toxin was given on days 0 and 2). Shown are the timecourse data through day 24 for EAE (FIGS. 2A, 2C) and weight loss (FIGS. 2B, 2D). Tabular data and statistical analysis are shown in Table 1.

(FIG. 4A) Naïve 2D2-FIG splenocytes (100,000/well) were cultured in duplicate with or without 1 μM MOG35-55 in the presence or absence of 1 μM IFN-β and/or 1 nM TGF-β. After 7 days of culture, CD4$^+$ T cells were assessed for expression of GFP as an indicator of FOXP3, which is indicated as a percentage in the upper right of each dotplot. Shown are duplicate samples for each condition. (FIGS. 4B-4D) 2D2-FIG splenocytes were cultured in the presence or absence of 1 μM MOG35-55, 1 nM TGF-β, or IFN-β (x-axis, 1 pM to 1 μM) for 7 days. (FIG. 4B) Shown are FOXP3$^+$ T cells as a percentage of total viable cells. (FIG. 4C) When cultured without TGF-β, total viable T cells, FOXP3$^{(neg)}$ conventional T cells (Tconv), and FOXP3$^+$ Treg cells were assessed after a 7-day culture as a ratio relative to a fixed number of fluorescent reference beads (50,000 beads/well) or (FIG. 4D) as a function of cell size (forward scatter). Error bars represent standard deviations. These data are representative of four independent experiments.

(FIGS. 5A-5B) 2D2-FIG splenocytes were cultured with 1 μM MOG35-55 and IL-2 in the presence (IFNβ-Tregs) or absence (Control T cells) of 1 μM IFN-β for 7 days. Donor IFNβ-Tregs and control T cells were extensively washed after the 7-day culture and injected at a dose of $10^7$ total T cells on day 4 into recipients that were previously challenged with MOG35-55/CFA (day 0) and Pertussis toxin (days 0, 2). Error bars represent standard error of the mean. Shown are 1 of 2 experiments that were compiled in Table 1. (FIGS. 5C-5F) 2D2-FIG T cells were activated with 1 μM IFN-β+MOG35-55 (FIGS. 5C & 5E, FOXP3$^+$ Treg gate), 1 nM TGF-β+1 μM MOG35-55 (FIGS. 5C & 5F, FOXP3$^+$ Treg gate), or 1 μM MOG35-55 alone (FIG. 5D, Tconv cell gate) for 7 days. T cells were analyzed for the designated surface markers. These data are representative of three independent experiments. Cells were stained with CD45-BV785 and CD3-PE.CF594 within different panels that included; [CD86-BV421, CD80-PE, and CD28-APC], [CD69-BV421, CD5-PE, GARP-AF647, and PDL1-PE.Cy7], [PD1-BV421, PDL2-PE, and PDL1-APC], and [CD69-BV421, CTLA4-PE, and IFNAR1-APC].

(FIG. 6A) On days 7, 14, 29, 33, and 40, mice were bled via the submandibular vein, and circulating CD45$^+$ CD3$^+$ T cells were assessed for expression of the 2D2 TCR transgenic Vα3.2 receptor and GFP (FOXP3$^+$) expression. (FIG. 6B) The total combined percentages of transgenic Vα3.2$^+$ and nontransgenic Vα3.2$^-$ FOXP3$^+$ Tregs is given in the upper right of each dotplot. Analysis panels included CD25-BV421, TCR-Vα3.2-PE, CD3-PE.CF594, TCR-Vβ11-AF647, and CD45-BV785.

FIGS. 7A-7F. The "IFN-β+MOG in Alum" vaccine elicited FOXP3$^+$ Tregs and tolerance in 2D2 TCR transgenic mice. 2D2-FIG mice were given three (3×) injections (days 0, 7, 14), two (2×) injections (days 7 and 14), or one (1×) injection (day 14) of 5 nmoles of the "IFN-β+MOG in Alum" vaccine (n=3). When not receiving tolerogenic vaccination, mice received a control injection of Saline in Alum. Control mice were given three (3×) injections (days 0, 7, 14) of "Saline in Alum" or 5 nmoles of "MOG in Alum" (n=3). Mice were assessed for percentages (FIG. 7A) (relative to 2D2 T cell population) and absolute numbers (FIG. 7B) (cells/μl blood) of circulating FOXP3$^+$ Tregs on days 17, 21, 28, and 35. (FIG. 7A) 3× or 2× versus MOG or Saline, p<0.010 for days 17-35; 1× versus MOG or Saline, p<0.05 for days 17-28. (FIG. 7B) 3× versus MOG or Saline, p<0.006 for days 17-35; 2× versus MOG or Saline, p<0.006 for days 17-28. (FIG. 7C) On day 28, CD3$^+$ T cells were analyzed for expression of CD44 (y-axis) and FOXP3$^+$ (x-axis). Percentages of CD44$^{high}$ Tregs and CD44$^{low}$ Tregs (upper and lower right quadrants) are given for each representative dotplot. Mean percentages (FIG. 7D) and numbers (FIG. 7E) of CD44$^{high}$ FOXP3$^+$ Tregs are shown (3× versus the other 4 groups, p≤0.001). (FIGS. 7A-7B, 7D-7E) Shown are means and standard error of the mean. Analysis panels included CD25-BV421, TCR-Vα3.2-PE, CD3-PE.CF594, CD44-APC, and CD45-BV785. (FIG. 7F) Mice were challenged with 100 μg MOG35-55 in CFA on day 40, were given Pertussis toxin on days 40 and 42, and were weighed/ scored for EAE daily for the next 34 days. The compiled clinical data and statistical analysis of EAE are provided in Table 2.

Figures 8A, 8B:
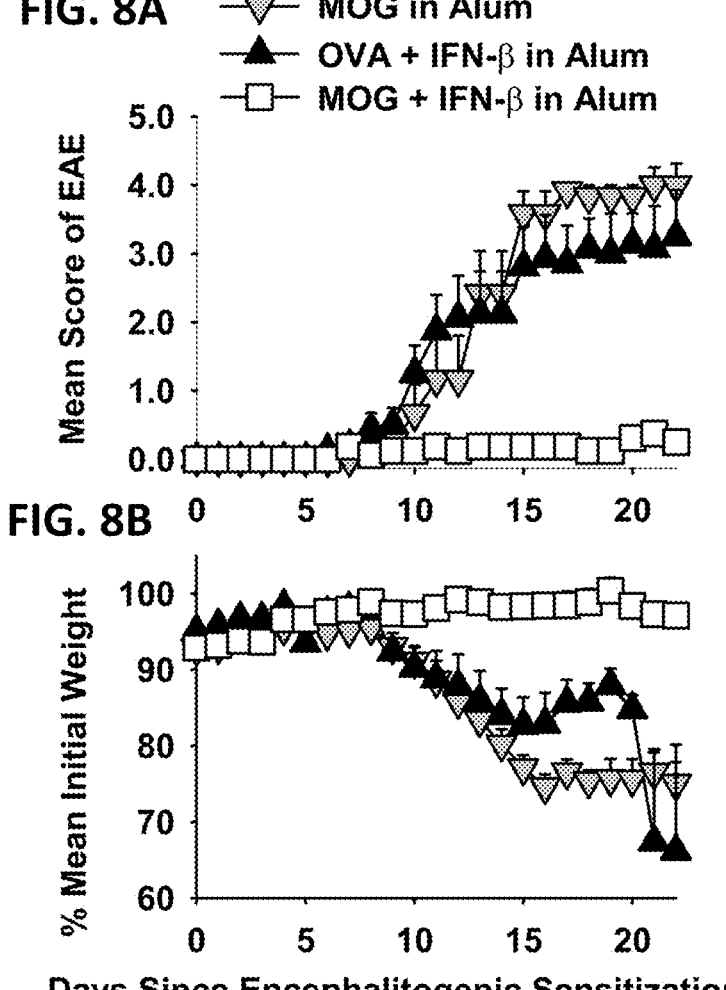

FIGS. 8A-8B. Pretreatment with the "IFN-β+MOG in Alum" vaccine inhibited the subsequent induction of EAE in MOG35-55 TCR transgenic mice. Vaccines comprised of "MOG35-55 in Alum", "IFN-β+OVA323-339 in Alum", or "IFN-β+MOG35-55 in Alum" were given on days −21, -14, and −7 to 2D2-FIG mice at dosages of 5 nmoles for both IFN-β and antigen. Mice were challenged with 100 μg MOG35-55 in CFA on day 0, were given Pertussis toxin on days 0 and 2. The timecourses for EAE (FIG. 8A) and body weight (FIG. 8B) are shown through day 22. Error bars represent standard error of the mean. The statistical analysis is given in Table 2.

Figures 9A, 9B, 9C, 9D:
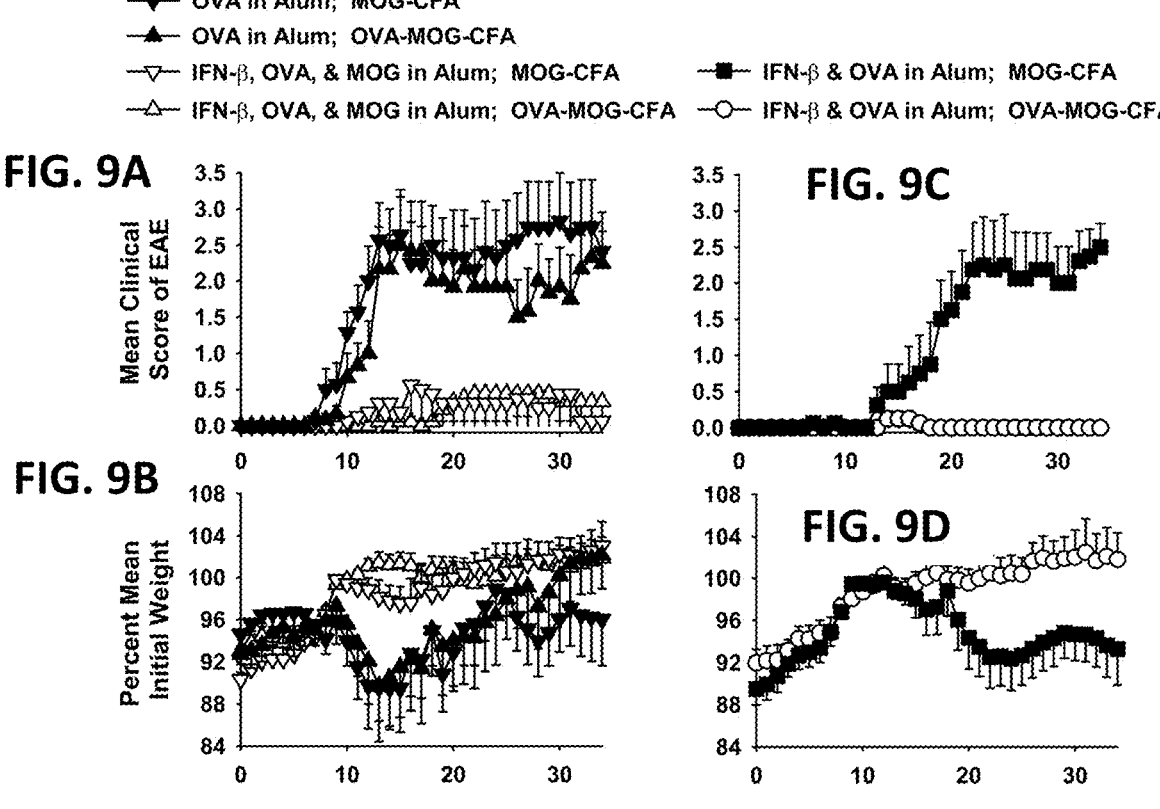

FIGS. 9A-9D. Does IFN-β adjuvant promote infectious tolerance? Mice were vaccinated once with three different vaccines including "IFN-β+OVA+MOG in Alum", "IFN-β+OVA in Alum", and "OVA in Alum" (5 nmole dose for all reagents) on day −8. Mice were challenged with two different emulsions to induce EAE, including "OVA+MOG in CFA" or "MOG in CFA" (100 μg dose for each peptide) on day 0. Pertussis toxin was given on days 0 and 2. Shown are the time course data through day 34 for EAE (FIGS. 9A, 9C) and weight loss (FIGS. 9B, 9D). Statistical analyses are given in Table 3.

Figures 10A, 10B, 10C, 10D, 10E:
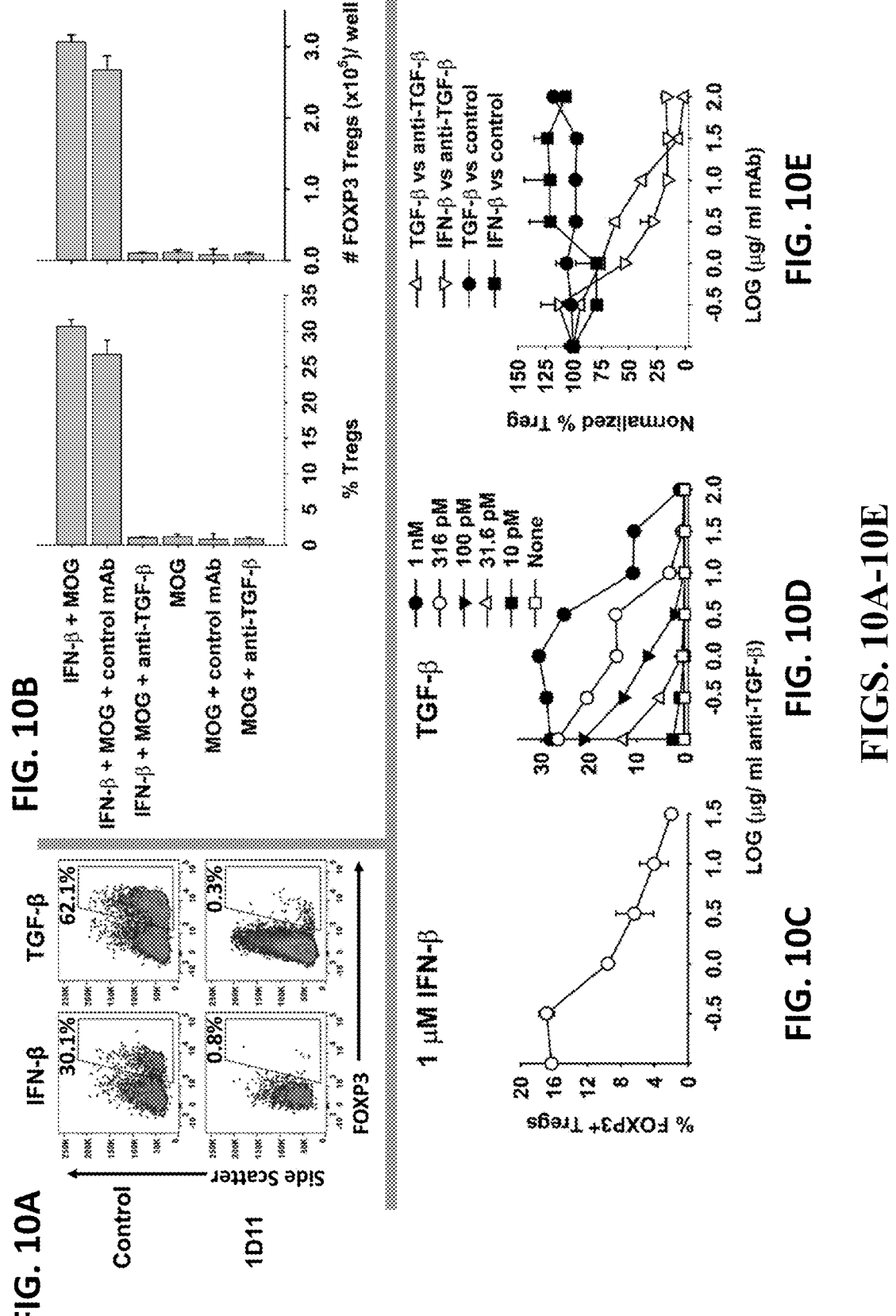

FIGS. 10A-10E. The anti-TGF-β mAb 1D11 inhibits IFN-β dependent induction of FOXP3$^+$ Tregs in vitro. (FIGS. 10A-10E) Naïve 2D2-FIG splenocytes (200,000/well) were cultured in triplicate with 1 μM MOG35-55 and either 1 μM IFN-β or 100 pM TGF-β (or as designated in FIG. 10D). Cultures also included either anti-mouse-TGF-β (1D11) or the isotype control mAb (LRTC 1) (31.6 μg/ml) (FIGS. 10A-10B) or as designated on the x-axis (FIGS. 10C-10E). After 7 days of culture, CD4$^+$ T cells were assessed for GFP expression. (FIG. 10A) Shown are representative dot plots of side scatter (y-axis) and FOXP3 expression (x-axis) together with (FIG. 10B) percentages and absolute numbers of FOXP3$^+$ Tregs after culture with MOG35-55 in the presence or absence of IFN-β and mAb. The quantitative neutralization profiles are shown for the anti-TGF-β 1D11 mAb in cultures of IFN-β-induced Tregs (FIG. 10C, 10E) and TGF-β-induced Tregs (FIG. 10D, 10E). Error bars represent standard error of the mean. These data are representative of three independent experiments.

Figures 11A, 11B, 11C, 11D, 11E:
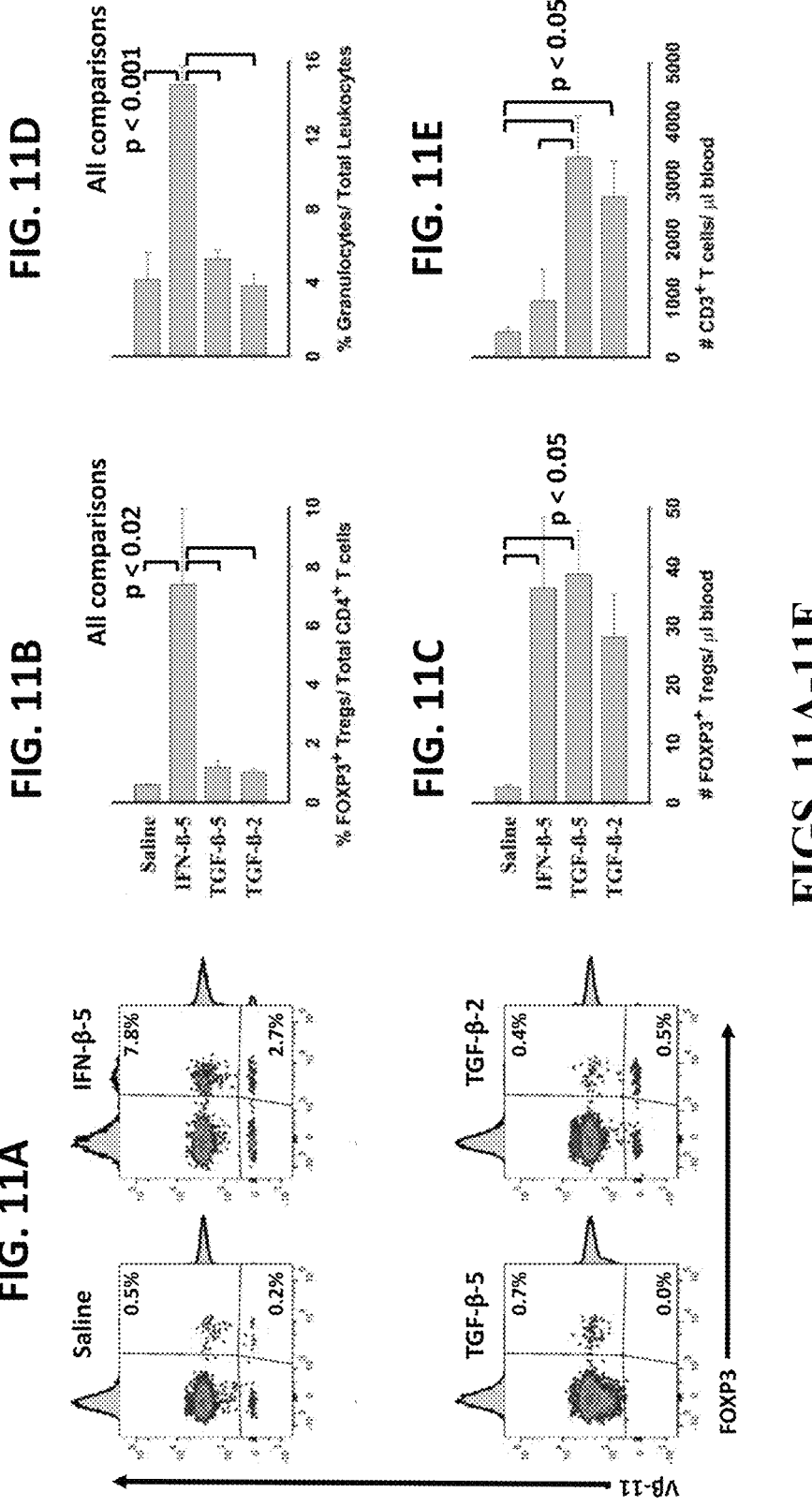

FIG. 11A-11E. When combined with Alum and MOG35-55, IFN-β uniquely increased the percentages of FOXP3$^+$ Tregs relative to the total pool of CD4$^+$ T cells. On day 0, 2D2-FIG mice (n=5) were injected with "Saline in Alum", "5 nmoles IFN-β+5 nmoles MOG35-55 in Alum" (IFN-β-5), "5 nmoles TGF-β+5 nmoles MOG35-55 in Alum" (TGF-β-5), or "2 nmoles TGF-β+5 nmoles MOG35-55 in Alum" (TGF-β-2). On day 13, PBMC were assessed for FOXP3$^+$ T cells as a percentage of the CD3$^+$ CD4$^+$ T cell population (FIGS. 11A-11B), the total numbers of FOXP3$^+$ Tregs per μl of blood (FIG. 11C), the percentages of granulocytes as a percentage of total leukocytes (FIG. 11D), and the total numbers of CD3$^+$ T cells per μl of blood (FIG. 11E). Analysis panels included CD3-BV421, CD4-PE, Vβ11-AF647, and CD45-BV785.

DETAILED DESCRIPTION

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods can be used for the production of viral and non-viral vectors, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, and other references mentioned herein are incorporated by reference in their entirety.

1. Definitions

As used herein, "a" or "an" or "the" can mean one or more than one. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

Moreover, the present invention also contemplates that in some embodiments of the invention, any feature or combination of features set forth herein can be excluded or omitted.

The term "modulate," "modulates" or "modulation" refers to enhancement (e.g., an increase) or inhibition (e.g., a reduction) in the specified activity.

The term "regulate" as used herein refers to the ability to affect a method, process, state of being, disorder or the like. The effect may be that of prevention, treatment or modulation.

By the terms "treat," "treating" or "treatment of," it is intended that the severity of the disorder or the symptoms of the disorder are reduced, or the disorder is partially or entirely eliminated, as compared to that which would occur in the absence of treatment. Treatment does not require the achievement of a complete cure of the disorder and can refer to stabilization of disease.

By the terms "preventing" or "prevention", it is intended that the inventive compounds, compositions and/or methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound (or composition which is used interchangeably unless otherwise specified or inappropriate for the circumstances) being administered.

As used herein, the administration of a compound "in conjunction with" or "in combination with" another compound means that the two compounds are administered closely enough in time that the presence of one alters the biological effects of the other. The two compounds may be administered in conjunction simultaneously (i.e., concurrently) or sequentially. Simultaneous administration may be carried out by mixing the compounds prior to administration and providing the same as a mixture, by administering the compounds at the same point in time but at different anatomic sites or using different routes of administration. Sequential administration can be carried out by administering one of the compounds prior to or before the other, and consequently, administering one of the compounds after the other.

"Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self tissues, innocuous foreign objects (e.g., dust mite or pollen allergens, etc.), or tissue transplants represent examples of adverse maladaptive immune responses.

The term "antigen" as used herein means a substance or compound that stimulates an immune response. Although usually a protein or polysaccharide, antigens may be any type of molecule, which can include small molecules (haptens) that are coupled to a carrier-protein.

The term "antigen presenting cells" or (APCs) refer to cells that mediate the cellular immune response by processing and/or presenting an antigen for recognition by certain lymphocytes such as T cells. Exemplary APCs include dendritic cells, macrophages, Langerhans cells and B cells.

As used herein, the term "autoimmune antigen" refers to any self protein or self component that serves either as a target or cause of an autoimmune disease. Examples of autoimmune antigens include, but are not limited to, myelin basic protein, proteolipid protein, or myelin oligodendrocyte protein (multiple sclerosis); peripheral myelin proteins P0 and P2 (Guillain-Barre syndrome); acetylcholine receptor (myasthenia gravis); cardiac myosin (rheumatic fever/myocarditis); proteins of the beta cells in the Isles of Langerhans-GAD (glutamic acid decarboxylase), insulin (Type I auto-immune diabetes mellitus), the thyroid-stimulating hormone receptor (Grave's disease), platelets (thrombocytopeni pur-pura), neuromuscular junction (myasthenia gravis), red blood cells (autoimmune hemolytic anemia and intracellular antigens (spliceosomes, ribosomes, nucleic acid, etc in sys-temic lupus erythematosus).

As used herein, the term "neuroantigen" (NAg) refers to a type of autoimmune antigen that is a nervous system protein (central or peripheral) including an auto-reactive epitope. The neuroantigen can be a myelin basic protein (MBP), a proteolipid protein (PLP), myelin oligodendrocyte glycoprotein (MOG), myelin-associated oligodendrocytic basic protein (MOG), or other nervous system-derived pro-teins or a portion thereof and further including those derived from any species, and in particular, human, rat, mouse, goat, and sheep.

By the term "immunogenic" it is meant any substance or compound that stimulates an immune response.

By the term "tolerogen" it is meant any substance that stimulates immunological tolerance. By the terms "tolero-genic" or "tolerogenic activity" it is meant that a response of immunological tolerance is induced by an antigen or anti-genic substance or an activity that results in the induction of immunological tolerance toward an antigen or antigenic substance.

The term "tolerance" as used herein refers to a decreased level of an immune response, a delay in the onset or progression of an immune response and/or a reduced risk of the onset or progression of an immune response. "Specific" immunological tolerance occurs when immunological toler-ance is preferentially invoked against certain antigens in comparison with others. "Active" immunological tolerance refers to a state in which the tolerance effect(s) are the result of an ongoing biological process: for example, down-regu-lation of specific effector cells by suppressor cells. "Sus-tained tolerance" is tolerance that measurably persists for an extended period of time.

The terms "adaptive immunity", "acquired immunity" or "immunological memory" are well-understood in the art and generally refer to the process of generating and maintaining specific cell memory after an initial response to a specific pathogen, and leads to an enhanced response to subsequent encounters with that pathogen. This process of acquired immunity is the basis of vaccination.

The terms "vaccination", "vaccine" or "immunization" are well-understood in the art. For example, the terms vaccination or immunization can be understood to be a process that increases a subject's immune reaction to antigen and therefore the ability to resist or overcome infection. In the case of the present invention, vaccination or immuniza-tion may decrease the recipient's immune response against self antigens thereby decreasing the likelihood of an auto-immune response.

The term "adjuvant" as used herein refers to a substance that can affect, i.e., enhance or increase, an immune response to an antigen.

"Polypeptide" as used herein, is used interchangeably with "protein," and refers to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly pro-duced, are isolated from an appropriate source, or are synthesized.

As used herein, a "functional" polypeptide is one that retains at least one biological activity normally associated with that polypeptide. Preferably, a "functional" polypeptide retains all of the activities possessed by the native, unmodi-fied or full-length peptide. By "retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native poly-peptide). A "non-functional" polypeptide is one that exhibits essentially no detectable biological activity normally asso-ciated with the polypeptide (e.g., at most, only an insignifi-cant amount, e.g., less than about 10% or even 5%).

"Fusion protein" as used herein, refers to a protein pro-duced when two heterologous nucleotide sequences or frag-ments thereof coding for two (or more) different polypep-tides, or fragments thereof, are fused together in the correct translational reading frame. The two or more different polypeptides, or fragments thereof, include those not found fused together in nature and/or include naturally occurring mutants. One or more of the fusion proteins of the present invention can display at least some cytokine biological activity.

As used herein, a "fragment" or "portion" is one that substantially retains at least one biological activity normally associated with that protein or polypeptide. In particular embodiments, the "fragment" or "portion" substantially retains all of the activities possessed by the native or unmodified protein. By "substantially retains" biological activity, it is meant that the fragment or portion retains at least about 50%, 60%, 75%, 85%, 90%, 95%, 97%, 98%, 99%, or more, of the biological activity of the native protein (and can even have a higher level of activity than the native protein). In some embodiments, a fragment or portion of the protein or polypeptide described herein is at least 4, 6, 8, 10, 15, 20, 30, 50, 75, 100, 150, 200 or more contiguous amino acids and/or less than about 200, 150, 100, 75, 50, 30, 20, 15 or 10 contiguous amino acids, including any combination of the foregoing as long as the lower limit is less than the upper limit and induces an immune response.

A "recombinant" nucleic acid is one that has been created using genetic engineering techniques.

A "recombinant polypeptide" is one that is produced from a recombinant nucleic acid.

As used herein, an "isolated" nucleic acid (e.g., an "iso-lated DNA" or an "isolated vector genome") means a nucleic acid separated or substantially free from at least some of the other components of the naturally occurring organism or virus, such as for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found asso-ciated with the polypeptide. As used herein, the "isolated" polypeptide is at least about 25%, 50%, 60%, 70%, 75%, 80%, 85%, 90%, 95%, 97%, 98%, 99% or more pure (w/w).

A "heterologous nucleotide sequence" will typically be a sequence that is not naturally-occurring in the vector. Alter-natively, a heterologous nucleotide sequence can refer to a sequence that is placed into a non-naturally occurring envi-ronment (e.g., by association with a promoter with which it is not naturally associated; in a cell that does not contain an endogenous form of the heterologous nucleotide sequence and/or under the direction of a promoter and/or other regulatory elements with which it is not normally associate, in a cell that does contain an endogenous form of the heterologous nucleotide sequence.).

There are no particular limits to the size of the heterologous nucleic acid. In particular embodiments, the heterologous nucleic acid is at least about 15, 18, 24, 50, 100, 250, 500, 1000, 1500, 2000, 3000, 4000 or more nucleotides long and/or less than about 4000, 3000, 2000, 1500, 1000, 500, 250 or 100 nucleotides long.

As used herein, a "vector" or "delivery vector" can be a viral or non-viral vector that is used to deliver a nucleic acid to a cell, tissue or subject. Exemplary vectors include, but are not limited to, adeno-associated virus vectors, adenovirus vectors, lentivirus vectors, paramyxovirus vectors, alphavirus vectors and herpes virus vectors.

A "recombinant" vector or delivery vector refers to a viral or non-viral vector that comprises one or more heterologous nucleotide sequences (i.e., transgenes), e.g., two, three, four, five or more heterologous nucleotide sequences. In an embodiment of the invention, the recombinant vectors and delivery vectors of the invention encode a fusion polypeptide of NAg and a cytokine such as IFN-β, but can also include one or more additional heterologous nucleotide sequences, for example, sequences encoding C- or N-terminal modifications and linker moieties.

As used herein, the term "viral vector" or "viral delivery vector" can refer to a virus particle that functions as a nucleic acid delivery vehicle, and which comprises the vector genome packaged within a virion. Alternatively, these terms can be used to refer to the vector genome when used as a nucleic acid delivery vehicle in the absence of the virion.

A viral "vector genome" refers to the viral genomic DNA or RNA, in either its naturally occurring or modified form. A "recombinant vector genome" is a viral genome (e.g., vDNA) that comprises one or more heterologous nucleotide sequence(s).

As used herein, the term "host cell" comprises prokaryotic cells and eukaryotic cells. Exemplary prokaryotic host cells include *E. coli, Bacillus subtilis*, etc. Exemplary eukaryotic cells include yeast cells, insect cells, mammal cells, etc.

2. Active Agents

Embodiments of the present invention provide compositions comprising, consisting essentially of or consisting of (a) an autoimmune antigen; (b) an anti-inflammatory cytokine; and (c) an aluminum-based carrier. The autoimmune antigen may be myelin basic protein (MBP), proteolipid protein (PLP), myelin oligodendrocyte glycoprotein (MOG), myelin-associated oligodendrocytic basic protein and cardiac myosin, or portions thereof. Moreover, the autoimmune antigen may be an encephalitogenic determinant portion of an autoimmune antigen selected from the group consisting of myelin basic protein (MBP), proteolipid protein (PLP), myelin oligodendrocyte glycoprotein (MOG), myelin-associated oligodendrocytic basic protein and cardiac myosin, or portions thereof.

In some embodiments, the anti-inflammatory cytokine is an interleukin or interleukin receptor antagonist. The "anti-inflammatory" cytokine, which can also be referred to as an "immunoregulatory" cytokine is a naturally occurring or recombinant protein, analog thereof or fragment thereof that elicits an anti-inflammatory response in a cell that has a receptor for that cytokine. Cytokines of the present invention can include interleukin receptor antagonists from any species including murine and human such as IL-1-RA. Cytokines of the present invention can further include interleukins from any species including murine and human such as IL-1, IL-2, IL-3, IL-4, IL-5, IL-6, IL-7, IL-10, IL-12, IL-13, IL-14, IL-15, IL-16, IL-17 and IL-18, IL-19, IL-20, IL-21, IL-22, IL-23, IL-24, IL-25, IL-26, IL-27, IL-28A, IL-28B, IL-29, IL-31, IL-32, and IL-33, hematopoietic factors such as macrophage colony-stimulating factor (M-CSF), granulocyte-macrophage colony stimulating factor (GM-CSF), granulocyte colony stimulating factor (G-CSF) and erythropoietin, tumor necrosis factors (TNF) such as TNF-α and TGF-β, lymphokines such as lymphotoxin, regulators of metabolic processes such as leptin, interferons such as type I interferons, IFN-α, IFN-β, and IFN-γ and chemokines.

In particular embodiments, use of individual moieties can be used together in a combination therapy. In particular embodiments, the autoimmune antigen and the anti-inflammatory cytokine are physically linked to form a fusion protein in an aluminum-based carrier. "Alum" or aluminum-based carriers or "adjuvants" are non-crystalline gels based on aluminum oxy-hydroxide (referred to as aluminum hydroxide gel) [Reed S, Bertholet S, Coler R N et al. New horizons in adjuvants for vaccine development. *Trends Immunol* 2009, 30 (1): 23-32; Brewer JM. (How) do aluminum adjuvants work? *Immunol Letters* 2006, 102:10-15. Vaccine protein antigens are adsorbed onto preformed aluminum hydroxide (AH) or alhydrogel (chemically crystalline aluminum oxyhydroxide), aluminum phosphate (AP), or adju-phos gels (chemically amorphous aluminum hydroxyphosphate). In some embodiments, the alum adjuvant may be aluminum hydroxide or aluminum phosphate. In some embodiments, the alum adjuvant may include a formulation including a mixture of aluminum hydroxide and magnesium hydroxide. In some embodiments, the alum binds to both the anti-inflammatory cytokine and the autoimmune antigen, for example, immunomodulatory IFN-β and myelin neuroantigen peptides to form noncovalent indirect connections between IFN-β and a neuroantigen.

It will be appreciated by those skilled in the art that there can be variability in the nucleic acids that encode the fusion polypeptides of the present invention due to the degeneracy of the genetic code. The degeneracy of the genetic code, which allows different nucleic acid sequences to code for the same polypeptide, is well known in the literature (see table below).

Further variation in the nucleic acid sequence can be introduced by the presence (or absence) of non-translated sequences, such as intronic sequences and 5' and 3' untranslated sequences.

Moreover, the isolated nucleic acids of the invention encompass those nucleic acids encoding fusion proteins that have at least about 60%, 70%, 80%, 90%, 95%, 97%, 98% or higher amino acid sequence similarity with the polypeptide sequences specifically disclosed herein or to those known sequences corresponding to proteins included in aspects of the present invention (or fragments thereof) and further encode functional fusion proteins as defined herein.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981), *Adv. Appl. Math.* 2, 482, by the sequence identity alignment algorithm of Needleman & Wunsch (1970), *J. Mol. Biol.* 48, 443, by the search for similarity method of Pearson & Lipman (1988), *Proc. Natl. Acad. Sci. USA* 85, 2444, by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al. (1984), *Nucl. Acid Res.* 12, 387-395, preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, (1987) *J. Mol. Evol.* 35, 351-360; the method is similar to that described by Higgins & Sharp (1989), *CABIOS* 5, 151-153.

Another example of a useful algorithm is the BLAST algorithm, described in Altschul et al. (1990), *J. Mol. Biol.* 215, 403-410, and Karlin et al. (1993), *Proc. Natl. Acad. Sci. USA* 90, 5873-5787. A particularly useful BLAST program is the WU-BLAST-2 program which was obtained from Altschul et al. (1996), *Methods in Enzymology,* 266, 460-480; blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., (1997) *Nucleic Acids Res.* 25, 3389-3402.

A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

To modify the amino acid sequences of the fusion proteins of the present invention, amino acid substitutions can be based on any characteristic known in the art, including the relative similarity or differences of the amino acid side-chain substituents, for example, their hydrophobicity, hydrophilicity, charge, size, and the like. In particular embodiments, substitutions (i.e., substitution with an amino acid residue having similar properties) are made in the amino acid sequence encoding a fusion protein or polypeptide used in the invention.

In making amino acid substitutions, the hydropathic index of amino acids can be considered. The importance of the hydropathic amino acid index in conferring interactive biologic function on a protein is generally understood in the art (see, Kyte and Doolittle (1982), *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further comprise modified nucleotides or nucleotide analogs.

The isolated nucleic acids encoding the polypeptides of the invention can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metalothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

Methods of making fusion proteins are well understood in the art. Methods of making fusion proteins include those in accordance with U.S. Pat. Nos. 4,701,416; 5,496,924; 5,521,288; 5,837,816; 5,981,221; 5,994,104; 6,109,885; 6,211,342; 6,211,427; 6,369,199; 6,482,409; 6,555,342; 6,972,322; 6,987,006 7,087,411 and 7,112,659 and WO 2008/130382, which are incorporated herein by reference in their entirety. Such methods include growing a host cell including a vector that includes nucleic acids encoding the fusion protein under conditions appropriate for expression and subsequent isolation of the fusion protein.

In particular embodiments, an isolated nucleic acid may be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide of the invention or active fragment thereof operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, *Gene Expression Technology*: Methods in Enzymology 185, Academic Press, San Diego, Calif. (1990). Examples of vectors for expression in yeast *S. cerevisiae* include pYepSec1 (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen™, San Diego, Calif.). Baculovirus vectors available for expression of nucleic acids to produce proteins in cultured insect cells (e.g., Sf 9 cells) include the Bac-to-Bac® Baculovirus Expression System from Invitrogen.

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector and/or may comprise another heterologous sequence of interest.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

3. Methods of Use

Embodiments of the present invention include methods of modulating an immunological disorder or immune response comprising, consisting essentially of or consisting of administering to a subject or a cell an effective amount of an autoimmune antigen and an anti-inflammatory cytokine in an aluminum-based adjuvant. The autoimmune antigen may be myelin basic protein (MBP), proteolipid protein (PLP), myelin oligodendrocyte glycoprotein (MOG), myelin-associated oligodendrocytic basic protein and cardiac myosin, or portions thereof. In some embodiments, the autoimmune antigen is an encephalitogenic determinant portion of an autoimmune antigen selected from the group consisting of myelin basic protein (MBP), proteolipid protein (PLP), myelin oligodendrocyte glycoprotein (MOG), myelin-associated oligodendrocytic basic protein and cardiac myosin, or portions thereof. In some embodiments, the encephalitogenic determinant portion of the MBP, PLP, MOG, myelin-associated oligodendrocytic basic protein or cardiac myosin is (1) an amino acid sequence encoded by a nucleic acid sequence encoding an encephalitogenic determinant portion of the MBP, PLP, MOG, myelin-associated oligodendrocytic basic protein or cardiac myosin, or (2) an amino acid sequence encoded by a nucleic acid sequence that hydridizes with the complement of the nucleic acid sequence of (1) under stringent conditions as represented by hybridization conditions of 0.5M $NaHPO_4$, 7% sodium dodecyl sulfate (SDS), 1 mM EDTA at 65° C. and wash conditions of 0.1×SSC/0.1% SDS at 68° C.

In some embodiments, the anti-inflammatory cytokine is an interleukin or interleukin receptor antagonist. The anti-inflammatory cytokine may be IL-1, IL-2, IL-3, IL-4, IL-5, IL-6, IL-7, IL-10, IL-12, IL-13, IL-14, IL-15, IL-16, IL-17 and IL-18, IL-19, IL-20, IL-21, IL-22, IL-23, IL-24, IL-25, IL-26, IL-27, IL-28A, IL-28B, IL-29, IL-31, IL-32, IL-33, macrophage colony-stimulating factor (M-CSF), granulocyte-macrophage colony stimulating factor (GM-CSF), granulocyte colony stimulating factor (G-CSF), erythropoietin, TNF-α, TGF-β, lymphotoxin, leptin, IFN-α, IFN-β, IFN-γ or a chemokine.

According to some embodiments, the immunological disorder is an autoimmune disease, an allergic or hypersensitivity disease, a transplantation and/or tissue disorder or combinations thereof.

Autoimmune diseases include, but are not limited to, those affecting biological systems such as the circulatory system, digestive system, endocrine system, integumentary system, lymphatic system, muscular system, nervous system, reproductive system, respiratory system, skeletal system or urinary system. In particular, the biological systems can include the Nervous system: Acute disseminated encephalomyelitis (demyelinating inflammation following vaccination or infection); Myasthenia Gravis (anti-AchR antibodies, blockade of neuromuscular junction); Multiple sclerosis (inflammation of CNS myelin); Acute inflammatory demyelinating polyneuropathy/Guillain-Barre syndrome (inflammation of peripheral myelin); Endocrine system: Hashimoto's Thyroiditis (anti-thyroid antibodies, hypothyroidism); Grave's Disease (auto-antibodies stimulate TSH receptors on thyroid follicular cells, hyperthyroidism); Insulin-Dependent Diabetes Mellitus (i.e. juvenile diabetes, inflammation and deletion of β islet cells); Autoimmune adrenal insufficiency (e.g., Addison's disease, inflammation coupled with progressive scarring and atrophy of adrenal glands); Autoimmune oophoritis (inflammation of ovaries, infertility); Autoimmune orchitis (inflammation of testis); Hematopoietic system: Autoimmune hemolytic anemia (anti-erythrocyte antibodies); Paroxysmal cold hemoglobinuria (mediated by IgM cold agglutinins against erythrocytes); Idiopathic thrombocytopenia purpura (anti-platelet antibodies, bleeding); Autoimmune neutropenia (antibodies against neutrophils cause degranulation, neutrophil depletion, and vasculitis); Pernicious anemia (progressive destruction of gastric fundic gland, loss of intrinsic factor, and malabsorption of vitamin $B_{12}$); Autoimmune coagulopathy (circulating anti-coagulants, anti-phospholipid antibody syndrome, neutralizes phospholipids necessary for clotting activity); Gastrointestinal Tract: Primary biliary cirrhosis (intrahepatic bile duct and portal inflammation leading to fibrosis and cirrhosis); Inflammatory bowel disease (Crohn's disease, ulcerative colitis); Kidney: Glomerulonephritis (antibody against glomerular basement membrane); Immune complex glomerular nephritis (accumulation of deposited immune complexes in basement membrane); Skin: Pemphigus vulgaris (loss of adhesion between epidermal cells, blistering, antibody against stratified squamous epithelium); Systemic autoimmune disease: Systemic Lupus Erythematosus (arthralgias, rash, nephritis, anti-nuclear antibodies); Rheumatoid Arthritis (inflammatory polyarticular arthritis, rheumatoid factor); Sjogren's syndrome (inflammation of lacrymal and parotid glands with arthritis); Polymyositis (inflammation of skeletal muscle); Dermatomyositis (inflammation of skin and skeletal muscle); Scleroderma (progressive systemic sclerosis, sclerosis of skin and internal organs); and Cardiac and vascular diseases: Autoimmune myocarditis (inflammation of cardiac muscle); Immune complex-mediated vasculitis (passive deposition of immune complexes in vessel walls followed by C-mediated lysis and inflammation); Polyarteritis nodosa (type of necrotizing vasculitis that follows certain types of infections). In some embodiments of the present invention, the autoimmune disease is an autoimmune disease affecting the nervous system, endocrine system, hematopoietic system, gastrointestinal tract, renal system, cardiac system, vascular system, musculoskeletal system or a combination thereof. In some embodiments, the autoimmune disease is a systemic autoimmune disease. In particular embodiments, the autoimmune disease is multiple sclerosis.

Allergic or hypersensitivity diseases include, but are not limited to, allergic rhinitis, asthma, atopic dermatitis, allergic gastroenteropathy, contact dermatitis, drug allergy or a combination thereof. In particular embodiments, the present invention provides active agents, compositions and methods to induce antigen-specific immunological tolerance to allergens responsible for the allergic diseases described herein.

Transplant rejection and tissue disorders include, but are not limited to, those affecting the appendix, bladder, brain, ear, esophagus, eye, gall bladder, heart, kidney, large intestine, liver, lung, mouth, muscle, nose, ovary, pancreas, parathyroid gland, pineal gland, pituitary gland, skin, small intestine, spleen, stomach, testes, thymus, thyroid gland, trachea, uterus, vermiform appendix or combinations thereof. In particular embodiments, the present invention provides compositions and methods to induce antigen-specific immunological tolerance to allogeneic and xenogeneic transplantation antigens that may contribute to the rejection of tissue transplants, and thus, facilitate acceptance of kidney transplants, liver transplants, pancreas transplants, skin grafts, heart transplants, and heart-lung transplant or other organs listed above. The active agents and methods may also alleviate complications of bone marrow transplantation (i.e., graft versus host disease).

Embodiments of the present invention also provide methods of preventing or treating multiple sclerosis comprising, consisting essentially of or consisting of administering NAg and IFN-β in an aluminum-based adjuvant and/or NAg and GMCSF in an aluminum-based adjuvant. Embodiments of the present invention also provide methods of modulating antigen-presenting cell function comprising, consisting essentially of or consisting of exposing an antigen-presenting cell to a combination comprising, consisting essentially of or consisting of an autoimmune antigen and an anti-inflammatory cytokine in an aluminum-based adjuvant. Methods of the present invention further contemplate use of a composition comprising, consisting essentially of or consisting of (a) an autoimmune antigen; (b) an anti-inflammatory cytokine; and (c) an aluminum-based adjuvant for preparation of a medicament for the prevention and/or treatment of an immunological disorder.

However, it is also contemplated that diseases and/or disorders treated by the methods of this invention can include any disease or disorder that can be treated by mounting an effective tolerogenic. Accordingly, embodiments of the present invention provide methods of modulating an immune response including administering a composition of matter as described herein in an amount sufficient to elicit a tolerogenic response. In some embodiments, the immune response is antigen-specific. In some embodiments, the administering step is carried out in vivo or ex vivo. In still other embodiments, the tolerogenic response is an active tolerance mechanism. In particular embodiments, the tolerogenic response is a sustained tolerogenic response. In some embodiments, the tolerogenic response is an antigen-specific tolerogenic response without inhibition of adaptive immunity.

It is also contemplated that the compositions of matter of this invention can be used as a vaccine or prophylactic composition and further employed in methods of preventing a disease or disorder in a subject, comprising administering to the subject an effective amount of an active agent of this invention. The vaccine or prophylactic composition can be administered to a subject who is identified to be at risk of contracting a particular disease or developing a particular disorder and in whom the ability to elicit an immune response to an antigen may be impaired. Identification of a subject at risk can include, for example, evaluation of such factors as family history, genetic predisposition, age, environmental exposure, occupation, lifestyle and the like, as are well known in the art.

The effective dosage of any specific active agent will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, administration to a subject such as a human, a dosage of from about 0.01, 0.1, or 1 mg/kg up to 50, 100, or 150 mg/kg or more for each active agent can be employed. Depending on the solubility of the particular formulation of active agents administered, the daily dose can be divided among one or several unit dose administrations.

4. Formulations and Administration

In terms of administration, the most suitable route in any given case will depend on the nature and severity of the condition being treated and on the combination of components being administered.

The compositions of matter described herein can be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the compositions of matter is typically admixed with, inter alia, an acceptable carrier. The carrier can be a solid or a liquid, or both, and is optionally formulated as a unit-dose formulation, which can be prepared by any of the well-known techniques of pharmacy.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like.

In the case of a solution, it can be lyophilized to a powder and then reconstituted immediately prior to use. For dispersions and suspensions, appropriate carriers and additives include aqueous gums, celluloses, silicates or oils.

For injection, the carrier is typically a liquid, such as sterile pyrogen-free water, pyrogen-free phosphate-buffered saline solution, bacteriostatic water, or Cremophor EL[R] (BASF, Parsippany, N.J.), parenterally acceptable oil including polyethylene glycol, polyvinyl pyrrolidone, lecithin, *arachis* oil or sesame oil, with other additives for aiding solubility or preservation may also be included. For other methods of administration, the carrier can be either solid or liquid.

For oral administration, the composition of matter composition can be administered in solid dosage forms, such as capsules, tablets, and powders, or in liquid dosage forms, such as elixirs, syrups, and suspensions. The composition of matter can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges including the compositions of matter in a flavored base, usually sucrose and acacia or tragacanth; and pastilles including the fusion protein, compositions, viral vector or nucleic acid in an inert base such as gelatin and glycerin or sucrose and acacia.

Formulations of the present invention suitable for parenteral administration can include sterile aqueous and non-aqueous injection solutions of the compositions of matter, which preparations are generally isotonic with the blood of the intended recipient. These preparations can contain antioxidants, buffers, bacteriostats and solutes, which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition including a composition of matter of the invention, in a unit dosage form in a sealed container. Optionally, the active agents are provided in the form of a lyophilizate, which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the compositions of matter with one or more conventional excipients or carriers, for example, cocoa butter, polyethylene glycol or a suppository wax, which are solid at room temperature, but liquid at body temperature and therefore melt in the rectum or vaginal cavity and release the compositions of matter.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution. Suitable formulations comprise citrate or bis\tris buffer (pH 6) or ethanol/water.

The composition, fusion protein, viral vector or nucleic acid described herein can be formulated for nasal administration or otherwise administered to the lungs of a subject by any suitable means, for example, by an aerosol suspension of respirable particles including the compositions of matter, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles including the compositions of matter can likewise be produced with any solid particulate medicament aerosol generator, by techniques known in the pharmaceutical art.

Alternatively, one can administer the compositions of matter in a local rather than systemic manner, for example, in a depot or sustained-release formulation.

In particular embodiments of the invention, administration is by subcutaneous or intradermal administration. Subcutaneous and intradermal administration can be by any method known in the art including, but not limited to, injection, gene gun, powderject device, bioject device, microenhancer array, microneedles, and scarification (i.e., abrading the surface and then applying a solution including the compositions of matter).

In other embodiments, composition of matter is administered intramuscularly, for example, by intramuscular injection or by local administration.

Nucleic acids (e.g., DNA and/or RNA) can also be delivered in association with liposomes, such as lecithin liposomes or other liposomes known in the art (for example, as described in WO 93/24640) and may further be associated with an adjuvant. Liposomes including cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. PCT publication WO 94/27435 describes compositions for genetic immunization including cationic lipids and polynucleotides. Agents that assist in the cellular uptake of nucleic acid, such as calcium ions, viral proteins and other transfection facilitating agents, may be included.

Polynucleotide immunogenic preparations may also be formulated as microcapsules, including biodegradable time-release particles. U.S. Pat. No. 5,151,264 describes a particulate carrier of phospholipid/glycolipid/polysaccharide nature that has been termed Bio Vecteurs Supra Moleculaires (BVSM).

In particular embodiments, the mode of administration is parenteral for the methods employing the use of the autoimmune antigen or portion thereof in combination with the autoimmune cytokine, each as described herein, where these moieties do not comprise a fusion protein.

Methods of the present invention further include administering an effective amount of the active agents of the present invention, as described above, to the subject. The effective amount of the active agent, the use of which is in the scope of the present invention, will vary somewhat from subject to subject, and will depend upon factors such as the age and condition of the subject and the route of delivery. Such dosages can be determined in accordance with routine pharmacological procedures known to those skilled in the art. For example, the active agents of the present invention can be administered to the subject in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the composition. In some embodiments, the active agents include from about 0.05 to about 95% by weight of the composition. In other embodiments, the active agents include from about 0.05 to about 60% by weight of the composition. In still other embodiments, the active agents include from about 0.05 to about 10% by weight of the composition.

In particular embodiments of the present invention, the composition described herein is immunogenic, and the administration of the active agents can be carried out therapeutically (i.e., as a rescue treatment) or prophylactically.

For example, in some embodiments, to protect against an autoimmune disease, subjects may be vaccinated in anticipation of antigen exposure, as neonates or adolescents. Subjects who have not previously been exposed to the disease may also be vaccinated. Moreover, subjects afflicted with an autoimmune disease may be administered the immunogenic composition during a period of remission in order to prevent a relapse of the disease. The immunogenic composition of the present invention can be given as a single dose schedule or in a multiple dose schedule. A multiple dose schedule is one in which a primary course of administration may consist of about 1 to 10 separate doses, followed by other doses (i.e., booster doses) given at subsequent time intervals to maintain and/or reinforce the immune response, for example, at about 1 to 4 months for a second dose, and if needed, a subsequent dose(s) after another several months. The dosage regimen will also, at least in part, be determined by the need of the individual and be dependent upon the judgment of the medical or veterinary practitioner.

Embodiments of the present further provide kits comprising one or more containers having pharmaceutical dosage units including an effective amount of the compositions and/or components of the compositions described herein, wherein the container is packaged with optional instructions for the use thereof.

As described in further detail below, the present invention finds use in both veterinary, medical and research applications. Suitable subjects according to the present invention include any subject in whom regulating an immunological response or treating or preventing an immunological disorder is desired or needed, as well as any subject prone to such conditions and/or disorders. In some embodiments, the subject is a human; however, a subject of this invention can include an animal subject, particularly mammalian subjects such as canines, felines, bovines, caprines, equines, ovines, porcines, rodents (e.g., rats and mice), lagomorphs, primates (including non-human primates), etc., including domesticated animals, companion animals and wild animals for veterinary medicine or treatment or pharmaceutical drug development purposes.

The subjects relevant to this invention may be male or female and may be any species and of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric.

Having now described the invention, the same will be illustrated with reference to certain examples, which are included herein for illustration purposes only, and which are not intended to be limiting of the invention.

EXAMPLES

Example 1

Materials and Methods

Animals and Reagents.

B6 mice, Foxp3-IRES-GFP knock-in (FIG) mice (B6.Cg-Foxp3$^{tm2Tch}$/J, Stock Number 006772), and MOG35-55 specific TCR transgenic 2D2 mice (B6-Tg(Tcra2D2, Tcrb2D2) 1Kuch/J) (Stock Number 006912) were obtained from the Jackson Laboratory (Bar Harbor, ME) and were housed and bred in the Department of Comparative Medicine at East Carolina University Brody School of Medicine. 2D2-FIG mice were obtained through intercross breeding. 2D2 mice have a myelin oligodendrocyte glycoprotein (MOG)-specific, self-reactive T cell repertoire. Routine screening of 2D2 mice was performed by FACS analysis of PBMC by use of antibodies specific for TCR Vβ11 and/or Vα3.2. The FIG genotype was screened by use of forward (CAC CTA TGC CAC CCT TAT CC) (SEQ ID NO:1) and reverse (ATT GTG GGT CAA GGG GAA G) (SEQ ID NO:2) primers. The FIG knock-in product was 390 base-pairs, and the wt product was 341 base-pairs. Animal care and use was performed in accordance with approved animal use protocols and guidelines of the East Carolina University Institutional Animal Care and Use Committee.

Antigens and IFNβ-NAg Fusion Proteins.

Synthetic MOG35-55 (M-E-V-G-W-Y-R-S-P-F-S-R-V-V-H-L-Y-R-N-G-K) (SEQ ID NO:3) or PLP178-191 (N-T-W-T-T-C-Q-S-I-A-F-P-S-K) (SEQ ID NO:4) was obtained from Genscript (Piscataway, NJ). The initial preparation of recombinant TGFβ1 used in this project was a generous gift from Dr. Peter Sun (NIH). Subsequently, a rat TGFβ1 sequence was cloned into the pIRES2-AcGFP1 vector (Clontech, Mountain View, CA) and expressed via stable transfection of human embryonic kidney (HEK) cells. TGFβ1 was designed as described (45). This expression vector encoded a rat serum albumin leader sequence, an 8-histidine purification tag, the latency-associated peptide (LAP), the native RHRR cleavage site, and the C-terminal TGF-β1 sequence. A C32S substitution in the LAP domain enabled high level expression. The protein was expressed in HEK supernatants, purified on Ni-NTA affinity columns, and was activated by 10 minutes of exposure to 70° C. The quantitative bioactivity of each TGF-β1 preparation was verified by induction of FOXP3 in cultures of MOG-stimulated 2D2-FIG splenocytes.

Derivation, expression, purification, and bioassay of the murine cytokine-NAg fusion proteins were described in previous studies (38, 42). Murine IFN-β and the N-terminal domain of IFNβ-MOG are comprised of the murine IFN-β sequence (accession number NP_034640) except that a non-native alanine residue was added as the second amino acid to encode an optimal Kozak translation-initiation site (GCCGCCACC-ATG-GCC-) (SEQ ID NO:5). The C-terminus of the IFNβ-MOG fusion protein included an enterokinase linker cleavage site, the MOG35-55 sequence, and an 8-histidine affinity chromatography purification tag. IFN-β also had a C-terminal enterokinase linker and an 8-histidine purification tag. Expression supernatants were concentrated on YM10 ultrafiltration membranes and were directly applied to consecutive Ni-NTA Agarose columns (Qiagen, Chatsworth, CA) followed by extensive washing of the resin (50 mM NaH$_2$PO$_4$, 500 mM NaCl, 10 mM imidazole, pH 8.0). IFNβ-MOG or IFN-β was eluted by acid elution (pH 4.0) or with 250 mM imidazole (pH 8.0) and was concentrated and diafiltrated in Amicon Ultra-15 centrifugal filter devices (EMD Millipore, Billerica, MA). Protein quantity was assessed by absorbance at 280 nm, and purity was assessed by SDS-PAGE. The bioactivities of murine IFN-β recombinant proteins were confirmed in vitro by inhibition of IL-2 dependent T cell proliferation as shown by inhibitory constants ($K_i$/IC$_{50}$) in the low picomolar range (i.e., half-maximal inhibition in the 1-10 pM range) and by induction of FOXP3$^+$ T cells in cultures of MOG-stimulated 2D2-FIG splenocytes.

Generation, Purification, and Administration of mAb.

The PC61-5.3 anti-CD25 rat IgG1 (A) hybridoma (46), the Y13-259 anti-v-H-Ras rat IgG1 (K) hybridoma (47), and the 1D11.16.8 anti-mouse-TGF-β1/2/3 mouse IgG1 hybridoma (48, 49) were obtained from ATCC and were subcloned twice to ensure stability. The LRTC1 anti-rat LFA-1 mouse IgG1 hybridoma was originally derived in our laboratory (50-52) and had no crossreactivity with mouse LFA-1. PC61 and Y13 were used as sources of CD25$^+$ Treg depleting mAb and the isotype control mAb, respectively. 1D11 and LRTC1 were used as sources of anti-TGF-β mAb and the isotype control mAb, respectively. For all 4 hybridomas, cells were cultured in supplemented DMEM in C2011 hollow fiber cartridges (FiberCell Systems, Inc., Frederick, MD). Hybridoma supernatants were clarified at 7,200×g, precipitated with 50% ammonium sulfate, and dissolved in PBS. MAb preparations were purified on protein G agarose columns. Antibody was eluted with 200 mM glycine at pH 3.0 and immediately neutralized by 1M Tris buffer of pH 9.0. The purity of these mAb was verified by SDS-PAGE. Specific activities of all PC61 preparations were determined by staining of murine CD25$^+$ T cells with serial ½ log dilutions of the mAb. After washing, PC61-stained T cells were labeled with a PE-conjugated goat anti-rat IgG(H+L) secondary antibody followed by flow cytometric analysis. As designated for pretreatment experiments, purified mAb were administered i.p. at a dose of 250 μg/injection to mice on days −5 and −3 (or days −4 and −2) unless designated otherwise. Depletion of specific lymphoid subsets was confirmed by flow cytometric analysis of PBMC on days −1 or 0. Active immunization with MOG35-55 in CFA was initiated on day 0.

Flow Cytometric Analyses of Splenocytes and PBMC.

Cells were washed in HBSS with 2% heat-inactivated FBS and stained with designated cocktails of fluorochrome-conjugated antibodies for 1 hr at 4° C. in the dark. After staining PBMC, erythrocytes were lysed with 1:10 HBSS for 20 seconds at 4° C. followed by addition of 2×PBS. Cells were then washed 3 times with HBSS/2% FBS. Data were collected by use of a Becton-Dickinson LSRII flow cytometer (San Jose, CA) and analyzed by use of FlowJo software. In designated experiments, reference 'counting' beads were added to samples immediately before flow cytometric analysis (AccuCheck Counting Beads, Life Technologies, Frederick, MD or APC-conjugated CaliBRITE™ beads, BD Biosciences). The use of reference beads enabled comparisons of cell yield or absolute cell numbers. Pairwise comparisons were analyzed by two-tailed t-tests for data that passed Normality (Shapiro-Wilk) and Equal Variance (Brown-Forsythe) Tests. Otherwise, data were assessed with a Mann-Whitney Rank Sum Test. Fluorochrome-conjugated mAb were obtained from BioLegend or BD Biosciences and included CD19 (6D5), CD25 (PC61 or 3C7), CD28 (E18), CD3 (17A2 or 145-2C11), CD4 (GK1.5), CD44 (IM7), CD45 (30-F11), CD5 (53-7.3), CD69 (H1.2F3), CD8 (53-6.7), CD80 (16-10A1), CD86 (GL-1), CTLA-4 (UC10-4B9), GARP (F011-5), I-Ab (AF6-120.1), IFNAR-1 (MAR1-5A3), Ly-6G (Gr1) (1A8), PD1 (CD279) (29F.1A12), PDL1 (CD274) (10F.9G2), PDL2 (CD273) (TY25), TCR-Vα3.2 (RR3-16), TCR-Vβ11 (KT11). Multicolor panels were designed in the figure legends.

Preparation of Tolerogenic Vaccines.

A phosphate buffered saline solution was prepared that contained designated doses of IFN-β, TGF-β, or peptide NAg. Aluminum Hydroxide Gel colloidal suspension (A8222 Alum, Sigma Aldrich or Alhydrogel adjuvant #vac-alu-250, Invivogen) was mixed thoroughly. Equal volumes of Alum and a solution containing IFN-β and NAg were combined for a total injection volume of 100 μl per mouse. IFN-β and NAg were given in matched equimolar doses (e.g., a 2 nmole vaccine dose included 2 nmoles IFN-β and 2 nmoles NAg, or a 5 nmole vaccine dose included 5 nmoles IFN-β and 5 nmoles NAg) unless designated otherwise. The mixture was incubated for 1 hr on ice with continuous agitation to allow the protein/peptide attachment to the Alum gel precipitate. The vaccine was administered subcutaneously by two injections of 50 µl each. No signs of inflammation were noted at the injection site.

Induction and Assessment of EAE.

CFA (Incomplete Freund's Adjuvant with 4 mg/ml heat-killed *Mycobacterium tuberculosis* H37Ra, BD Biosciences, Franklin Lakes, NJ) was mixed 1:1 with MOG35-55 or PLP178-191 in phosphate-buffered saline. The CFA/antigen mixture was emulsified by sonication. EAE was elicited in B6 mice by injection of 200 µg MOG35-55 or PLP178-191 in a total volume of 100 µl emulsion via three subcutaneous injections of 33 µl across the lower back. Each mouse received separate injections (200 nanograms i.p.) of Pertussis toxin on days 0 and 2. All immunizations were performed under isoflurane anesthesia (Abbott Laboratories, Chicago, IL). Mice were assessed daily for clinical score and body weight. The following scale was used to score the clinical signs of EAE: 0, no disease; 0.5, partial paralysis of tail without ataxia; 1.0, flaccid paralysis of tail or ataxia but not both; 2.0, flaccid paralysis of tail with ataxia or impaired righting reflex; 3.0, partial hind limb paralysis marked by inability to walk upright but with ambulatory rhythm in both legs; 3.5, same as above but with full paralysis of one leg; 4.0, full hindlimb paralysis; 5.0, total hindlimb paralysis with forelimb involvement or moribund. A score of 5.0 was a humane endpoint for euthanasia.

The incidence of EAE reflected the number of mice afflicted with EAE compared to the total group size. Cumulative EAE scores were calculated by summing daily scores for each mouse across the designated time course of disease. Maximal scores were calculated as the most severe EAE score for each mouse. Mice that did not exhibit EAE had a score of zero for the cumulative and maximal scores, and these scores were included in the group average. Attrition reflected the number of mice that reached clinical endpoints (e.g., score of 5.0). Mice that exhibited humane endpoints as assessed by body weight loss, body score, or clinical score of 5.0 were subjected to humane euthanasia and were omitted from scoring thereafter. Thus, groups of mice exhibiting substantial attrition had artificially depressed mean cumulative scores, but attrition did not affect mean maximal scores. Time-course graphs portrayed daily mean maximal scores. Cumulative and maximal EAE scores were converted to ranked scores and analyzed by nonparametric ANOVA. To calculate percent maximal weight loss, 100% body weight was assigned as the maximal body weight obtained from day 1 through day 10, and daily body weights were calculated for each day after normalization to this 100% value. The minimum body weight was defined as the lowest body weight after normalization to the 100% value during the span of day 11 until the end of the experiment. Maximal weight loss was calculated by subtraction of the normalized minimum value from the 100% value. Negative weight loss values represented weight gain. Weight loss was analyzed by parametric ANOVA. Nonparametric and parametric ANOVA were assessed with a Bonferroni Post Hoc test unless noted otherwise. Incidence of EAE was analyzed pair-wise by Fisher's Exact Test. Mean EAE and weight loss data were shown with the standard error of the mean.

Example 2

Figures 1A, 1B, 1C, 1D, 1E, 1F:
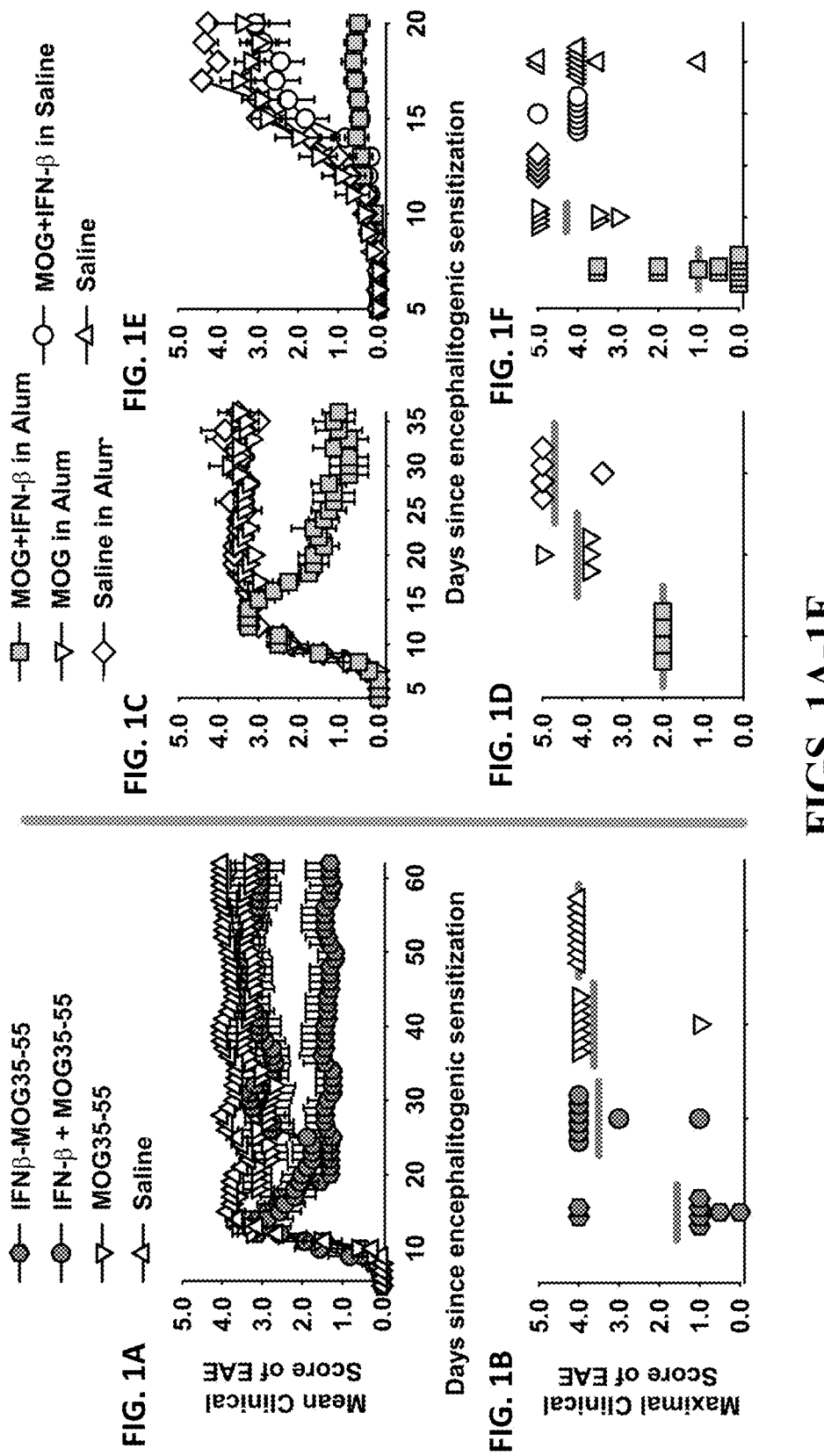
FIGS. 1A-1F. IFN-β is a tolerogenic vaccine adjuvant in EAE. EAE was induced in all B6 mice on day 0 by injection of 200 μg of MOG35-55 in CFA with i.p. injections of Pertussis toxin on days 0 and 2. Shown are EAE timecourses (FIG. 1A, FIG. 1C, FIG. 1E) and density dotplots (FIG. 1B, FIG. 1D, FIG. 1F) for treatment (FIGS. 1A-1D) and pre-treatment experiments (FIGS. 1E-1F).

Vaccination with an IFNβ-NAg Fusion Protein was a Therapeutic Intervention In EAE Previous studies revealed that covalent linkage of murine IFN-β and PLP139-151 was involved in tolerance induction in the SJL relapsing remitting model of EAE (38). To assess the generality of these findings, experiments were performed to assess whether covalent linkage was needed for tolerance induction in the B6 model of chronic EAE (FIGS. 1A-1B). A treatment model in B6 mice was chosen because chronic EAE in this model is typically resistant to antigen-specific interventions. To address the requirement of cytokine-NAg covalent linkage, B6 mice were immunized to elicit paralytic EAE on day 0 (FIGS. 1A-1B and Table 1). On day 13, mice were matched for severity of EAE and were treated with 2 nmoles of murine IFNβ-MOG fusion protein, a mixture of IFN-β and MOG, MOG alone, or saline. Treatments were given in saline on day 13, and again on days 15 and 17 with a final treatment on day 19. Mice treated with either the IFNβ-MOG fusion protein or the combination of "IFN-β and MOG35-55" in saline exhibited a partial recovery marked by a nadir in paralytic signs from days 22-24 (FIG. 1A). Mice treated with IFNβ-MOG remained stable with mild EAE thereafter and did not relapse whereas mice treated with the combination of IFN-β and MOG relapsed by day 30 and exhibited severe paralytic EAE during the remainder of the experiment. Mice treated with MOG35-55 or saline exhibited a sustained course of paralytic EAE. These data revealed that the covalent linkage of IFN-β and MOG35-55 is a significant factor in the prolonged beneficial activity of IFNβ-MOG in the B6 model of EAE.

Example 3

IFN-β+MOG in Alum" was Therapeutic and Tolerogenic in EAE

Given that physical linkage is needed for optimal tolerogenic activity, we predicted that such linkage could be non-covalent and indirect rather than covalent and direct. The prediction was that IFN-β and NAg peptides would be bound, immobilized, and crosslinked by the Alum adjuvant matrix and thereby achieve the requisite linkage needed for IFN-β mediated tolerogenic activity. To test this prediction, vaccines including "IFN-β+MOG35-55 in Alum", "MOG35-55 in Alum", and "Saline in Alum" were administered once after onset of paralytic EAE on day 15 in groups that had been matched for mean cumulative and maximal disease scores (FIGS. 1C-1D and Table 1). A single administration of "5 nmoles IFN-β+5 nmoles MOG35-55 in Alum" reversed the course of paralytic EAE, facilitated clinical recovery, and ameliorated EAE-associated weight loss. The vaccines "MOG35-55 in Alum", and "Saline in Alum" had no effect in that the respective mice continued to exhibit severe paralytic EAE throughout the experiment and several mice progressed to a score of 5.0 (humane endpoint, Table 1). These data indicated that the "IFN-β+MOG35-55 in Alum" vaccine had robust efficacy as a therapeutic intervention.

Treatment regimens are used to measure the clinically-significant modality of therapeutic efficacy. Conversely, pretreatment regimens are used to measure tolerogenic activity because vaccine-mediated inhibitory activity must be remembered by the immune system to impact a subsequent encephalitogenic challenge. To test pretreatment efficacy, the "IFN-β+MOG35-55 in Alum" vaccine along with control vaccine formulations were administered at a dose of 2 nmoles on days −21, −14, and −7 followed by an encephalitogenic challenge on day 0 (FIGS. 1E-1F and Table 1). The "IFN-β+MOG35-55 in Alum" vaccine attenuated the subsequent induction of EAE whereas vaccines comprised of "MOG in Alum", "Saline in Alum", "MOG+IFN-β in saline", or saline had no impact on the course of severe chronic EAE. The EAE timecourse is shown through day 20 and not beyond due to attrition of mice that reached a score of 5.0 in the four control groups (Table 1). These data support the hypothesis that NAg in the context of an "IFN-β in Alum" adjuvant specifies a strong NAg-specific tolerogenic response.

Example 4

Figures 2C, 2D:
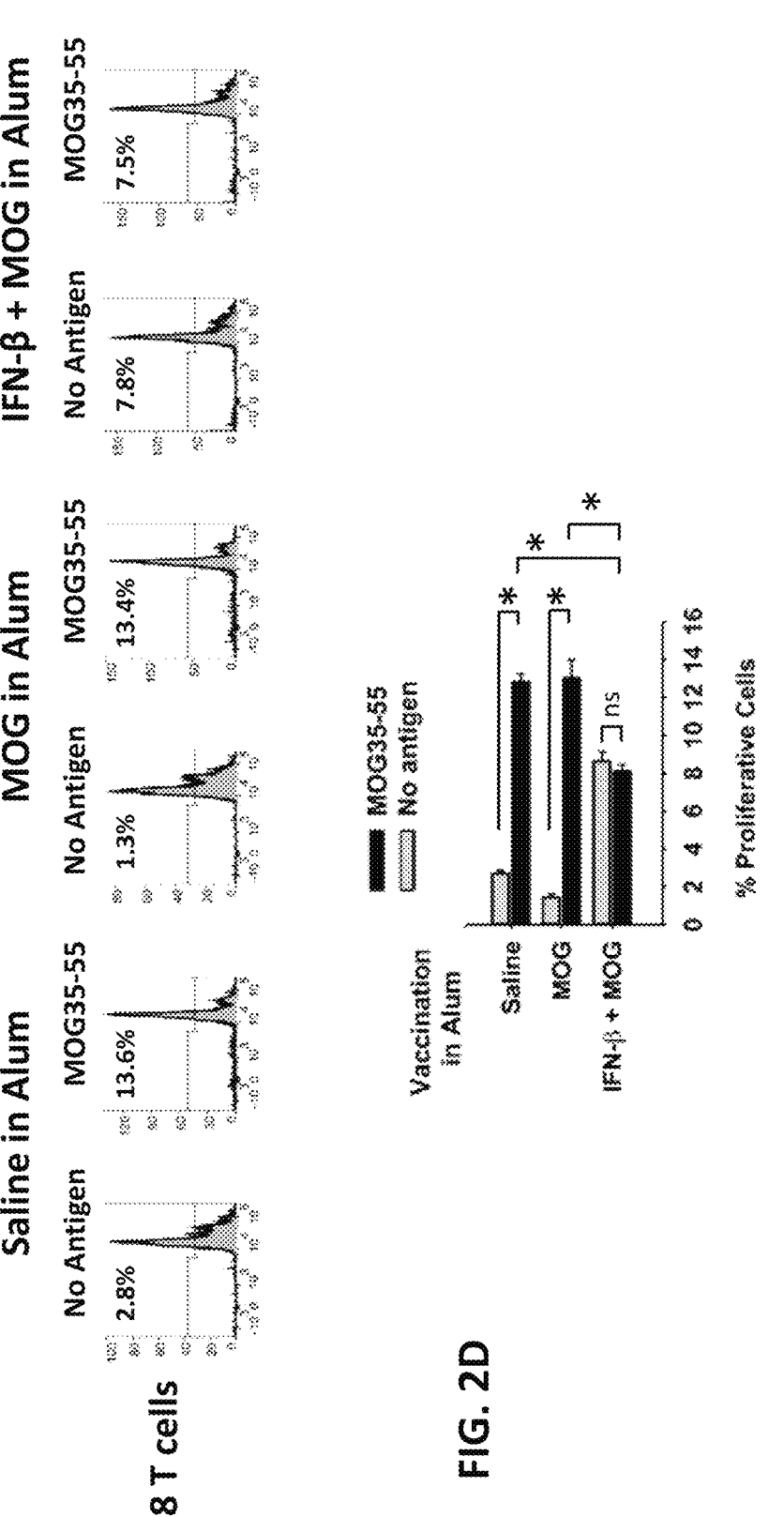

Pretreatment with the IFN-β+MOG in Alum Vaccine Altered MOG-Specific Sensitization in MOG/CFA Sensitized Mice To address whether this vaccine approach modulated MOG/CFA-induced sensitization, B6 mice were vaccinated with 5 nmoles of "IFN-β+MOG in Alum", "MOG in Alum", or "saline in Alum" on day −7 and were immunized with 200 μg MOG in CFA on day 0. After 13 days, draining lymph node cells were labeled with CTV and were cultured with or without 1 μM MOG35-55 for 4 days. Lymph node cells from mice vaccinated with either "MOG in Alum", or "saline in Alum" exhibited robust, MOG-specific proliferative responses. Responsive cell types included CD4$^+$ T cells (FIGS. 2A-2B), CD8$^+$ T cells (FIGS. 2C-2D), and B cells (FIGS. 2E-2F). In contrast, mice vaccinated with "IFN-β+ MOG in Alum" did not exhibit MOG-specific responses and instead exhibited proliferative responses that were 'autologous' (i.e., independent of exogenous MOG35-55). Mice vaccinated with "IFN-β+MOG in Alum" lacked MOG-specific proliferative responses and instead exhibited autologous proliferative responses when assayed 10 or 18 days after MOG/CFA sensitization (data not shown). These data indicate that the IFN-β adjuvant qualitatively alters MOG-specific sensitization in the draining lymph nodes.

Example 5

Depletion of CD25$^+$ Tregs Impairs Tolerogenic Vaccination

Figures 3A, 3B, 3C, 3D:
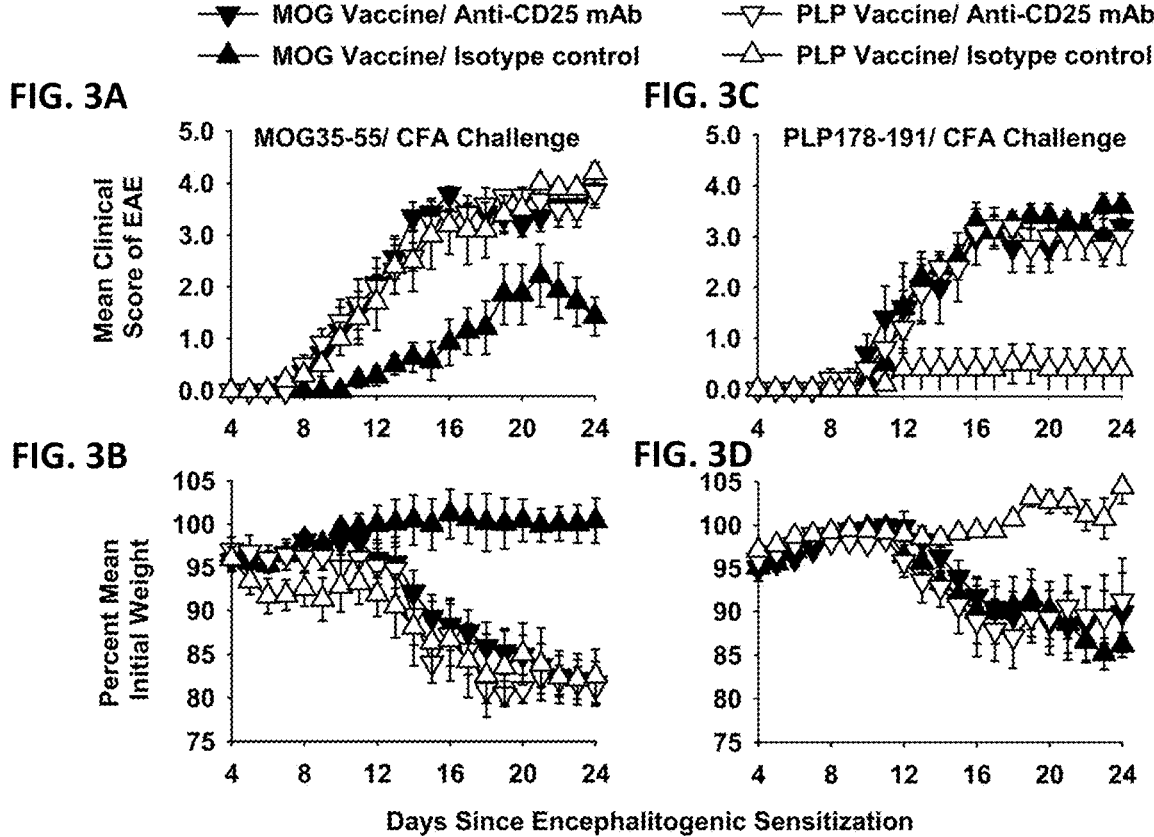
FIGS. 3A-3D. Depletion of CD25$^+$ Tregs reversed the suppressive action of tolerogenic vaccination. B6 mice were vaccinated with two different tolerogenic vaccines (2 nmoles IFN-β/MOG35-55/Alum and IFN-β/PLP178-191/Alum) on days −21, −14, and −7. Mice were treated or not with the anti-CD25 PC61 mAb (250 μg i.p.) on days −4 and −2 and then were challenged to induce EAE on days 0 and 2. Shown are the timecourse data through day 25 for EAE (FIGS. 3A and 3C) and weight loss (FIGS. 3B and 3D). Tabular data and statistical analysis are shown in Table 1.

Vaccine-induced tolerogenic memory, as shown in FIG. 1, suggested the potential involvement of MOG-specific CD25$^+$ Tregs as an underlying mechanism. To test this possibility, B6 mice were vaccinated with two distinct vaccines ("IFN-β+MOG35-55 in Alum" versus "IFN-β+ PLP178-191 in Alum") on days −21, −14, and −7 (FIGS. 3A-3D and Table 1). Vaccines were administered subcutaneously at a dose of 2 nmoles (FIGS. 3A-3B) or 5 nmoles (FIGS. 3C-3D). Mice were treated with the anti-CD25 PC61 mAb (rat IgG1, 250 μg i.p.) or an isotype control (Y13-259 rat IgG1) on days −4 and −2 to deplete CD25$^+$ Tregs. These mice were then subjected to induction of EAE with MOG35-55/CFA (FIGS. 3A-3B) or PLP178-191/CFA (FIGS. 3C-3D) on day 0. The results showed that tolerogenic vaccination was NAg-specific. The MOG-specific vaccine inhibited MOG-induced EAE but lacked suppressive activity in PLP/CFA-challenged mice. Vice versa, the PLP-specific vaccine inhibited PLP-induced EAE but lacked suppressive activity in MOG/CFA-challenged mice. Pretreatment with the anti-CD25 PC61 mAb but not the isotype control antibody eliminated circulating CD25$^+$ Tregs (data not shown). Pretreatment with the anti-CD25 PC61 mAb reversed the suppressive action of the respective tolerogenic vaccine such that the PC61-treated mice showed a chronic course of paralytic EAE (FIGS. 3A, 3C) and weight loss (FIGS. 3B, 3D) equivalent to those of the control groups. That is, PC61 pre-treatment restored full EAE susceptibility in MOG-vaccinated mice challenged with MOG/CFA. Likewise, PC61 pre-treatment restored full EAE susceptibility in PLP-vaccinated mice challenged with PLP/CFA. Notably, PC61-mediated depletion of Tregs had no impact on EAE in groups not subjected to NAg-specific tolerance induction. In conclusion, these data indicate that "IFN-β+NAg in Alum" tolerogenic vaccination elicited CD25$^+$ NAg-specific Tregs that inhibited EAE via a mechanism of active NAg-specific tolerance.

Example 6

IFN-β and MOG Elicited FOXP3 Expression In Vitro

PC61-mediated reversal of tolerance suggested that IFN-β may support induction of CD25$^+$ FOXP3$^+$ Treg cells. Hence, "2D2-FIG" mice were used to test whether IFN-β induced FOXP3 during T cell antigen recognition of MOG35-55 in vitro (FIG. 4A). 2D2-FIG mice have a transgenic T cell repertoire specific for MOG35-55 and express a GFP reporter of FOXP3 expression. Naïve 2D2-FIG splenic T cells were cultured in duplicate for 7 days with or without 1 μM MOG35-55 in the presence or absence of 1 μM IFN-β. TGF-β (1 nM) was used as a positive control for the antigen-dependent induction of FOXP3. IFN-β (1 μM) elicited FOXP3 expression in approximately 30-40% of all 2D2-FIG T cells in the presence of MOG35-55. Induction of FOXP3 was NAg-dependent because only 1-2% of T cells expressed FOXP3 in the absence of MOG35-55 despite the presence or absence of IFN-β, TGF-β, or both cytokines. These data showed that IFN-β facilitated induction of FOXP3 in MOG-stimulated naïve T cells. Given that Alum was absent from this in vitro system, one can conclude that IFN-β has Treg biasing activities that are independent from Alum.

Figure 4A:
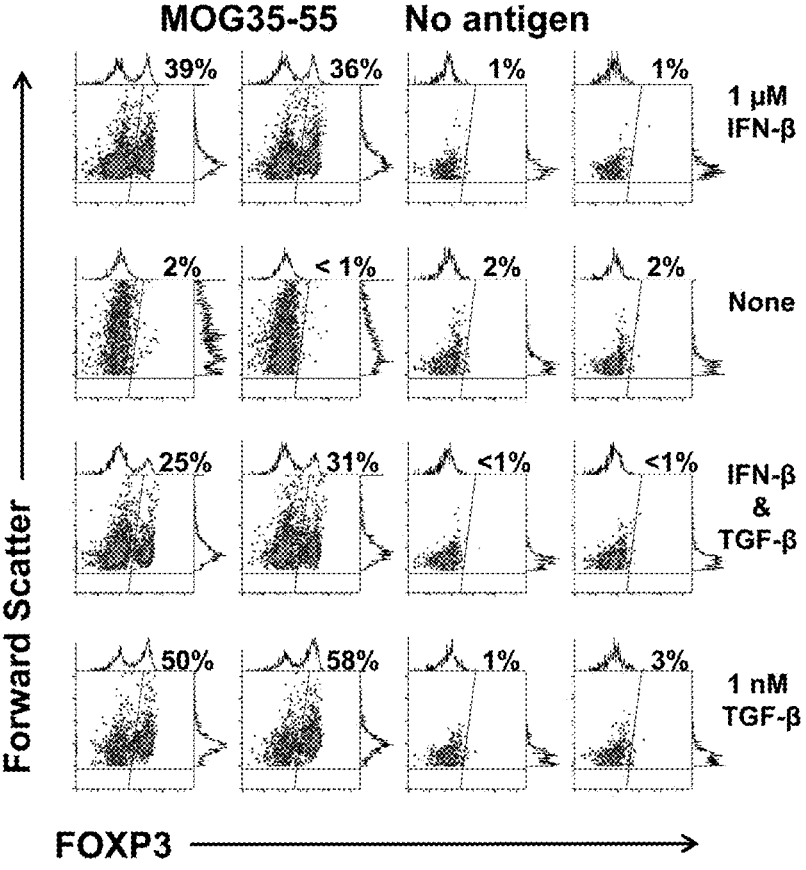
FIGS. 4A-4D. IFN-β elicited MOG-dependent induction of FOXP3 in naïve 2D2-FIG T cells.
Figures 4B, 4C, 4D:
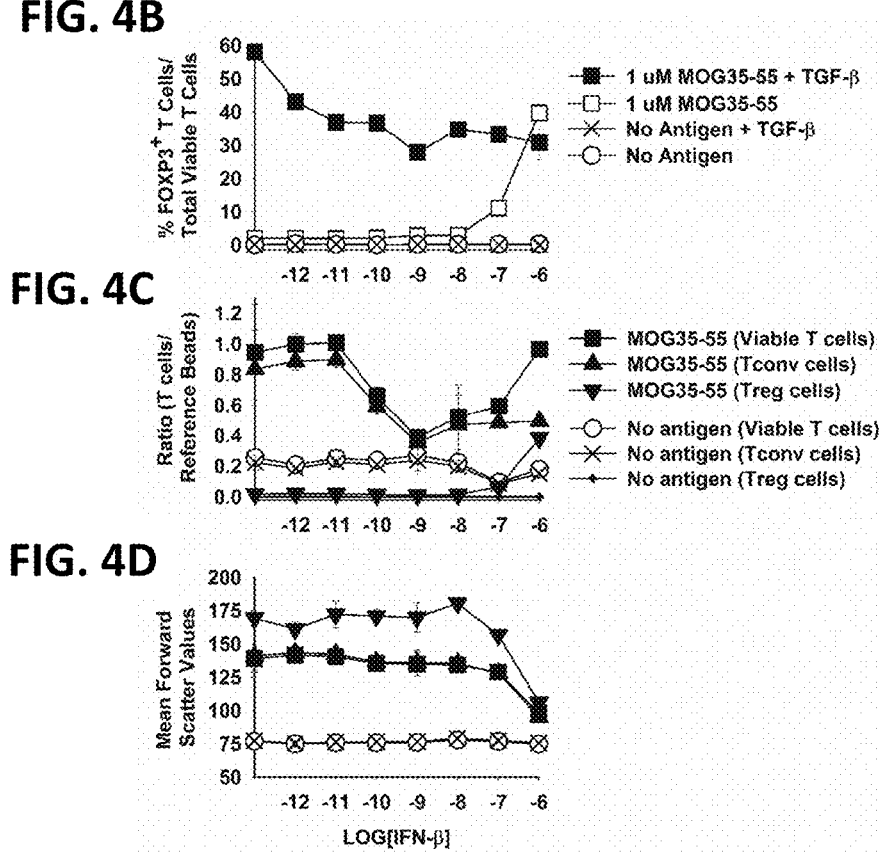

The ability of IFN-β to induce FOXP3 (30-40% FOXP3$^+$ Tregs) however was less than that achieved with TGF-β (50-60% FOXP3$^+$ Tregs) (FIGS. 4A-4B). IFN-β and TGF-β were not synergistic or additive. Rather, the interaction was non-additive or antagonistic in that the induction of FOXP3 by TGF-β was reduced in the presence of IFN-β to that observed in cultures with IFN-β alone (FIG. 4B). To standardize culture-to-culture comparisons, 50,000 fluorochrome-conjugated reference CaliBRITE™ beads (BD Biosciences) were added to each well to enable assessment of T cell numbers relative to control numbers of reference beads (FIG. 4C). In the absence of IFN-β, activation of T cells with MOG35-55 increased T cell numbers by approximately 4-fold. IFN-β concentrations in the range of 10 pM to 1 nM progressively reduced T cell numbers consistent with the known pro-apoptotic action of this cytokine. However, the number of viable T cells increased in the range of 1 nM to 1 μM IFN-β to the maximal levels obtained in activation cultures without IFN-β, giving the appearance of a U-shaped concentration curve (FIG. 4C, MOG35-55 Viable T cells). This paradoxical increase in T cell numbers at high IFN-β concentrations was driven by selective increases in the percentages of FOXP3$^+$ Treg cells rather than FOXP3$^{null}$ conventional T cells. Indeed, frequencies of conventional T cells remained essentially equal in the high IFN-β concentration range. The FOXP3$^+$ T cell population had higher levels of CD25 (data not shown) and size (mean forward scatter values, FIG. 4D) than conventional T cells or total viable T cells. However, at high concentrations of IFN-β (100 nM to 1 μM), the size of FOXP3$^+$ Tregs decreased and were comparable with that of conventional T cells. Overall, these data provided evidence that high IFN-β concentrations (100 nM to 1 μM) selectively favored the emergence of a FOXP3$^+$ Treg subset.

Example 7

Function and Phenotype of IFN-β Induced Tregs

Figures 5A, 5B:
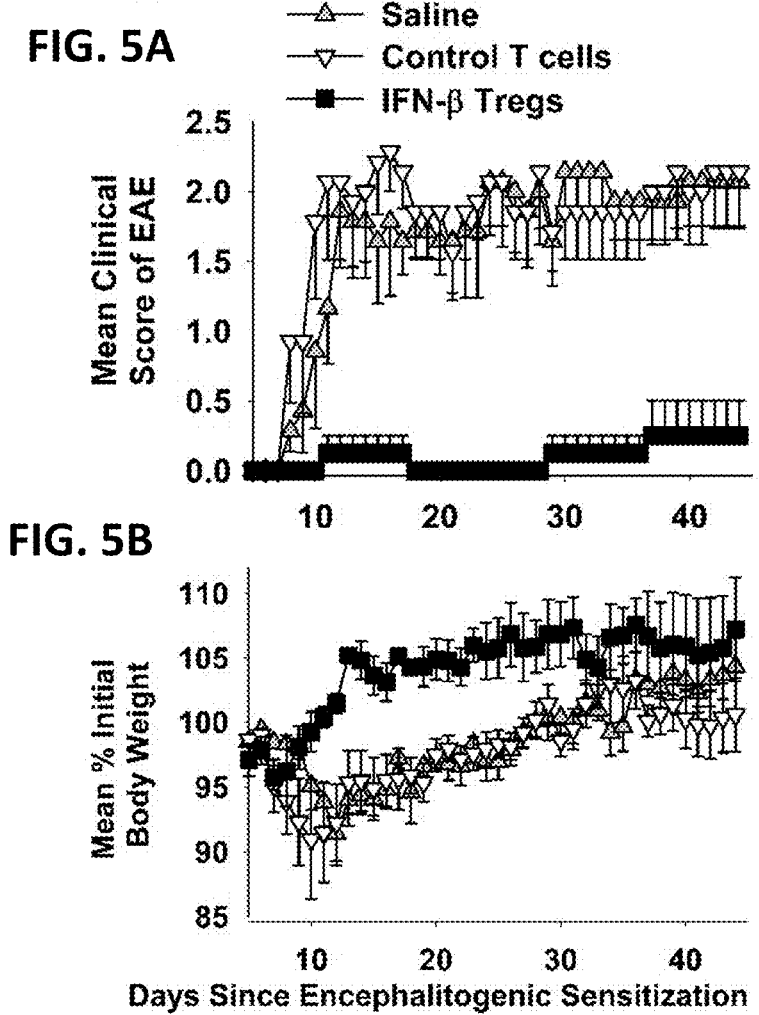
FIGS. 5A-5F. Function and phenotype of IFN-β-induced Tregs.
Figure 5C:
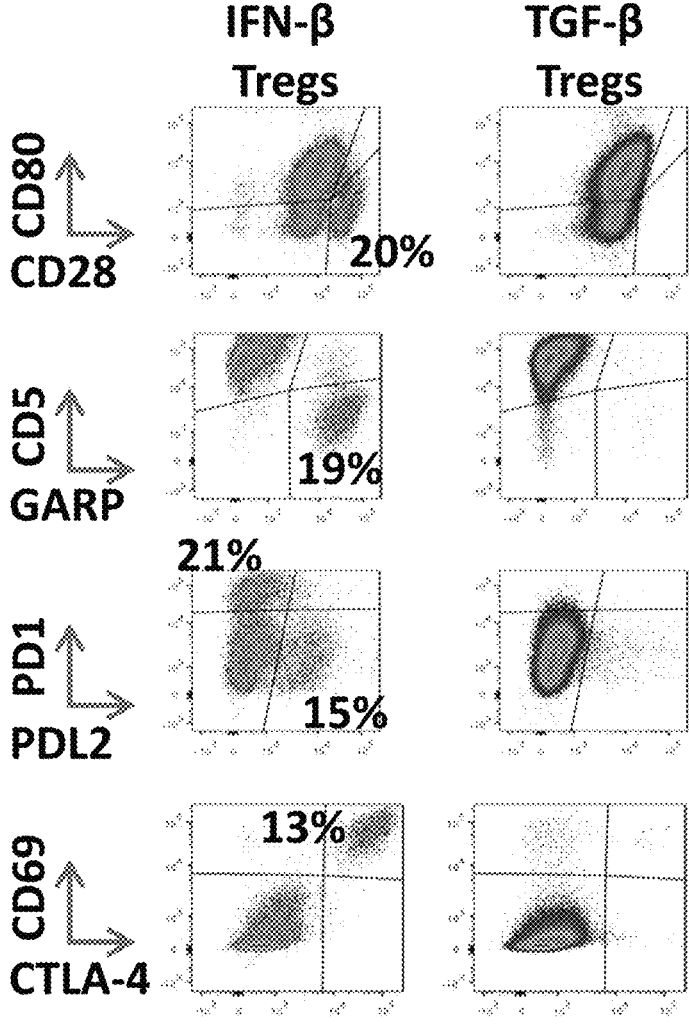
Figures 5D, 5E, 5F:
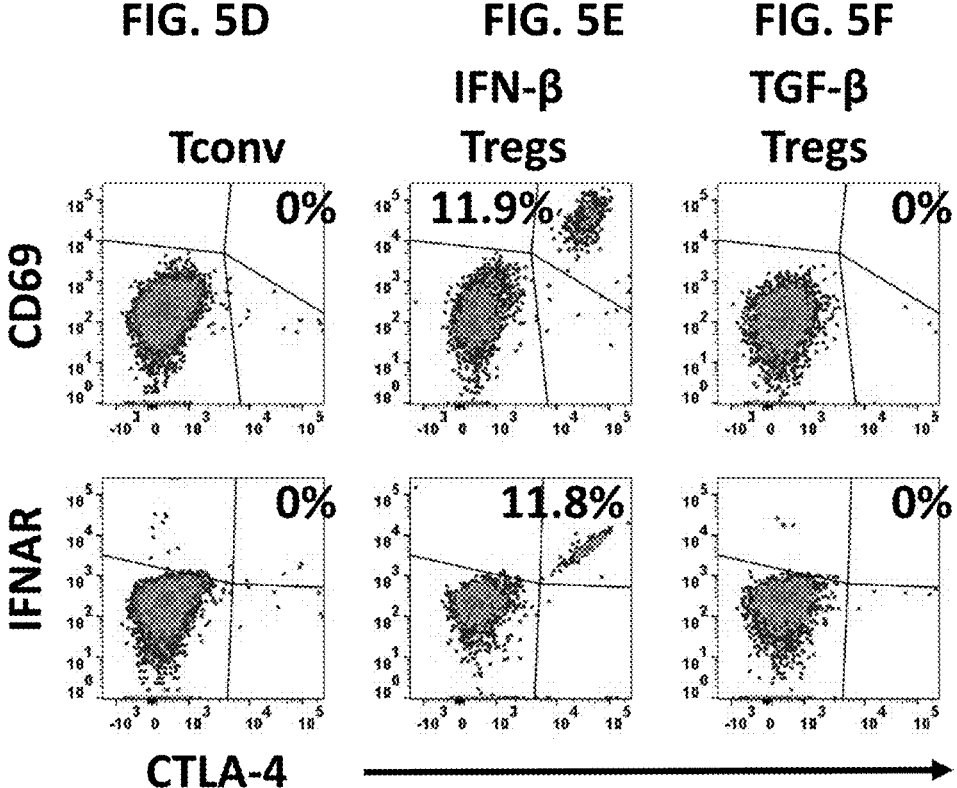

Splenic 2D2-FIG IFN-β-induced Tregs were assessed for suppressive activity in adoptive transfer experiments (FIGS. 5A-5B, Table 1). Donor IFNβ-Tregs were compared to control FOXP3[null] 2D2 conventional T cells that were cultured without IFN-β. T cells were extensively washed and injected 4 days after encephalitogenic challenge. Recipients of IFN-β Tregs were protected from EAE as measured by clinical grade or weight loss (FIGS. 5A-5B) compared to recipients of control T cells or to saline treated mice. These data indicated that IFN-β supported the MOG-dependent expression of FOXP3 (FIGS. 4A-4D) and elicited the acquisition of suppressive activity in adoptive transfer models (FIGS. 5A-5B). The implication was that IFN-β represented a gateway for the differentiation of suppressive MOG-specific FOXP3[+] Tregs. IFN-β-induced Tregs were also more heterogeneous than TGF-β-induced Tregs (FIG. 5C). For example, IFN-β-Tregs had a CD28[high] population, a CD5[low], GARP[+] population, a PD-1[high] population, a PD-1[(neg)], PDL2[+] population, and a CD69[+], CTLA-4[+] population that were largely absent in the TGF-β-Treg population. The CD69[+], CTLA-4[+] IFN-β Treg population also had high levels of the Type I Interferon Receptor (IFNAR-1) (FIG. 5E). The IFN-β-mediated induction of CTLA-4 and IFNAR was enriched in the FOXP3[+] subset but was not exclusive to FOXP3[+] Tregs because IFN-β also induced a CTLA-4[+] IFNAR[+] Tconv subset (data not shown). Thus, IFN-β induced the expression of these markers on both IFN-β cultivated Tconv and Treg subsets. In the absence of IFN-β, T cells cultured with MOG alone or with "MOG and TGF-β" did not exhibit CTLA-4, CD69, or IFNAR (FIGS. 5D, 5F). These data revealed a potential IFN-β regulatory loop in which culture with IFN-β elicited expression of the Type I Interferon receptor IFNAR on a subset of IFN-β-induced T cells.

Example 8

IFN-β and MOG Elicited FOXP3 Expression In Vivo

Figures 6A, 6B:
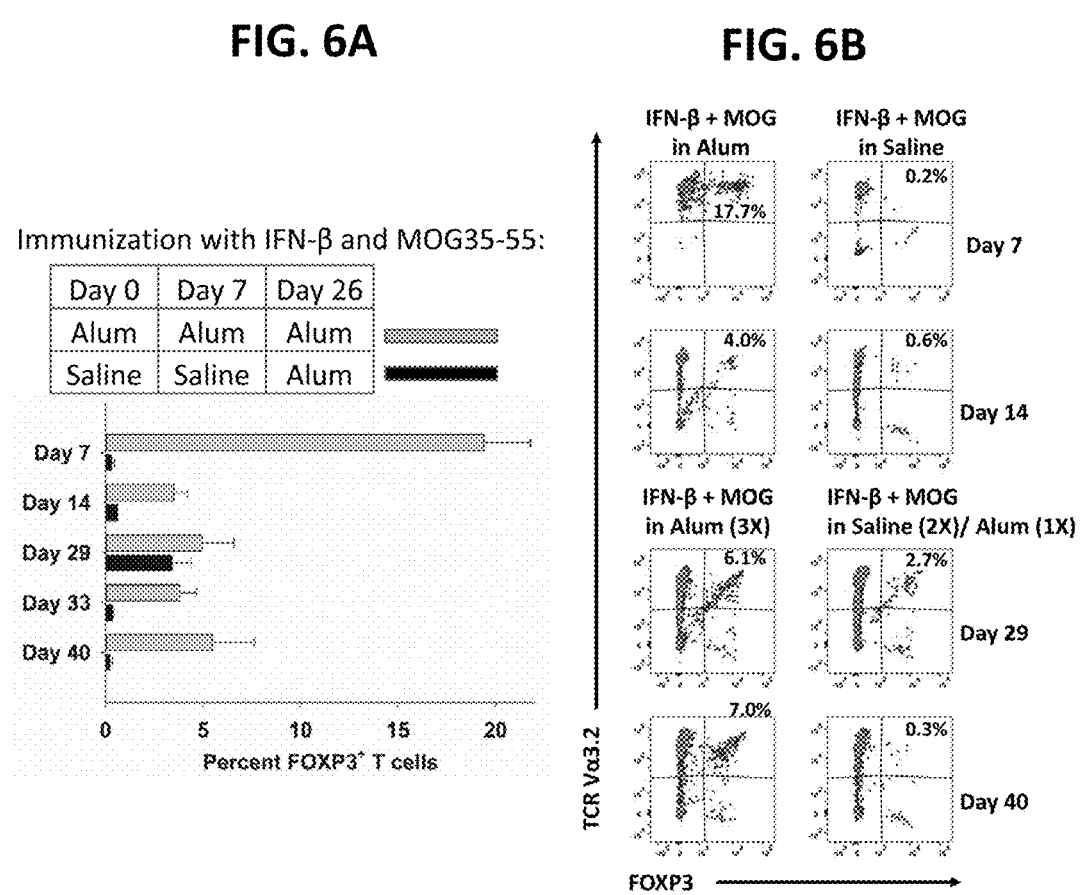
FIGS. 6A-6B. The "IFN-β+MOG in Alum" vaccine elicited FOXP3$^+$ Tregs in vivo. On days 0, 7, and 26, 2D2-FIG mice were injected subcutaneously (5 nmole dose) with "IFN-β+MOG in Alum". Another group was injected with 5 nmoles of "IFN-β+MOG in saline" on days 0 and 7 followed by one injection of "IFN-β+MOG in Alum" on day 26 (n=2).

Just as the combination of IFN-β and MOG elicited differentiation of Tregs in vitro (FIGS. 4A-4D and 5A-5F), immunization of 2D2-FIG mice with "IFN-β+MOG in Alum" also elicited FOXP3[+] Tregs in 2D2-FIG mice in vivo (FIGS. 6A-6B). On days 0 and 7, 2D2-FIG mice were injected subcutaneously (5 nmole dose) with "IFN-β+MOG in Alum" or "IFN-β+MOG in saline" (shown) or "IFN-β in saline", "MOG35-55 in saline", saline, or were untreated (not shown). On day 26, booster injections were repeated for all groups, but Alum rather than saline was used in all 5 groups. On days 7, 14, 29, 33, and 40, mice were bled via the submandibular vein, and circulating CD45[+] CD3[+] T cells were assessed for FOXP3[+] expression. In mice vaccinated with "IFN-β+MOG in Alum", over 17% of all circulating 2D2-FIG T cells on day 7 expressed FOXP3 (FIGS. 6A-6B). In mice vaccinated with "IFN-β+MOG in saline", only 0.2-0.4% of T cells expressed FOXP3. Mice that were vaccinated with "IFN-β+MOG in Alum" 3 times (days 0, 7, 26) maintained a steady population of circulating FOXP3[+] T cells through the last day of analysis on day 40 (FIGS. 6A-6B). In contrast, mice that received "IFN-β+MOG in Saline" on days 0 and 7 plus a boost of "IFN-β+MOG in Alum" on day 26 had a temporary presence of FOXP3[+] T cells on day 29 but not thereafter. Like mice that were untreated, mice that received "IFN-β in saline", "MOG35-55 in saline", or saline along with a booster of the same in Alum on day 26 did not express FOXP3 beyond background levels (<1%) at any point during the experiment. These data indicate that IFN-β, when combined with NAg and the Alum adjuvant, constitutes a vehicle for tolerogenic vaccination via induction of NAg-specific CD25[+] FOXP3[+] T cells.

TABLE 1

| Figure[a] | Group | Incidence | Attrition | Mean (±SE) cumulative scores | P value | Mean (±SE) maximal scores | P value | % maximal weight loss | P value |
|---|---|---|---|---|---|---|---|---|---|
| 1A, 1B | IFNβ-MOG | 7 of 8 | 0 of 8 | 57.9 ± 21.6 | * | 1.6 ± 0.5 | * | 17.0 ± 3.5% | * |
| 1A, 1B | IFNβ + MOG | 8 of 8 | 1 of 8 | 125.9 ± 15.2 | ns | 3.5 ± 0.4 | 0.023 | 22.0 ± 3.5% | ns |
| 1A, 1B | MOG35-55 | 8 of 8 | 0 of 8 | 138.3 ± 19.9 | 0.024 | 3.6 ± 0.4 | 0.006 | 23.9 ± 2.4% | ns |
| 1A, 1B | Saline | 8 of 8 | 0 of 8 | 163.3 ± 3.8 | 0.001 | 4.0 ± 0.0 | 0.001 | 27.7 ± 1.6% | ns |
| 1C, 1D | IFN-B + MOG in Alum | 4 of 4 | 0 of 4 | 23.6 ± 7.8 | * | 2.0 ± 0.0 | * | 15.3 ± 3.4% | * |
| 1C, 1D | MOG in Alum | 4 of 4 | 1 of 4 | 61.8 ± 3.9 | 0.014 | 4.1 ± 0.3 | 0.010 | 30.6 ± 4.3% | 0.037 |
| 1C, 1D | Saline in Alum | 5 of 5 | 4 of 5 | 57.9 ± 5.3 | 0.034 | 4.7 ± 0.3 | 0.001 | 28.7 ± 3.1% | 0.054 |
| 1E, 1F | IFN-β + MOG in Alum | 7 of 13 | 0 of 13 | 9.1 ± 3.9 | * | 1.0 ± 0.4 | * | 8.5 ± 1.6% | * |
| 1E, 1F | IFN-β + MOG in Saline | 8 of 8 | 5 of 8 | 31.0 ± 5.1 | 0.022 | 4.1 ± 0.1 | <0.001 | 20.3 ± 1.5% | 0.002 |
| 1E, 1F | MOG in Alum | 7 of 7 | 4 of 7 | 30.5 ± 3.5 | 0.013 | 4.3 ± 0.3 | <0.001 | 16.4 ± 2.7% | ns |
| 1E, 1F | Saline in Alum | 5 of 5 | 5 of 5 | 23.1 ± 3.0 | ns | 5.0 ± 0.0 | <0.001 | 21.2 ± 1.5% | 0.005 |
| 1E, 1F | Saline | 10 of 10 | 8 of 10 | 21.7 ± 5.5 | ns | 3.9 ± 0.4 | <0.001 | 22.2 ± 2.6% | <0.001 |
| 3A-3B | MOG-MOG | 6 of 7 | 0 of 7 | 16.5 ± 4.8 | * | 2.4 ± 0.6 | * | 4.7 ± 2.9% | * |
| 3A-3B | MOG-MOG (Anti-CD25) | 7 of 7 | 3 of 7 | 46.9 ± 2.5 | 0.002 | 4.1 ± 0.2 | 0.001 | 19.2 ± 2.3% | 0.001 |
| 3A-3B | PLP-MOG | 5 of 5 | 3 of 5 | 45.3 ± 5.4 | 0.002 | 4.2 ± 0.2 | <0.001 | 21.1 ± 3.6% | 0.001 |
| 3A-3B | PLP-MOG (Anti-CD25) | 6 of 6 | 3 of 6 | 46.9 ± 2.7 | 0.003 | 4.1 ± 0.2 | 0.001 | 20.9 ± 1.5% | 0.001 |

TABLE 1-continued

IFN-β is a tolerogenic adjuvant.

| Figure[a] | Group | Incidence | Attrition | Mean (±SE) cumulative scores | P value | Mean (±SE) maximal scores | P value | % maximal weight loss | P value |
|---|---|---|---|---|---|---|---|---|---|
| 3C-3D | MOG-PLP | 5 of 5 | 2 of 5 | 81.1 ± 2.5 | 0.000 | 4.3 ± 0.3 | 0.004 | 17.0 ± 1.8% | 0.009 |
| 3C-3D | MOG-PLP (Anti-CD25) | 5 of 5 | 3 of 5 | 65.0 ± 4.1 | ns | 4.4 ± 0.4 | 0.003 | 17.1 ± 3.3% | 0.009 |
| 3C-3D | PLP-PLP | 3 of 5 | 0 of 5 | 11.1 ± 10.6 | * | 0.8 ± 0.6 | * | 3.8 ± 0.6% | * |
| 3C-3D | PLP-PLP (Anti-CD25) | 5 of 5 | 1 of 5 | 68.2 ± 7.8 | 0.016 | 3.9 ± 0.3 | 0.028 | 15.3 ± 3.1% | 0.026 |
| 5A-5B | IFNβ-Tregs | 2 of 8 | 0 of 8 | 1.8 ± 1.4 | * | 0.2 ± 0.1 | * | 1.0 ± 0.8% | * |
| 5A-5B | Control T cells | 10 of 10 | 0 of 10 | 30.0 ± 4.6 | <0.001 | 2.7 ± 0.2 | <0.001 | 11.3 ± 2.5% | 0.030 |
| 5A-5B | Saline | 11 of 11 | 1 of 11 | 24.4 ± 3.5 | <0.001 | 2.9 ± 0.4 | <0.001 | 11.9 ± 2.5% | 0.016 |

[a]These data are portrayed graphically in FIGS. 1A-1F, 3A-3D, and 5A-5B. The experimental approach is described in the respective figure legend. For FIGS. 3A-3D, group designations MOG-MOG, PLP-MOG, MOG-PLP, PLP-PLP refers first to the peptide (MOG35-55 or PLP178-191) in the Alum + IFN-β tolerogenic vaccine and second to the peptide in the CFA challenge. Nonparametric ANOVA based on ranked scores was used to assess group differences in mean cumulative scores and mean maximal scores, and parametric ANOVA was used to assess group differences in percent maximal weight loss relative to the comparator group (*, Bonferroni Post-Hoc test).

Example 9

The IFN-β+NAg in Alum Vaccine Elicited Tolerance in 2D2-FIG Mice

Figures 7A, 7B, 7C:
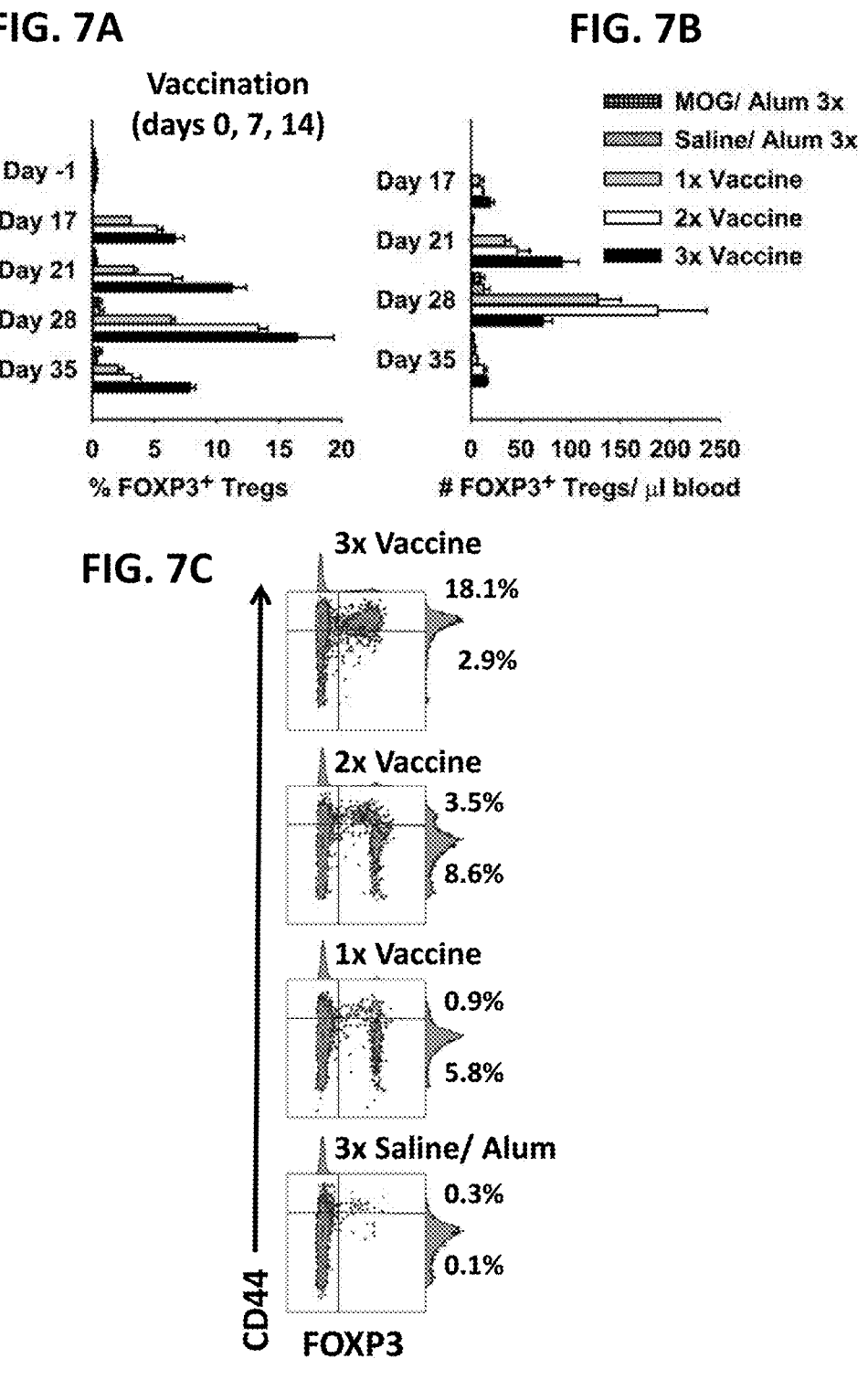

Given that one can use an IFN-β-based vaccine to elicit Treg responses (FIGS. 6A-6B), an important question was whether one could use repeated 'booster' vaccinations to amplify effector/memory Treg responses. 2D2-FIG mice were given three (3×) injections (days 0, 7, 14), two (2×) injections (days 7 and 14), or one (1×) injection (day 14) of 5 nmoles of the "IFN-β+MOG in Alum" vaccine (1×, 2×, 3× vaccine, FIGS. 7A-7F). Control groups were given three (3×) injections (days 0, 7, 14) of 5 nmoles of "MOG in Alum" or "Saline in Alum". Tolerogenic vaccination with "IFN-β+MOG in Alum" (3×, 2×, and 1×) elicited FOXP3+ Tregs in PBMC when assayed on days 17, 21, 28, and 35 (FIGS. 7A-7B). Repeated boosters generally resulted in higher FOXP3+ Treg percentages (FIG. 7A) and numbers (FIG. 7B). By day 28, mice that received 3 vaccinations also had circulating Tregs that expressed high levels of CD44 whereas Tregs from the 2×, 1×, or control groups expressed intermediate levels of CD44 (FIGS. 7C-7F). These data indicated that multiple tolerogenic boosters increased the abundance and memory phenotype of circulating FOXP3+ Tregs.

By day 35, percentages of Tregs waned in that only low levels of FOXP3+ Tregs remained in circulation. An important question was whether waning Treg levels in the blood correlated with waning resistance to EAE, but this was not the case (FIG. 7F and Table 2). When challenged to induce EAE on day 40, 2D2-FIG mice previously vaccinated with "IFN-β+MOG in Alum" once (1×) or three (3×) times exhibited profound resistance to EAE compared to controls. Two mice in the '2× vaccine' group exhibited 'late-breaking' paralytic EAE whereas one mouse remained disease-free throughout the observation period. EAE 'break-through' in the 2× group most likely represented stochastic events. We therefore refrain from any conclusions regarding comparison of the 2× group to the 1× or 3× groups of mice. When the 1×, 2×, and 3× groups were analyzed in aggregate, mice that received tolerogenic vaccination (Table 2a-c) were significantly more resistant to EAE than mice in the three pooled control groups (Table 2d-f). These data indicate that tolerogenic vaccination with "IFN-β+MOG in Alum" elicits an enduring tolerance in 2D2 TCR transgenic mice. Induction of tolerance in TCR transgenic mice is a stringent test of tolerogenic vaccine efficacy because the vast majority of T cells bear the transgenic MOG-specific TCR, and the vaccine must control this expanded MOG-specific T cell population. The persistence of tolerance despite the gradual disappearance of FOXP3+ Tregs from the blood is consistent with the possibility that circulating Tregs may emigrate from the blood into the peripheral tissues to maintain tolerance. To confirm induction of tolerance in the 2D2-FIG model, vaccines comprised of "IFN-β+MOG35-55 in Alum", "IFN-β+OVA323-339 in Alum", or "MOG35-55 in Alum" (5 nmoles) were given on days −21, −14, and −7 followed by active challenge with MOG35-55/CFA on day 0. As shown in FIG. 8 and Table 2, the "IFN-β+MOG in Alum" prevented the subsequent induction of EAE and EAE-associated weight loss whereas the control vaccines had no effect on induction of severe paralytic EAE.

TABLE 2

Tolerogenic vaccination with "IFN-β + MOG in Alum" elicits tolerance in 2D2 TCR transgenic mice.

| Figure | Group[a] | Incidence | Attrition | Cumulative EAE | P value | P value | Maximal EAE | P value | P value | Maximum Weight Loss | P value |
|---|---|---|---|---|---|---|---|---|---|---|---|
| 7F | (a) IFN-β + MOG in Alum (3x) | 1/3 | 0/3 | 0.2 ± 0.2 | 0.017 | 0.000 | 0.2 ± 0.2 | 0.020 | 0.000 | 1.2 ± 1.3% | 0.019 |
| 7F | (b) IFN-β + MOG in Alum (2x) | 2/3 | 0/3 | 25.8 ± 13.1 | ns | | 2.2 ± 1.1 | ns | | 13.3 ± 4.5% | |
| 7F | (c) IFN-β + MOG in Alum (1x) | 1/3 | 0/3 | 0.3 ± 0.3 | 0.022 | | 0.2 ± 0.2 | 0.020 | | 2.6 ± 1.1% | |

TABLE 2-continued

Tolerogenic vaccination with "IFN-β + MOG in Alum" elicits tolerance in 2D2
TCR transgenic mice.

| Figure | Group[a] | Incidence | Attrition | Cumulative EAE | P value | P value | Maximal EAE | P value | P value | Maximum Weight Loss | P value |
|--------|----------|-----------|-----------|----------------|---------|---------|-------------|---------|---------|---------------------|---------|
| 7F | (d) Saline in Alum (3x) | 3/3 | 2/3 | 64.5 ± 11.9 | ns | * | 4.7 ± 0.3 | * | * | 25.6 ± 1.6% | * |
| 7F | (e) MOG in Alum (3x) | 3/3 | 2/3 | 41.2 ± 17.4 | ns | | 3.7 ± 1.3 | ns | | 20.4 ± 6.7% | |
| 7F | (f) Naive | 6/6 | 3/6 | 56.3 ± 11.9 | * | | 3.5 ± 0.6 | ns | | 10.0 ± 5.0% | |
| 8A-8B | (g) IFN-β + MOG in Alum (3x) | 8/8 | 0/8 | 2.9 ± 0.9 | 0.002 | 0.005 | 0.6 ± 0.1 | 0.003 | 0.003 | 4.5 ± 1.2% | 0.000 |
| 8A-8B | (h) IFN-β + OVA in Alum (3x) | 8/8 | 2/8 | 31.8 ± 5.4 | | * | 3.9 ± 0.3 | | * | 24.7 ± 3.5% | * |
| 8A-8B | (i) MOG in Alum (3x) | 6/6 | 1/6 | 38.2 ± 4.3 | * | | 4.3 ± 0.3 | * | | 29.9 ± 2.7% | * |

[a]These data are portrayed graphically in FIGS. 7F and 8A-8B. The experimental approach is described in the figure legends. Nonparametric ANOVA based on ranked scores was used to assess group differences in mean cumulative scores and mean maximal scores relative to the comparator group whereas parametric ANOVA was used to assess weight loss (*, Bonferroni Post-Hoc test; a-e versus f, g versus h and i). An Independent Samples T-test was used to analyze differences in data compiled for tolerogenic vaccination (a-c) versus control groups (d-f).

Example 10

IFN-β Adjuvant Promotion of Infectious Tolerance

B6 mice were vaccinated with "OVA in Alum", "IFN-β+OVA+MOG in Alum", or "IFN-β+OVA in Alum" on day −8 and then were challenged with either "OVA+MOG in CFA" or "MOG in CFA" on day 0. (FIGS. 9A-9D, Table 3). The results showed that the "OVA in Alum" vaccine had no activity whereas the "IFN-β+OVA+MOG in Alum" inhibited the subsequent induction of EAE (FIGS. 9A-9B). The key observation was that the "IFN-β+OVA in Alum" vaccine was or was not effective depending on whether OVA was or was not included in the MOG/CFA emulsion, respectively (FIGS. 9C-9D). That is, the "IFN-β+OVA in Alum" vaccine inhibited EAE upon immunization with "OVA+MOG"/CFA but did not impact EAE upon immunization with MOG/CFA. These data were consistent with the possibility that vaccine-induced, OVA-specific Tregs modulated EAE only when OVA was included in the encephalitogenic emulsion. These data revealed the potential cross-regulation of encephalitogenic T cell precursors by OVA-specific Tregs when the respective epitopes were presented in the same localized environment or on the same APC.

Example 11

Interplay of TGF-β and IFN-β in Mechanisms of Treg Induction

Both IFN-β and TGF-β shared overlapping functionality for antigen-dependent induction of CD25+ FOXP3+ Tregs. However, IFN-β was less efficient and required substantially higher concentrations than TGF-β (e.g., 1 μM IFN-β versus 1 nM TGF-β, FIGS. 4A-4D). This observation suggested the possibility that IFN-β-mediated Treg induction may be TGF-β-dependent. To assess this issue, naïve 2D2-FIG splenocytes were cultured in the presence or absence of 1 μM IFN-β, 100 pM TGF-β, 31.6 μg/ml anti-mouse-TGF-β (1D11.16.8, mouse IgG1), or an isotype control anti-rat-LFA-1 (LRTC 1, mouse IgG1) with 1 μM MOG35-55 (FIGS. 10A-10E) or without antigen (not shown). The results showed that induction of IFN-β-Tregs was fully blocked by the anti-TGF-β mAb (FIGS. 10A, 10B, 10C, 10E). Control cultures showed that TGF-β activity was also blocked by anti-TGF-β (FIGS. 10A, 10D, 10E). IFN-β-mediated induction of Tregs as measured by T cell percentage or absolute numbers was inhibited by anti-TGF-β but not by the isotype control mAb (FIGS. 10B, 10E). The

TABLE 3

IFN-β is an adjuvant that fosters 'infectious tolerance'.

| Vaccine in Alum | Challenge in CFA | Incidence | Mean (±SE cumulative scores | P value | Mean (±SE) maximal scores | P value | % maximal weight loss | P value |
|-----------------|------------------|-----------|------------------------------|---------|----------------------------|---------|------------------------|---------|
| IFN-β + OVA + MOG | OVA + MOG | 4 of 9 | 6.5 ± 6.2 | ns | 0.6 ± 0.4 | ns | 2.7 ± 1.5 | ns |
| IFN-β + OVA + MOG | MOG | 3 of 8 | 7.2 ± 5.2 | ns | 0.8 ± 0.5 | ns | 5.6 ± 1.9 | ns |
| IFN-β + OVA | OVA + MOG | 2 of 8 | 0.4 ± 0.4 | * | 0.2 ± 0.1 | * | 2.9 ± 1.1 | * |
| IFN-β + OVA | MOG | 8 of 8 | 37.3 ± 9.9 | p < 0.001 | 3.0 ± 0.4 | p ≤ 0.001 | 11.7 ± 2.9 | ns |
| OVA | OVA + MOG | 6 of 6 | 47.6 ± 11.2 | p < 0.001 | 3.0 ± 0.5 | p ≤ 0.001 | 13.1 ± 4.8 | ns |
| OVA | MOG | 7 of 7 | 54.5 ± 13.2 | p < 0.001 | 3.4 ± 0.5 | p ≤ 0.001 | 15.7 ± 3.7 | p = 0.027 |

[a]These data are portrayed graphically in FIGS. 9A-9D. Mice were vaccinated once with three different vaccines including "IFN-B + OVA + MOG in Alum", "IFN-B + OVA in Alum", and "OVA in Alum" (5 nmole dose for all reagents) on day −8. Mice were then challenged with two different emulsions to induce EAE, including "OVA + MOG in CFA" and "MOG in CFA" (100 μg dose for each peptide) on day 0. Pertussis toxin was given on days 0 and 2. Nonparametric ANOVA based on ranked scores was used to assess group differences in mean cumulative scores and mean maximal scores, and parametric ANOVA was used to assess group differences in percent maximal weight loss relative to the comparator group (*, Bonferroni Post-Hoc test).

inhibitory activity of the 1D11 anti-TGF-β mAb reflected a competitive interaction (FIG. 10D). In cultures induced with 1 μM IFN-β or 100-316 PM TGF-β, 50% inhibition was evident at 1D11 concentrations of approximately 1 μg/ml (FIGS. 10C-10D). Overall, these data indicate the IFN-β elicits FOXP3+ Treg differentiation in vitro, at least in part, through the action of TGF-β. Although IFN-β elicited FOXP3+ Tregs via a TGF-β dependent mechanism, these data did not preclude the possibility that unique IFN-β activities apart from TGF-β shaped Treg differentiation and function.

Given the possibility that IFN-β may act indirectly via the induction of TGF-β, a relevant question was whether TGF-β, like IFN-β, may exhibit activity as a tolerogenic adjuvant in Alum. Thus, we assessed the relative activity of IFN-β versus TGF-β for induction of FOXP3+ T cells upon tolerogenic vaccination of 2D2-FIG mice (FIGS. 11A-11E). The full biological potency of both IFN-β and TGF-β preparations were confirmed by in vitro bioassay. Administration of "IFN-β+MOG35-55 in Alum" elicited increased percentages (FIGS. 11A-11B) and numbers (FIG. 11C) of Tregs in PBMC compared to vaccination with "Saline in Alum". The "IFN-β+MOG35-55 in Alum" vaccine also increased percentages (FIG. 11D) and numbers (not shown) of circulating granulocytes. The latter observation may reflect IFN-β-mediated activation of an innate immune response. Administration of TGF-β at a dose of either 5 nmoles or 2 nmoles with MOG35-55 (5 nmoles) in Alum also increased the total number of FOXP3+ Tregs per μl of blood (FIG. 11C), but this increase reflected a proportional increase in the number of CD3+ T cells (FIG. 11E) and total leukocytes (not shown). Overall, TGF-β-based vaccination did not elicit increased FOXP3+ Tregs as a percentage of the CD4+ T cell pool (FIGS. 11A-11B) or the total leukocyte pool. Cytokine adsorption to Alum was evident for both IFN-β and TGF-β because both were completely bound during incubation with Alum (data not shown). These data revealed differential activities of IFN-β and TGF-β for Treg induction in vivo, with the implication that IFN-β may have a more dedicated alignment with the FOXP3 T cell lineage compared to TGF-β.

These studies evidence that IFN-β is a gateway cytokine that polarizes T cell differentiation toward the immunosuppressive FOXP3+ Treg lineage. Furthermore, these studies reveal that the regulatory activities of IFN-β can be exploited to impose tolerogenic memory for specific myelin NAg.

Regarding the aluminum-based adjuvant, it is believed that (a) alum provided a stable antigen depot required for persistent antigenic exposure, (b) alum provided the physical matrix that enabled IFN-β/NAg crosslinking requisite for effective vaccination, and (c) alum had the compatibility needed for induction of tolerogenic FOXP3+ Treg responses because the adjuvant's intrinsic activities on innate immunity did not interfere or preempt Treg responses.

In general, these studies revealed a novel approach by which an autoimmune antigen and an anti-inflammatory cytokine can be formulated in an aluminum-based carrier as an effective tolerogenic vaccine.

TABLE 4

| Amino Acids | | | Codons | | | |
|---|---|---|---|---|---|---|
| Alanine | Ala | A | GCA | GCC | GCG | GCT |
| Cysteine | Cys | C | TGC | TGT | | |
| Aspartic acid | Asp | D | GAC | GAT | | |
| Glutamic acid | Glu | E | GAA | GAG | | |

TABLE 4-continued

| Amino Acids | | | Codons | | | |
|---|---|---|---|---|---|---|
| Phenylalanine | Phe | F | TTC | TTT | | |
| Glycine | Gly | G | GGA | GGC | GGG | GGT |
| Histidine | His | H | CAC | CAT | | |
| Isoleucine | Ile | I | ATA | ATC | ATT | |
| Lysine | Lys | K | AAA | AAG | | |
| Leucine | Leu | L | TTA | TTG | CTA | CTC | CTG | CTT |
| Methionine | Met | M | ATG | | | |
| Asparagine | Asn | N | AAC | AAT | | |
| Proline | Pro | P | CCA | CCC | CCG | CCT |
| Glutamine | Gln | Q | CAA | CAG | | |
| Arginine | Arg | R | AGA | AGG | CGA | CGC | CGG | CGT |
| Serine | Ser | S | AGC | ACT | TCA | TCC | TCG | TCT |
| Threonine | Thr | T | ACA | ACC | ACG | ACT |
| Valine | Val | V | GTA | GTC | GTG | GTT |
| Tryptophan | Trp | W | TGG | | | |
| Tyrosine | Tyr | Y | TAC | TAT | | |

REFERENCES

1. Nylander, A., and D. A. Hafler. 2012. Multiple sclerosis. J. Clin. Invest. 122:1180-1188.
2. Comabella, M., and S. J. Khoury. 2012. Immunopathogenesis of multiple sclerosis. Clin. Immunol. 142:2-8.
3. Steinman, L. 2009. The gray aspects of white matter disease in multiple sclerosis. Proc. Natl. Acad. Sci. U.S.A 106:8083-8084.
4. McGraw, C. A., and F. D. Lublin. 2013. Interferon beta and glatiramer acetate therapy. Neurotherapeutics 10:2-18.
5. Killestein, J., and C. H. Polman. 2011. Determinants of interferon beta efficacy in patients with multiple sclerosis. Nat. Rev. Neurol. 7:221-228.
6. Derwenskus, J. 2011. Current disease-modifying treatment of multiple sclerosis. Mt. Sinai J. Med. 78:161-175.
7. Kieseier, B. C. 2011. The mechanism of action of interferon-beta in relapsing multiple sclerosis. CNS drugs 25:491-502.
8. Rudick, R. A., and S. E. Goelz. 2011. Beta-interferon for multiple sclerosis. Exp. Cell Res. 317:1301-1311.
9. Borden, E. C., G. C. Sen, G. Uze, R. H. Silverman, R. M. Ransohoff, G. R. Foster, and G. R. Stark. 2007. Interferons at age 50: past, current and future impact on biomedicine. Nat Rev Drug Discov 6:975-990.
10. Axtell, R. C., C. Raman, and L. Steinman. 2013. Type I interferons: beneficial in Th1 and detrimental in Th17 autoimmunity. Clin. Rev. Allergy Immunol. 44:114-120.
11. Inoue, M., K. L. Williams, T. Oliver, P. Vandenabeele, J. V. Rajan, E. A. Miao, and M. L. Shinohara. 2012. Interferon-beta therapy against EAE is effective only when development of the disease depends on the NLRP3 inflammasome. Science signaling 5: ra38.
12. Simmons, S. B., E. R. Pierson, S. Y. Lee, and J. M. Goverman. 2013. Modeling the heterogeneity of multiple sclerosis in animals. Trends Immunol. 34:410-422.
13. Rangachari, M., and V. K. Kuchroo. 2013. Using EAE to better understand principles of immune function and autoimmune pathology. J. Autoimmun. 45:31-39.
14. Marta, C. B., A. R. Oliver, R. A. Sweet, S. E. Pfeiffer, and N. H. Ruddle. 2005. Pathogenic myelin oligodendrocyte glycoprotein antibodies recognize glycosylated epitopes and perturb oligodendrocyte physiology. Proc. Natl. Acad. Sci. U.S.A 102:13992-13997.
15. Oliver, A. R., G. M. Lyon, and N. H. Ruddle. 2003. Rat and human myelin oligodendrocyte glycoproteins induce experimental autoimmune encephalomyelitis by different mechanisms in C57BL/6 mice. J. Immunol. 171:462-468.

16. Swanborg, R. H. 1973. Antigen-induced inhibition of experimental allergic encephalomyelitis. II. Studies in guinea pigs with the small rat myelin basic protein. J. Immunol. 111:1067-1070.

17. Higgins, P. J., and H. L. Weiner. 1988. Suppression of experimental autoimmune encephalomyelitis by oral administration of myelin basic protein and its fragments. J. Immunol. 140:440-445.

18. Brod, S. A., A. al-Sabbagh, R. A. Sobel, D. A. Hafler, and H. L. Weiner. 1991. Suppression of experimental autoimmune encephalomyelitis by oral administration of myelin antigens: IV. Suppression of chronic relapsing disease in the Lewis rat and strain 13 guinea pig. Ann. Neurol. 29:615-622.

19. Javed, N. H., I. E. Gienapp, K. L. Cox, and C. C. Whitacre. 1995. Exquisite peptide specificity of oral tolerance in experimental autoimmune encephalomyelitis. J. Immunol. 155:1599-1605.

20. Campbell, B., P. J. Vogel, E. Fisher, and R. Lorenz. 1973. Myelin basic protein administration in multiple sclerosis. Arch. Neurol. 29:10-15.

21. Faria, A. M., and H. L. Weiner. 2005. Oral tolerance. Immunol. Rev. 206:232-259.

22. Loo, E. W., M. J. Krantz, and B. Agrawal. 2012. High dose antigen treatment with a peptide epitope of myelin basic protein modulates T cells in multiple sclerosis patients. Cell. Immunol. 280:10-15.

23. Freedman, M. S., A. Bar-Or, J. Oger, A. Traboulsee, D. Patry, C. Young, T. Olsson, D. Li, H. P. Hartung, M. Krantz, L. Ferenczi, and T. Verco. 2011. A phase III study evaluating the efficacy and safety of MBP8298 in secondary progressive MS. Neurology 77:1551-1560.

24. Darlington, C. 2007. MBP-8298, a synthetic peptide analog of myelin basic protein for the treatment of multiple sclerosis. Curr. Opin. Mol. Ther. 9:398-402.

25. McFarland, H. I., A. A. Lobito, M. M. Johnson, G. R. Palardy, C. S. Yee, E. K. Jordan, J. A. Frank, N. Tresser, C. P. Genain, J. P. Mueller, L. A. Matis, and M. J. Lenardo. 2001. Effective antigen-specific immunotherapy in the marmoset model of multiple sclerosis. J. Immunol. 166: 2116-2121.

26. Elliott, E. A., H. I. McFarland, S. H. Nye, R. Cofiell, T. M. Wilson, J. A. Wilkins, S. P. Squinto, L. A. Matis, and J. P. Mueller. 1996. Treatment of experimental encephalomyelitis with a novel chimeric fusion protein of myelin basic protein and proteolipid protein. J. Clin. Invest. 98:1602-1612.

27. Bielekova, B., B. Goodwin, N. Richert, I. Cortese, T. Kondo, G. Afshar, B. Gran, J. Eaton, J. Antel, J. A. Frank, H. F. McFarland, and R. Martin. 2000. Encephalitogenic potential of the myelin basic protein peptide (amino acids 83-99) in multiple sclerosis: results of a phase II clinical trial with an altered peptide ligand. Nat. Med. 6:1167-1175.

28. Wraith, D. C. 2009. Therapeutic peptide vaccines for treatment of autoimmune diseases. Immunol. Lett. 122: 134-136.

29. Garren, H. 2009. DNA vaccines for autoimmune diseases. Expert review of vaccines 8:1195-1203.

30 Walczak, A., M. Siger, A. Ciach, M. Szczepanik, and K. Selmaj. 2013. Transdermal application of myelin peptides in multiple sclerosis treatment. JAMA neurology: 1-6.

31. Jurynczyk, M., A. Walczak, A. Jurewicz, D. Jesionek-Kupnicka, M. Szczepanik, and K. Selmaj. 2010. Immune regulation of multiple sclerosis by transdermally applied myelin peptides. Ann. Neurol. 68:593-601.

32. Lutterotti, A., S. Yousef, A. Sputtek, K. H. Sturner, J. P. Stellmann, P. Breiden, S. Reinhardt, C. Schulze, M. Bester, C. Heesen, S. Schippling, S. D. Miller, M. Sospedra, and R. Martin. 2013. Antigen-specific tolerance by autologous myelin peptide-coupled cells: a phase 1 trial in multiple sclerosis. Sci. Transl. Med. 5: 188ra175.

33. Getts, D. R., A. J. Martin, D. P. McCarthy, R. L. Terry, Z. N. Hunter, W. T. Yap, M. T. Getts, M. Pleiss, X. Luo, N. J. King, L. D. Shea, and S. D. Miller. 2012. Microparticles bearing encephalitogenic peptides induce T-cell tolerance and ameliorate experimental autoimmune encephalomyelitis. Nat. Biotechnol. 30:1217-1224.

34. Getts, D. R., D. M. Turley, C. E. Smith, C. T. Harp, D. Mccarthy, E. M. Feeney, M. T. Getts, A. J. Martin, X. Luo, R. L. Terry, N. J. King, and S. D. Miller. 2011. Tolerance induced by apoptotic antigen-coupled leukocytes is induced by PD-L1+ and IL-10-producing splenic macrophages and maintained by T regulatory cells. J. Immunol. 187:2405-2417.

35. Hawiger, D., R. F. Masilamani, E. Bettelli, V. K. Kuchroo, and M. C. Nussenzweig. 2004. Immunological unresponsiveness characterized by increased expression of CD5 on peripheral T cells induced by dendritic cells in vivo. Immunity 20:695-705.

36. Stern, J. N., D. B. Keskin, Z. Kato, H. Waldner, S. Schallenberg, A. Anderson, H. von Boehmer, K. Kretschmer, and J. L. Strominger. 2010. Promoting tolerance to proteolipid protein-induced experimental autoimmune encephalomyelitis through targeting dendritic cells. Proc. Natl. Acad. Sci. U.S.A 107:17280-17285.

37. Mannie, M. D., and A. D. Curtis, 2nd. 2013. Tolerogenic vaccines for Multiple sclerosis. Hum. Vaccin. Immunother. 9:1032-1038.

38. Mannie, M. D., J. L. Blanchfield, S. M. Islam, and D. J. Abbott. 2012. Cytokine-neuroantigen fusion proteins as a new class of tolerogenic, therapeutic vaccines for treatment of inflammatory demyelinating disease in rodent models of multiple sclerosis. Front. Immunol. 3:255.

39. Abbott, D. J., J. L. Blanchfield, D. A. Martinson, S. C. Russell, N. Taslim, A. D. Curtis, and M. D. Mannie. 2011. Neuroantigen-specific, tolerogenic vaccines: GM-CSF is a fusion partner that facilitates tolerance rather than immunity to dominant self-epitopes of myelin in murine models of experimental autoimmune encephalomyelitis (EAE). BMC Immunol. 12:72.

40. Blanchfield, J. L., and M. D. Mannie. 2010. A GMCSF-neuroantigen fusion protein is a potent tolerogen in experimental autoimmune encephalomyelitis (EAE) that is associated with efficient targeting of neuroantigen to APC. J. Leukoc. Biol. 87:509-521.

41. Mannie, M. D., D. J. Abbott, and J. L. Blanchfield. 2009. Experimental autoimmune encephalomyelitis in Lewis rats: IFN-beta acts as a tolerogenic adjuvant for induction of neuroantigen-dependent tolerance. J. Immunol. 182: 5331-5341.

42. Mannie, M. D., J. L. Devine, B. A. Clayson, L. T. Lewis, and D. J. Abbott. 2007. Cytokine-neuroantigen fusion proteins: new tools for modulation of myelin basic protein (MBP)-specific T cell responses in experimental autoimmune encephalomyelitis. J. Immunol. Methods 319:118-132.

43. Mannie, M. D., B. A. Clayson, E. J. Buskirk, J. L. DeVine, J. J. Hernandez, and D. J. Abbott. 2007. IL-2/neuroantigen fusion proteins as antigen-specific tolerogens in experimental autoimmune encephalomyelitis (EAE): correlation of T cell-mediated antigen presentation and tolerance induction. J. Immunol. 178:2835-2843.

44. Mannie, M. D., and D. J. Abbott. 2007. A fusion protein consisting of IL-16 and the encephalitogenic peptide of myelin basic protein constitutes an antigen-specific tolerogenic vaccine that inhibits experimental autoimmune encephalomyelitis. J. Immunol. 179:1458-1465.

45. Zou, Z., and P. D. Sun. 2004. Overexpression of human transforming growth factor-beta1 using a recombinant CHO cell expression system. Protein Expr. Purif. 37:265-272.

46. Setiady, Y. Y., J. A. Coccia, and P. U. Park. 2010. In vivo depletion of CD4+FOXP3+ Treg cells by the PC61 anti-CD25 monoclonal antibody is mediated by FcgammaRIII+ phagocytes. Eur. J. Immunol. 40:780-786.

47. Lacal, J. C., and S. A. Aaronson. 1986. Monoclonal antibody Y13-259 recognizes an epitope of the p21 ras molecule not directly involved in the GTP-binding activity of the protein. Mol. Cell. Biol. 6:1002-1009.

48. Dasch, J. R., D. R. Pace, W. Waegell, D. Inenaga, and L. Ellingsworth. 1989. Monoclonal antibodies recognizing transforming growth factor-beta. Bioactivity neutralization and transforming growth factor beta 2 affinity purification. J. Immunol. 142:1536-1541.

49. Liu, V. C., L. Y. Wong, T. Jang, A. H. Shah, I. Park, X. Yang, Q. Zhang, S. Lonning, B. A. Teicher, and C. Lee. 2007. Tumor evasion of the immune system by converting CD4+CD25-T cells into CD4+CD25+ T regulatory cells: role of tumor-derived TGF-beta. J. Immunol. 178:2883-2892.

50. Mannie, M. D., J. Morrison-Plummer, B. Torres-Garcia, C. Hannaway, C. Jones, and A. M. Smith. 1994. Parallel costimulatory pathways promote myelin basic protein-stimulated proliferation of encephalitogenic rat T cells. Cell. Immunol. 153:312-328.

51. Arnold, P. Y., K. P. Kearse, C. A. Marinakis, and M. D. Mannie. 1998. A novel monoclonal antibody against rat LFA-1: blockade of LFA-1 and CD4 augments class II MHC expression on T cells. Hybridoma 17:331-338.

52. Mannie, M. D., J. P. Nardella, G. A. White, P. Y. Arnold, and D. K. Davidian. 1998. Class II MHC/peptide complexes on T cell antigen-presenting cells: agonistic antigen recognition inhibits subsequent antigen presentation. Cell. Immunol. 186:111-120.

53. Abreu, S. L. 1982. Suppression of experimental allergic encephalomyelitis by interferon. Immunol. Commun. 11:1-7.

54. Hertz, F., and R. Deghenghi. 1985. Effect of rat and beta-human interferons on hyperacute experimental allergic encephalomyelitis in rats. Agents Actions 16:397-403.

55. Brod, S. A., M. Khan, R. H. Kerman, and M. Pappolla. 1995. Oral administration of human or murine interferon alpha suppresses relapses and modifies adoptive transfer in experimental autoimmune encephalomyelitis. J. Neuroimmunol. 58:61-69.

56. Brod, S. A., M. Scott, D. K. Burns, and J. T. Phillips. 1995. Modification of acute experimental autoimmune encephalomyelitis in the Lewis rat by oral administration of type 1 interferons. J. Interferon Cytokine Res. 15:115-122.

57. Brod, S. A., and M. Khan. 1996. Oral administration of IFN-alpha is superior to subcutaneous administration of IFN-alpha in the suppression of chronic relapsing experimental autoimmune encephalomyelitis. J. Autoimmun. 9:11-20.

58. Vriesendorp, F. J., R. E. Flynn, M. Khan, M. A. Pappolla, and S. A. Brod. 1996. Oral administration of type I interferon modulates the course of experimental allergic neuritis. Autoimmunity 24:157-165.

59. Yu, M., A. Nishiyama, B. D. Trapp, and V. K. Tuohy. 1996. Interferon-beta inhibits progression of relapsing-remitting experimental autoimmune encephalomyelitis. J. Neuroimmunol. 64:91-100.

60. Yasuda, C. L., A. Al-Sabbagh, E. C. Oliveira, B. M. Diaz-Bardales, A. A. Garcia, and L. M. Santos. 1999. Interferon beta modulates experimental autoimmune encephalomyelitis by altering the pattern of cytokine secretion. Immunol. Invest. 28:115-126.

61. Tuohy, V. K., M. Yu, L. Yin, P. M. Mathisen, J. M. Johnson, and J. A. Kawczak. 2000. Modulation of the IL-10/IL-12 cytokine circuit by interferon-beta inhibits the development of epitope spreading and disease progression in murine autoimmune encephalomyelitis. J. Neuroimmunol. 111:55-63.

62. Floris, S., S. R. Ruuls, A. Wierinckx, S. M. van der Pol, E. Dopp, P. H. van der Meide, C. D. Dijkstra, and H. E. De Vries. 2002. Interferon-beta directly influences monocyte infiltration into the central nervous system. J. Neuroimmunol. 127:69-79.

63. Axtell, R. C., B. A. de Jong, K. Boniface, L. F. van der Voort, R. Bhat, P. De Sarno, R. Naves, M. Han, F. Zhong, J. G. Castellanos, R. Mair, A. Christakos, I. Kolkowitz, L. Katz, J. Killestein, C. H. Polman, R. de Waal Malefyt, L. Steinman, and C. Raman. 2010. T helper type 1 and 17 cells determine efficacy of interferon-beta in multiple sclerosis and experimental encephalomyelitis. Nat. Med. 16:406-412.

64. Galligan, C. L., L. M. Pennell, T. T. Murooka, E. Baig, B. Majchrzak-Kita, R. Rahbar, and E. N. Fish. 2010. Interferon-beta is a key regulator of proinflammatory events in experimental autoimmune encephalomyelitis. Mult. Scler. 16:1458-1473.

65. Kalinke, U., and M. Prinz. 2012. Endogenous, or therapeutically induced, type I interferon responses differentially modulate Th1/Th17-mediated autoimmunity in the CNS. Immunol. Cell Biol. 90:505-509.

66. Fitzgerald, D. C., Z. Fonseca-Kelly, M. L. Cullimore, P. Safabakhsh, C. J. Saris, G. X. Zhang, and A. Rostami. 2013. Independent and interdependent immunoregulatory effects of IL-27, IFN-beta, and IL-10 in the suppression of human Th17 cells and murine experimental autoimmune encephalomyelitis. J. Immunol. 190:3225-3234.

67. Inoue, M., and M. L. Shinohara. 2013. The role of interferon-beta in the treatment of multiple sclerosis and experimental autoimmune encephalomyelitis-in the perspective of inflammasomes. Immunology 139:11-18.

68. Hou, Y., C. Heon Ryu, J. A. Jun, S. M. Kim, C. H. Jeong, and S. S. Jeun. 2014. Interferon beta-secreting mesenchymal stem cells combined with minocycline attenuate experimental autoimmune encephalomyelitis. J. Neuroimmunol. 274:20-27.

69. Boivin, N., J. Baillargeon, P. M. Doss, A. P. Roy, and M. Rangachari. 2015. Interferon-beta suppresses murine Th1 cell function in the absence of antigen-presenting cells. PLOS One 10: e0124802.

70. Cheng, W., Q. Zhao, Y. Xi, C. Li, Y. Xu, L. Wang, X. Niu, Z. Wang, and G. Chen. 2015. IFN-beta inhibits T cells accumulation in the central nervous system by reducing the expression and activity of chemokines in experimental autoimmune encephalomyelitis. Mol. Immunol. 64:152-162.

71. Khorooshi, R., M. T. Morch, T. H. Holm, C. T. Berg, R. T. Dieu, D. Draeby, S. Issazadeh-Navikas, S. Weiss, S. Lienenklaus, and T. Owens. 2015. Induction of endogenous Type I interferon within the central nervous system plays a protective role in experimental autoimmune encephalomyelitis. Acta Neuropathol. 130:107-118.

72. Zhornitsky, S., T. A. Johnson, L. M. Metz, S. Weiss, and V. W. Yong. 2015. Prolactin in combination with interferon-beta reduces disease severity in an animal model of multiple sclerosis. J. Neuroinflammation 12:55.

73 de Andres, C., C. Aristimuno, V. de Las Heras, M. L. Martinez-Gines, M. Bartolome, R. Arroyo, J. Navarro, S. Gimenez-Roldan, E. Fernandez-Cruz, and S. Sanchez-Ramon. 2007. Interferon beta-1a therapy enhances CD4+ regulatory T-cell function: an ex vivo and in vitro longitudinal study in relapsing-remitting multiple sclerosis. J. Neuroimmunol. 182:204-211.

74. Korporal, M., J. Haas, B. Balint, B. Fritzsching, A. Schwarz, S. Moeller, B. Fritz, E. Suri-Payer, and B. Wildemann. 2008. Interferon beta-induced restoration of regulatory T-cell function in multiple sclerosis is prompted by an increase in newly generated naive regulatory T cells. Arch. Neurol. 65:1434-1439.

75. Vandenbark, A. A., J. Huan, M. Agotsch, D. La Tocha, S. Goelz, H. Offner, S. Lanker, and D. Bourdette. 2009. Interferon-beta-1a treatment increases CD56bright natural killer cells and CD4+CD25+ Foxp3 expression in subjects with multiple sclerosis. J. Neuroimmunol. 215: 125-128.

76. Aristimuno, C., C. de Andres, M. Bartolome, V. de las Heras, M. L. Martinez-Gines, R. Arroyo, E. Fernandez-Cruz, and S. Sanchez-Ramon. 2010. IFNbeta-1a therapy for multiple sclerosis expands regulatory CD8$^+$ T cells and decreases memory CD8+ subset: a longitudinal 1-year study. Clin. Immunol. 134:148-157.

77. Namdar, A., B. Nikbin, M. Ghabaee, A. Bayati, and M. Izad. 2010. Effect of IFN-beta therapy on the frequency and function of CD4 (+)CD25 (+) regulatory T cells and Foxp3 gene expression in relapsing-remitting multiple sclerosis (RRMS): a preliminary study. J. Neuroimmunol. 218:120-124.

78. Chen, M., G. Chen, S. Deng, X. Liu, G. J. Hutton, and J. Hong. 2012. IFN-beta induces the proliferation of CD4+ CD25+Foxp3+ regulatory T cells through upregulation of GITRL on dendritic cells in the treatment of multiple sclerosis. J. Neuroimmunol. 242:39-46.

79. Piconese, S., I. Pacella, E. Timperi, and V. Barnaba. 2014. Divergent effects of type-I interferons on regulatory T cells. Cytokine Growth Factor Rev. 26:133-141.

80. Lee, S. E., X. Li, J. C. Kim, J. Lee, J. M. Gonzalez-Navajas, S. H. Hong, I. K. Park, J. H. Rhee, and E. Raz.

2012. Type I interferons maintain Foxp3 expression and T-regulatory cell functions under inflammatory conditions in mice. Gastroenterology 143:145-154.

81. Metidji, A., S. A. Rieder, D. D. Glass, I. Cremer, G. A. Punkosdy, and E. M. Shevach. 2015. IFN-alpha/beta receptor signaling promotes regulatory T cell development and function under stress conditions. J. Immunol. 194:4265-4276.

82. Levings, M. K., R. Sangregorio, F. Galbiati, S. Squadrone, R. de Waal Malefyt, and M. G. Roncarolo. 2001. IFN-alpha and IL-10 induce the differentiation of human type 1 T regulatory cells. J. Immunol. 166:5530-5539.

83. Ziegler-Heitbrock, L., M. Lotzerich, A. Schaefer, T. Werner, M. Frankenberger, and E. Benkhart. 2003. IFN-alpha induces the human IL-10 gene by recruiting both IFN regulatory factor 1 and Stat3. J. Immunol. 171:285-290.

84. Dikopoulos, N., A. Bertoletti, A. Kroger, H. Hauser, R. Schirmbeck, and J. Reimann. 2005. Type I IFN negatively regulates CD8$^+$ T cell responses through IL-10-producing CD4+ T regulatory 1 cells. J. Immunol. 174:99-109.

85. Stewart, C. A., H. Metheny, N. lida, L. Smith, M. Hanson, F. Steinhagen, R. M. Leighty, A. Roers, C. L. Karp, W. Muller, and G. Trinchieri. 2013. Interferon-dependent IL-10 production by Tregs limits tumor Th17 inflammation. J. Clin. Invest. 123:4859-4874.

86. Liu, Y., R. Carlsson, M. Comabella, J. Wang, M. Kosicki, B. Carrion, M. Hasan, X. Wu, X. Montalban, M. H. Dziegiel, F. Sellebjerg, P. S. Sorensen, K. Helin, and S. Issazadeh-Navikas. 2014. FoxA1 directs the lineage and immunosuppressive properties of a novel regulatory T cell population in EAE and MS. Nat. Med. 20:272-282.

87. Islam, S. M., A. D. Curtis, 2nd, N. Taslim, D. S. Wilkinson, and M. D. Mannie. 2014. GM-CSF-neuroantigen fusion proteins reverse experimental autoimmune encephalomyelitis and mediate tolerogenic activity in adjuvant-primed environments: association with inflammation-dependent, inhibitory antigen presentation. J. Immunol. 193:2317-2329.

88 Ghosh, D., A. D. Curtis, 2nd, D. S. Wilkinson, and M. D. Mannie. 2016. Depletion of CD4$^+$ CD25+ regulatory T cells confers susceptibility to experimental autoimmune encephalomyelitis (EAE) in GM-CSF-deficient Csf2−/− mice. J. Leukoc. Biol.

89. Corthay, A. 2009. How do regulatory T cells work? Scand. J. Immunol. 70:326-336.

90. Lund, J. M., L. Hsing, T. T. Pham, and A. Y. Rudensky. 2008. Coordination of early protective immunity to viral infection by regulatory T cells. Science 320:1220-1224.

That which is claimed is:

1. A composition comprising:

(a) an autoimmune antigen selected from the group consisting of proteolipid protein (PLP), myelin oligodendrocyte glycoprotein (MOG), myelin-associated oligodendrocytic basic protein and cardiac myosin, or portions thereof, wherein the portions comprise the encephalitogenic determinant portion;

(b) an anti-inflammatory cytokine that is interferon alpha or interferon beta; and (c) an aluminum-based adjuvant which is noncovalently bound to both the autoimmune antigen and the anti-inflammatory cytokine, wherein the autoimmune antigen and the interferon alpha or interferon beta are not covalently linked.

2. The composition of claim 1, wherein the autoimmune antigen is an encephalitogenic determinant portion of an autoimmune antigen selected from the group consisting of proteolipid protein (PLP), myelin oligodendrocyte glycoprotein (MOG), myelin-associated oligodendrocytic basic protein and cardiac myosin, or portions thereof.

3. The composition of claim 1, wherein the anti-inflammatory cytokine is IFN-β.

4. The composition of claim 1, wherein the anti-inflammatory cytokine is IFN-α.

5. The composition of claim 1, wherein the aluminum-based adjuvant comprises aluminum hydroxide.

6. The composition of claim 1, wherein the aluminum-based adjuvant comprises aluminum oxyhydroxide.

7. The composition of claim 1, wherein the aluminum-based adjuvant comprises aluminum hydroxyphosphate.

8. The composition of claim 1, wherein the autoimmune antigen is proteolipid protein (PLP) or a portion thereof.

9. The composition of claim 1, wherein the autoimmune antigen is myelin oligodendrocyte glycoprotein (MOG) or a portion thereof.

10. The composition of claim 1, wherein the autoimmune antigen is myelin-associated oligodendrocytic basic protein and cardiac myosin or a portion thereof.

11. The composition of claim 2, wherein the encephalitogenic determinant portion of the PLP, MOG, myelin-associated oligodendrocytic basic protein or cardiac myosin is an amino acid sequence encoded by a nucleic acid sequence encoding an encephalitogenic determinant portion of the PLP, MOG, myelin-associated oligodendrocytic basic protein or cardiac myosin.

12. The composition of claim 2, wherein the encephalitogenic determinant portion of the PLP, MOG, myelin-associated oligodendrocytic basic protein or cardiac myosin is an amino acid sequence encoded by a nucleic acid sequence that hybridizes, under stringent conditions as represented by hybridization conditions of 0.5M NaHPO$_4$, 7% sodium dodecyl sulfate (SDS), 1 mM EDTA at 65° C. and wash conditions of 0.1×SSC/0.1% SDS at 68° C., with the complement of an amino acid sequence encoded by a nucleic acid sequence encoding an encephalitogenic determinant portion of the PLP, MOG, myelin-associated oligodendrocytic basic protein or cardiac myosin.

13. A kit comprising one or more container(s) including a pharmaceutical dosage unit comprising an effective amount of the composition of claim 1, wherein the kit is packaged with optional instructions for the use of the composition.

14. A composition comprising:

(a) myelin oligodendrocyte glycoprotein (MOG), (b) interferon beta; and (c) an aluminum-based adjuvant which is bound to both the autoimmune antigen and the anti-inflammatory cytokine, wherein the MOG and the interferon beta are not covalently linked.

\* \* \* \* \*